(12) United States Patent
Okerberg et al.

(10) Patent No.: US 12,043,862 B2
(45) Date of Patent: Jul. 23, 2024

(54) HIGH-THROUGHPUT SEROTYPING AND ANTIBODY PROFILING ASSAYS

(71) Applicant: Encodia, Inc., San Diego, CA (US)

(72) Inventors: Eric Okerberg, San Diego, CA (US); Kevin L. Gunderson, Encinitas, CA (US); Norihito Muranaka, San Diego, CA (US); Jongbum Kim, San Diego, CA (US); Byung Joon Lim, Seoul (KR); Lei Shi, San Diego, CA (US); Soumya Ganguly, San Diego, CA (US); Devin Sullivan, San Diego, CA (US)

(73) Assignee: ENCODIA, INC., San Diego, CA (US)

( * ) Notice: Subject to any disclaimer, the term of this patent is extended or adjusted under 35 U.S.C. 154(b) by 0 days.

(21) Appl. No.: 18/089,444

(22) Filed: Dec. 27, 2022

(65) Prior Publication Data

US 2023/0203562 A1     Jun. 29, 2023

Related U.S. Application Data

(60) Provisional application No. 63/294,374, filed on Dec. 28, 2021.

(51) Int. Cl.
*C12Q 1/6804* (2018.01)
*G01N 33/569* (2006.01)

(52) U.S. Cl.
CPC ..... *C12Q 1/6804* (2013.01); *G01N 33/56983* (2013.01); *G01N 2333/165* (2013.01); *G01N 2458/10* (2013.01); *G01N 2469/20* (2013.01)

(58) Field of Classification Search
CPC ........... C12Q 1/6804; G01N 33/56983; G01N 2333/165; G01N 2458/10; G01N 2469/20
(Continued)

(56) References Cited

U.S. PATENT DOCUMENTS

| 10,288,608 B2 | 5/2019 | Kozlov et al. |
| 2005/0084927 A1 | 4/2005 | Norioka et al. |

(Continued)

FOREIGN PATENT DOCUMENTS

| WO | 2018183779 A1 | 10/2018 | |
| WO | WO-2019089851 A1 * | 5/2019 | ......... C12N 15/1065 |

(Continued)

OTHER PUBLICATIONS

Lassauniere et al. Evaluation of nine commercial SARS-COV-2 immunoassays. medRxiv preprint. 2020, p. 1-15. [online] [retrieved Jul. 3, 2023]. <URL:https://www.medrxiv.org/content/10.1101/2020.04.09.20056325v1> (Year: 2020).*

(Continued)

*Primary Examiner* — Aaron A Priest
*Assistant Examiner* — Randi Lynn Beil
(74) *Attorney, Agent, or Firm* — MORRISON & FOERSTER LLP

(57) ABSTRACT

Provided herein are high-throughput, population-wide serotyping and antibody profiling assays. Disclosed variants of a Digital Serotyping assay employ next generation sequencing to measure the "serotyping profile" of barcoded subject serum antibodies tested against a range of DNA-tagged pathogen-derived antigens. The disclosed assay setup enables multiplexing in both the sample and antigen dimensions, generating a large multi-dimensional serotyping data set for more comprehensive serotyping profiling of large populations across a large number of antigens and possible pathogens. Moreover, the ability to easily scale and multiplex the number of peptide epitopes allows rapid updating of the assay content to monitor the ever-changing spectrum of pathogens. Additional applications of this technology include cancer immunology and autoimmune conditions (e.g., neoantigen or autoimmune profiling), screening for (Continued)

toxins, antibody therapeutics development, biosecurity, and veterinary medicine.

22 Claims, 26 Drawing Sheets

Specification includes a Sequence Listing.

(58) Field of Classification Search
USPC .......................................................... 506/41
See application file for complete search history.

(56) References Cited

U.S. PATENT DOCUMENTS

| | | | |
|---|---|---|---|
| 2006/0199279 | A1 | 9/2006 | Lopez-avila et al. |
| 2006/0259995 | A1 | 11/2006 | Cayouette et al. |
| 2008/0305957 | A1 | 12/2008 | Thisted et al. |
| 2009/0264300 | A1 | 10/2009 | Franch et al. |
| 2014/0051586 | A1 | 2/2014 | Pino |
| 2014/0102915 | A1 | 4/2014 | Hu et al. |
| 2016/0291007 | A1* | 10/2016 | Kozlov ............ G01N 33/54306 |
| 2017/0052194 | A1 | 2/2017 | Havranek et al. |
| 2017/0190751 | A1 | 7/2017 | Barasch et al. |
| 2018/0179591 | A1* | 6/2018 | Belgrader ............ C12Q 1/6806 |
| 2019/0145982 | A1 | 5/2019 | Chee et al. |
| 2019/0169689 | A1 | 6/2019 | Zhu et al. |
| 2020/0217853 | A1 | 7/2020 | Estandian et al. |
| 2020/0348308 | A1 | 11/2020 | Chee et al. |
| 2021/0079398 | A1 | 3/2021 | Pawlosky et al. |
| 2021/0214701 | A1 | 7/2021 | Desai et al. |
| 2021/0333275 | A1 | 10/2021 | Hulett |
| 2021/0355483 | A1 | 11/2021 | Chee et al. |

FOREIGN PATENT DOCUMENTS

| | | |
|---|---|---|
| WO | 2020236846 A1 | 11/2020 |
| WO | WO-2022038499 A1 * | 2/2022 |

OTHER PUBLICATIONS

Guo, C. et al. (Sep. 2018, e-pub. Jul. 9, 2018). "H1N1 Influenza Virus Epitopes Classified by Monoclonal Antibodies," Experimental and Therapeutic Medicine 16(3):2001-2007.

Kamath, K. et al. (Mar. 24, 2020). "Antibody Epitope Repertoire Analysis Enables Rapid Antigen Discovery and Multiplex Serology," Scientific Reports 10(1):5294, 9 pages.

Kozlov, I. A. et al. (2012, e-pub. Jun. 12, 2012). "A Highly Scalable Peptide-Based Assay System for Proteomics," PloS One 7(6):e37441, 10 pages.

Qi, H. et al. (Aug. 19, 2019). "Antibody Binding Epitope Mapping (AbMap) of Hundred Antibodies in a Single Run," Molecular and Cellular Proteomics 20:100059, 40 pages.

Shen, M. et al. (Mar. 1, 2017, e-pub. Mar. 1, 2018). "Site-Selective Orientated Immobilization of Antibodies and Conjugates for Immunodiagnostics Development," Methods 116:95-111, 40 pages.

Shrock, E. et al. (Nov. 27, 2020, e-pub. Sep. 29, 2020). "Coronavirus. Viral Epitope Profiling of COVID-19 Patients Reveals Cross-Reactivity and Correlates of Severity," Science 370(6520):eabd4250, 17 pages.

Xu, G. J. et al. (Jun. 5, 2015). "Viral Immunology. Comprehensive Serological Profiling of Human Populations Using a Synthetic Human Virome," Science 348(6239):aaa0698, 11 pages.

* cited by examiner

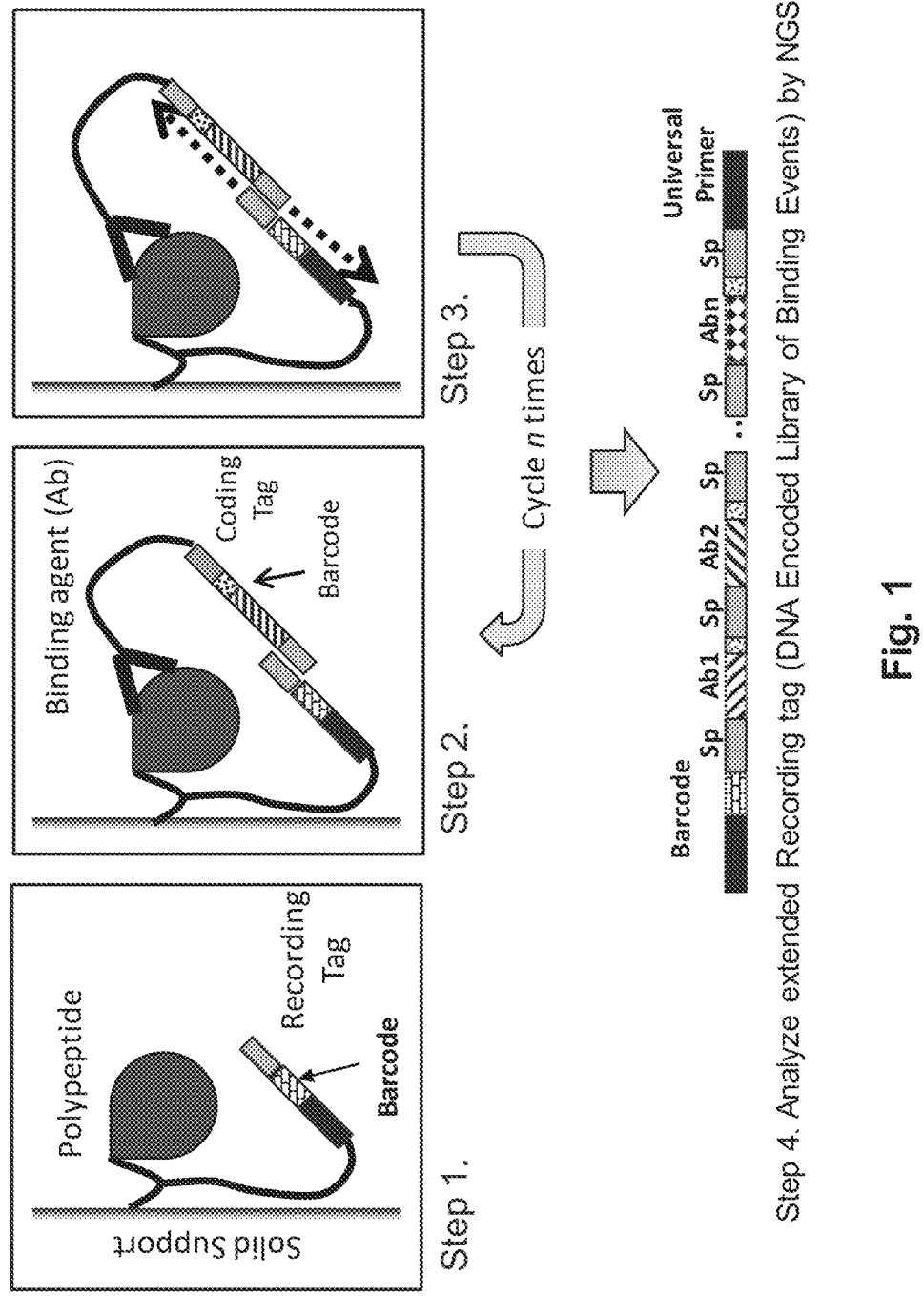

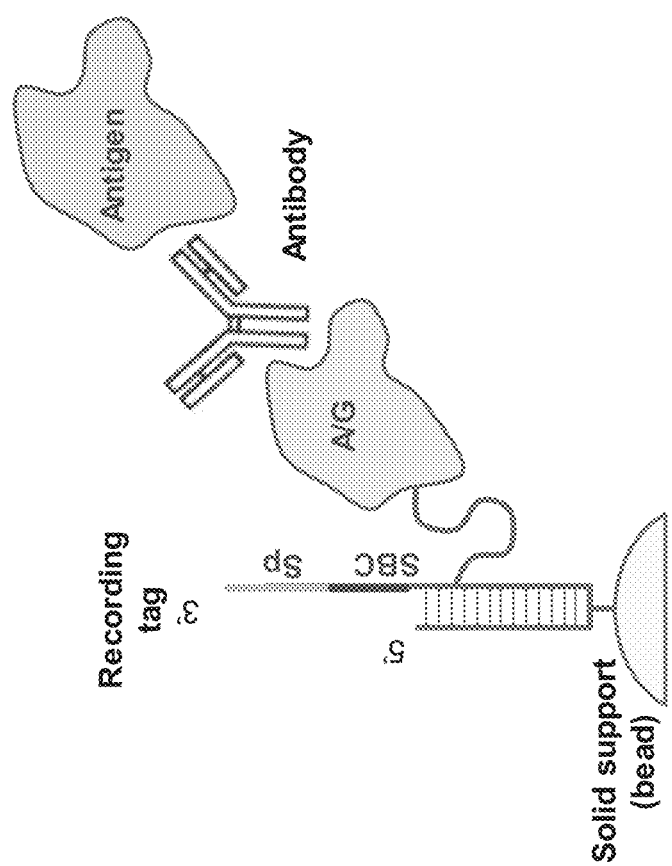

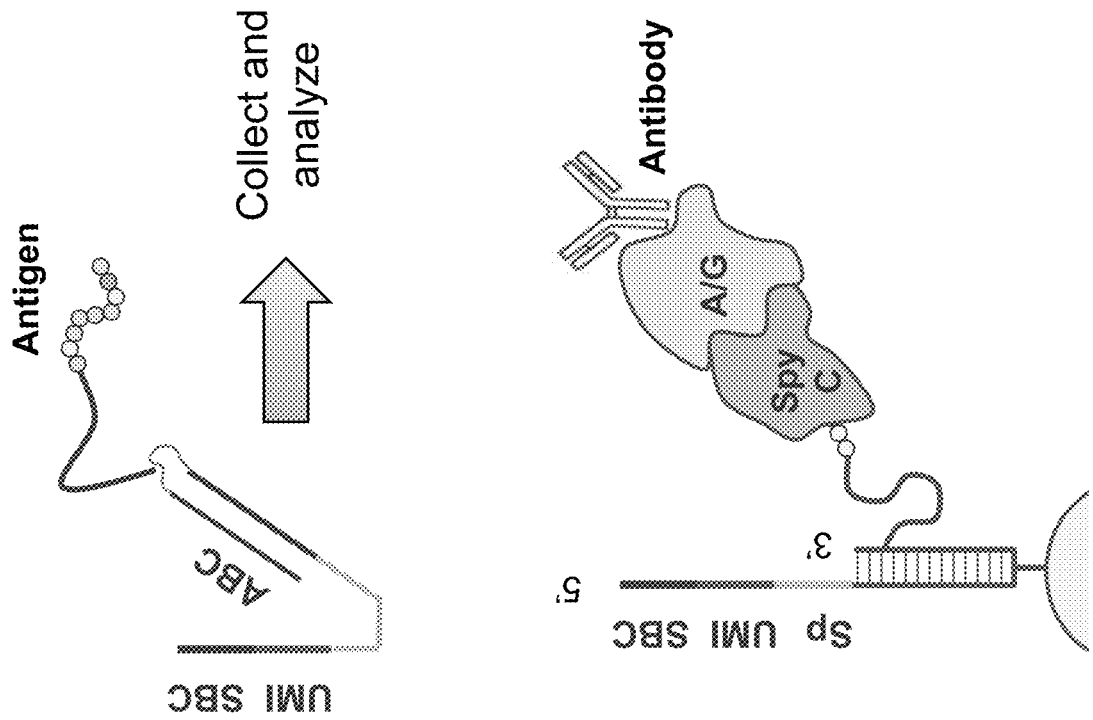
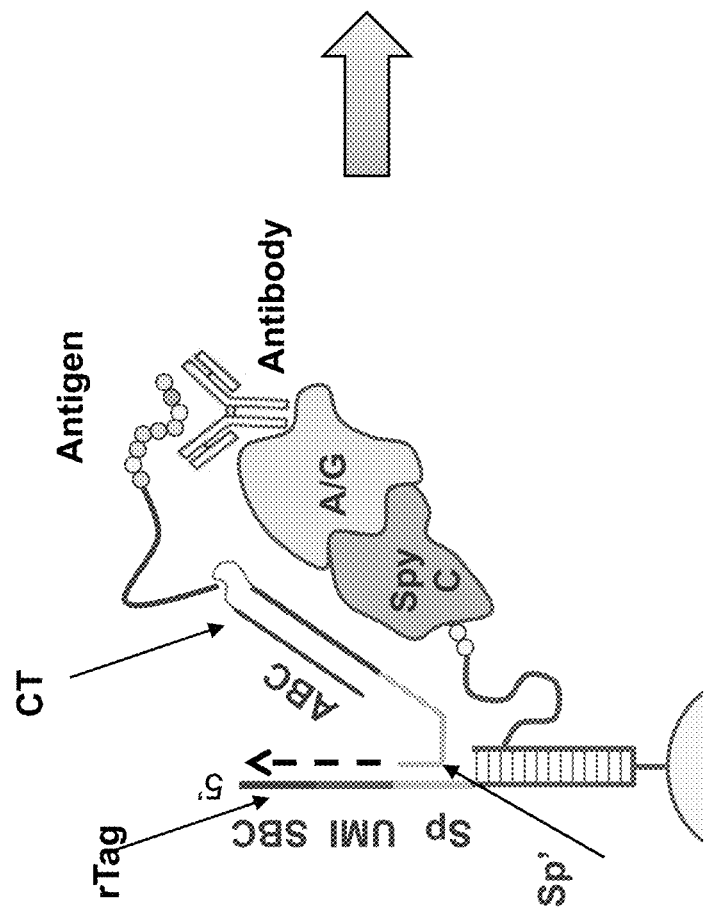
Fig. 4B

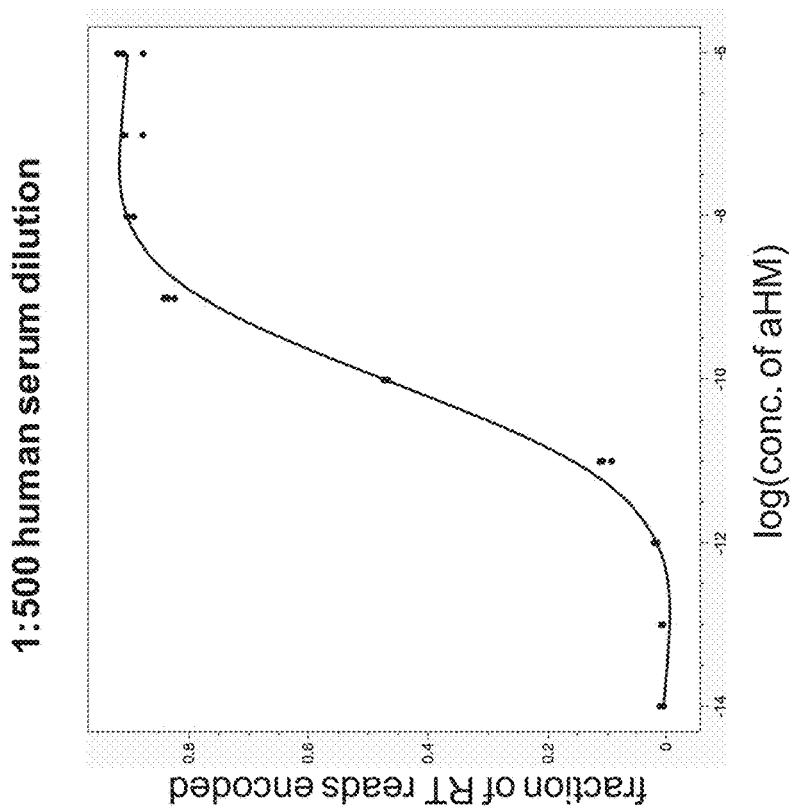
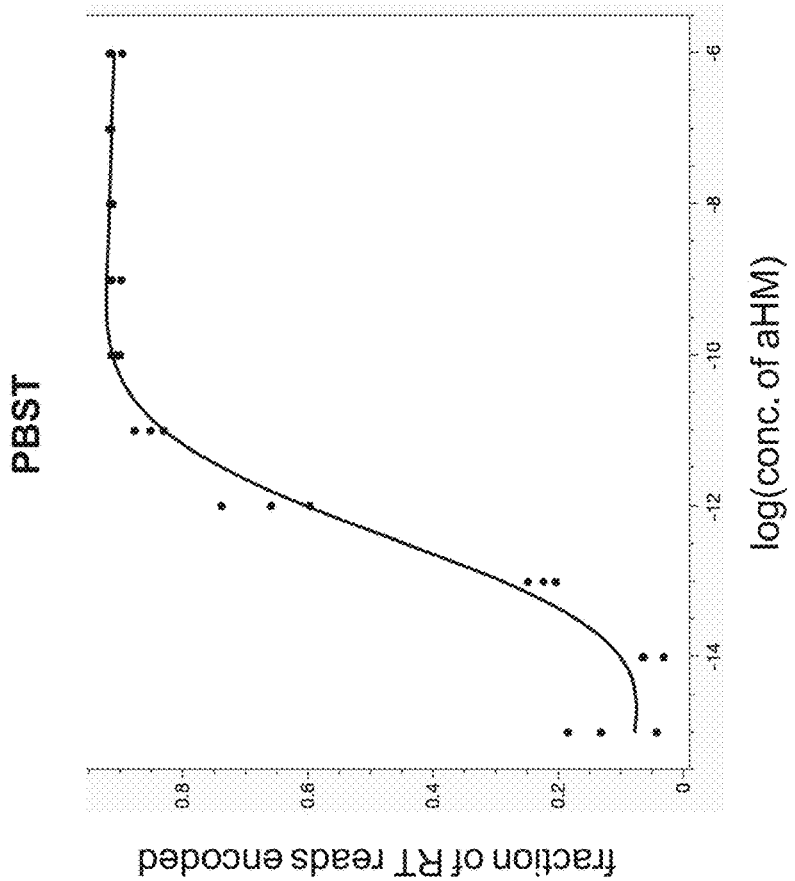
Fig. 9

HIGH-THROUGHPUT SEROTYPING AND ANTIBODY PROFILING ASSAYS

CROSS-REFERENCE TO RELATED APPLICATION

This application claims priority to U.S. Provisional Patent Application No. 63/294,374 filed Dec. 28, 2021, entitled "HIGH-THROUGHPUT SEROTYPING AND ANTIBODY PROFILING ASSAYS," which is herein incorporated by reference in its entirety for all purposes.

STATEMENT REGARDING FEDERALLY SPONSORED RESEARCH

This invention was made with government support awarded by National Cancer Institute of the National Institutes of Health under Grant No. R44CA203629. The United States Government has certain rights in this invention pursuant to this grant.

REFERENCE TO AN ELECTRONIC SEQUENCE LISTING

The contents of the electronic sequence listing (776532003500SEQLIST.xml; Size: 69,431 bytes; and Date of Creation: Dec. 22, 2022) is herein incorporated by reference in its entirety.

TECHNICAL FIELD

The present disclosure relates generally to immunology and immunoassays, in particular to high-throughput, population-wide serotyping methods and high-throughput, serotyping and antibody profiling assays.

BACKGROUND

The humoral immune response (repertoire of antibodies and B cells generated by pathogen exposure) is of primary importance in fighting infectious pathogens, and serotyping the antibodies to pathogens at a population level is critical to effectively managing a pandemic such as caused by the latest spread of COVID-19 disease. The antibody repertoire of an individual provides insight into past pathogen exposure and enables epidemiological profiling and surveillance of pathogen distribution in time and space. Current serotyping assays vary in quality and are limited in throughput which precludes collection of population-scale data in a timely manner. The importance of tracking population wide pathogen exposure is well evidenced by the recent COVID-19 pandemic. Commonly employed assays for detecting prior antigen exposure have limited throughput leading to insufficient data for population-wide assessment of COVID-19 exposure in a timely manner Rapid, broad spectrum, high-throughput, and quantitative assays with minimal sample input requirements would greatly enable population-wide studies of pathogen exposure. The present disclosure addresses these and other needs.

BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

Given the complexity of COVID-19 disease pathophysiology, and the need to develop effective vaccines, it is of utmost importance to understand the role of the humoral immune response in mediating disease immunopathology and in mediating potential side-effects of vaccination. It is well known that the humoral immune response raises both neutralizing and enhancing antibodies. The enhancing antibodies are involved in a process call "antibody-dependent enhancement" (ADE) which leads to exacerbation of the infection (Kulkarni 2019). As such, it is of critical importance to monitor the nature of the immune response induced by a vaccine candidate across a large population. A key determinant of whether and antibody is neutralizing or enhancing is related to the epitope to which it is raised (Zhang, Hu et al. 2020). Moreover, cross-reacting antibodies from immune response to related strains can also induce an ADE response. As an example, a retrospective analysis of medical records from the 1918 influenza pandemic revealed that subjects that experienced a prior influenza-like illness had increased risk of serious illness during the 1918 pandemic period (Shanks, Burroughs et al. 2016).

Numerous technologies for antibody/epitope profiling have been developed with relevance in fundamental immunology research, vaccine design, therapeutic antibody development, and autoimmune disease. High throughput and high resolution antibody/epitope screening approaches such as B cell next generation sequencing (NGS) (Robinson 2015), high-resolution mass spectrometry such as IgSeq (Lavinder, Horton et al. 2015), peptide microarrays (Andresen and Grotzinger 2009, Carmona, Nielsen et al. 2015), phage display such as VirScan (Xu, Kula et al. 2015) and PhIP-Seq (Mohan, Wansley et al. 2018), DPA (Sanchez-Lockhart, Reyes et al. 2018), and DNA-barcoded antibody assays such as ADAP (Tsai, PNAS 2018) provide fundamentally enabling technologies. Phage display technologies are particularly useful because they enable high-throughput discovery/screening in genetically tractable systems. For example, the combination of bacteriophage peptide display and affinity purification enables epitope profiling for all known human viruses in 1 µL serum samples (Xu, Kula et al. 2015). While these methods have dramatically improved our understanding of immunology and enabled antibody therapeutic discovery/development, they have yet to fully integrate into clinical diagnostic applications (Frenzel, Schirrmann et al. 2016). Technologies that enable population-wide epitope profiling and correlation with durable immunity will provide unprecedented insight into pathogen distribution, preferred immunogens for vaccine development, therapeutic efficacy, genetic predispositions and so on.

As such, the development of multiplex serotyping assays are of utmost importance in understanding immune sequela from prior infections and in demonstrating long-term safety of vaccines. Regarding the COVID-19 pandemic, there is an urgent need for large scale serology testing to better characterize the relationship between amounts and types of antibodies produced and immunity to SARS-CoV-2, whether cross-reacting antibodies from prior coronavirus infection confers immunity, whether production of certain types of antibodies contribute to antibody-dependent enhancement, and the role of humoral vs. cellular immunity in response to disease. A recent publication on epitope profiling of antibodies to SARS-COV-2 viral proteome illustrates methods of multiplexing epitope profiling via NGS monitoring of the binding of DNA-peptide antigen conjugates to immobilized human plasma antibodies (Ladner, et al. 2021. "Epitope-Resolved Profiling of the SARS-CoV-2 Antibody Response Identifies Cross-Reactivity with Endemic Human Coronaviruses." Cell Reports. Medicine 2 (1): 100189).

The present invention provides improved methods for high-throughput, comprehensive, accurate, and sero-profiling or quantitative (or semi-quantitative) sero-profiling with minimal sample input requirements. The invention is illustrated by the description, examples and figures below. To this end, various references are set forth herein which describe in more detail certain background information, procedures, compounds and/or compositions, and are each hereby incorporated by reference in their entireties.

In exemplary embodiments, provided herein are variants of a Digital Serotyping (DST) assay, which employs next generation sequencing (NGS) to measure the "serotyping profile" of barcoded subject serum antibodies tested against a range of DNA-tagged pathogen-derived antigens, addressing the need for a scalable and comprehensive population-wide serotyping and antibody profiling assay. One of the technical advantages of the disclosed DST assay is the ability to assess levels of antibodies specific to particular antigens in multiple samples simultaneously in a single assay, allowing for high-throughput multiplexing. The disclosed assay variants enable multiplexing in both the sample and antigen dimensions, generating a large multi-dimensional serotyping data set ((N samples)×(M antigens)) for more comprehensive serotyping profiling of large populations across a large number of antigens and possible various pathogens. The disclosed DST assay can be applied to screening of both antibodies and specific antigens simultaneously in multiple samples. Further, the ability to easily scale and multiplex the number of peptide epitopes allows rapid updating of the assay content to monitor the ever-changing mutation spectrum of the pathogens.

The variants of the DST assay provided herein are amenable to profile multiple antibody isotypes, including IgM, IgG, and IgA, and also amenable to multiple sample types including biological samples (serum (e.g., IgM, IgG, and IgA), saliva (IgA), other bodily fluids), as well as other samples, such as de novo synthesized antibodies and antibody mixtures. These assays are compatible with dried blood spot testing or Mitra blood collection devices (i.e., Neoteryx), as currently employed by the NIH for Covid-19 serological testing ("Serosurvey"), and enable remote sampling for improved population statistics. This technology is also applicable to applications in cancer immunology and autoimmune conditions (e.g., neoantigen or autoimmune profiling), screening for toxins, antibody therapeutics development, biosecurity, and veterinary medicine, etc. This technology can also be applied to high-throughput screening approaches during antibody discovery to select antibodies or antibody fragments capable of binding different epitopes originated from plants, animals, fungi, insects, bacteria, parasites, and so on.

Provided herein is a method for sample analysis, comprising: a) (i) separately contacting a plurality of different antibodies of each sample of a plurality of samples with a binding element configured to bind to the plurality of different antibodies in the sample, thereby obtaining binding element-antibody conjugates; and (ii) attaching either the binding element or the binding element-antibody conjugates to a bead, wherein the binding element is attached to the bead before or after contacting the plurality of different antibodies, wherein the binding element is associated with a recording tag comprising a sample-specific barcode before or after attachment to the bead, thereby obtaining a plurality of beads comprising attached binding element-antibody conjugates each associated with the recording tag from each sample; b) mixing the pluralities of beads comprising attached binding element-antibody conjugates from the plurality of samples, thereby obtaining a mixture of beads; c) contacting the mixture of beads with a binding agent comprising an antigen and a coding tag attached thereto, wherein the coding tag comprises an encoder sequence that comprises identifying information regarding the antigen; d) following binding of the antigen to an antibody attached to a bead of the mixture of beads, allowing transfer of identifying information between the coding tag and the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

Provided herein is also a method for sample analysis, comprising: a) separately contacting each sample of a plurality of samples with a plurality of beads, wherein each bead of the plurality of beads contacted with the sample comprises i) a recording tag comprising a sample-specific barcode and ii) an associated binding element configured to bind to a plurality of different antibodies in the sample, thereby obtaining a plurality of beads comprising attached binding element-antibody conjugates each associated with the recording tag from each sample; b) mixing the pluralities of beads comprising attached binding element-antibody conjugates from the plurality of samples, thereby obtaining a mixture of beads; c) contacting the mixture of beads with a binding agent comprising an antigen and a coding tag attached thereto, wherein the coding tag comprises an encoder sequence that comprises identifying information regarding the antigen; d) following binding of the antigen to an antibody attached on a bead of the mixture of beads, allowing transfer of identifying information between the coding tag and the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

Provided herein is also a method for sample analysis, comprising: a) separately contacting each sample of a plurality of samples with i) a nucleic acid tag comprising a sample-specific barcode, and ii) a binding element configured to bind to a plurality of different antibodies in the sample, thereby obtaining a plurality of nucleic acid-bound antibody-binding agent complexes from each sample; b) mixing the pluralities of nucleic acid-bound antibody-binding agent complexes from the plurality of samples and attaching them on a plurality of beads, wherein the plurality of beads optionally comprises a plurality of nucleic acid recording tags, thereby obtaining a mixture of beads comprising a plurality of attached antibodies each associated with a nucleic acid tag or recording tag; c) contacting the mixture of beads with a binding agent comprising an antigen and a coding tag attached thereto, wherein the coding tag comprises an encoder sequence that comprises identifying information regarding the antigen; d) following binding of the antigen to an antibody attached on a bead of the mixture of beads, allowing transfer of identifying information between the coding tag and the nucleic acid tag or the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

In any of the embodiments herein, the plurality of different antibodies of the same sample can have different antigen-binding sites. In some embodiments, at least two or more (e.g., all) of the different antibodies from the same sample can have different antigen-binding specificities. In some embodiments, the plurality of different antibodies of the same sample are different antibodies in that they have different antigen-binding specificities, whereas the plurality of different antibodies can share the same antibody constant region (or similar antibody constant regions), e.g., the same Fc region (or similar Fc regions), such that the plurality of different antibodies can be bound by the same binding element on a bead. For instance, each different antibody from the same sample can bind to a different epitope. In some embodiments, each different antibody from the same sample can bind to a different antigen. In any of the embodiments herein, different antibodies specific for different epitopes and/or different antigens can be bound to the same binding element on the same bead or on beads having the same sample-specific barcode, thereby allowing efficient, high throughput antibody assays such as serotyping in biological samples.

BRIEF DESCRIPTION OF THE DRAWINGS

Non-limiting embodiments of the present invention will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the invention.

FIG. 1 depicts an exemplary protein assay using one or more binding agents specific for particular component(s) of the immobilized polypeptide and comprising coding tag(s) comprising an encoder sequence that that comprises identifying information regarding the binding agent(s). Step 1 comprises immobilizing a polypeptide with associated recording tag that comprises a sample-specific barcode to a support (e.g., a bead or a sequencing substrate such as a flowcell). Step 2 comprises binding of a binding agent (antibody, Ab) conjugated with a coding tag that comprises an encoder sequence with identifying information regarding the corresponding binding agent (Ab1, Ab2, etc.). Step 3 comprises transferring the encoder sequence or a complement thereof from the coding tag to the recording tag, creating an extended recording tag (encoding step). Alternatively, at step 3 the encoder sequence or a complement thereof can be transferred from the recording tag to the coding tag, creating an extended coding tag (encoding step). In both embodiments, the transfer occurs through a primer extension reaction or ligation. Steps 2-3 form encoding cycle during which the identifying information of the binding agent is encoded in the polypeptide-associated extended recording or coding tag. One or several encoding cycles can be employed during the assay (cyclic binding of cognate binding agents to the immobilized polypeptide and corresponding information transfer after binding). After a series of sequential binding and coding tag information transfer steps, the final extended recording tag is produced, containing binding agent coding tag information including barcodes from "n" binding cycles providing identifying information for the binding agents (e.g., antibody 1 (Ab1), antibody 2 (Ab2), antibody 3 (Ab3), . . . antibody "n" (Abn)), a sample-specific barcode sequence from the recording tag, and flanking universal priming sequences at each end of the library construct to facilitate amplification and analysis by digital next-generation sequencing (NGS). The transfer of the identifying information (e.g., the encoder sequence or the complement thereof) from the recording tag to the coding tag typically occurs only once (n=1), and binding agent comprising extended coding tags are collected and analyzed. The exemplary assays described in FIG. 1 can be referred to as next generation protein assay (NGPA).

FIG. 2A. During DST assay, antibody molecules each associated with rTag are attached to a support (e.g., a bead) and contacted with a solution comprising cTag-antigen conjugates. The antigen interacts with the cognate immobilized antibody, bringing rTag and cTag into proximity SBC—sample-specific barcode, and the rTag can optionally comprise one or more other barcodes, such as a fraction barcode, a spatial barcode, a compartment tag, etc.; Antigen BC—antigen barcode; UMI-optional unique molecular identifier (may be present in recording tag and/or coding tag); Sp and Sp'—complementary spacer regions; P1 and P2—optional primer sites used for amplification of the recording tag extended after information transfer. FIG. 2B. Transfer of the identifying information (e.g., encoder sequences such as barcodes and/or UMI). Following binding of the antigen to the cognate immobilized antibody, a primer extension step is performed to transfer the identifying information regarding the antigen (e.g., an antigen barcode) from cTag to rTag, generating extended recording tag associated with the antibody and comprising a portion complementary to the antigen barcode. Alternatively, following binding of the antigen to the cognate immobilized antibody, a primer extension step is performed to transfer information regarding the antibody (e.g., the sample-specific barcode) from rTag to cTag, generating an extended coding tag associated with the antigen and comprising a portion complementary to the UMI present in the recording tag and to the sample-specific barcode. FIG. 2C. Analysis of the extended recording tag or extended coding tag by NGS reveals identity of the antigen and/or identity of the immobilized Ab, as well as identity of the biological sample, thereby assessing levels of specific antibodies (e.g., for particular antigens and/or epitopes thereof) in multiple samples collected from the subject(s).

FIG. 3. Exemplary design of DNA-barcoded antibody capture beads (DST beads). Capture hairpin DNA comprising recording tag with sample-specific barcode (SBC) and spacer region (Sp) is attached to the bead. A binding element such as Protein A/G is covalently coupled via a linker to the capture DNA on the bead and is used to capture an antibody from a sample. In some samples, the binding element is configured to bind to an antibody constant region (e.g., Fc of IgG, IgA, IgD, IgM, or IgE) and is not configured to bind to an antibody variable region (e.g., the antigen binding sites). Thus, the antigen binding sites of the captured antibody are available to bind specifically to a cognate antigen.

FIG. 4B. Exemplary output of the DST assay. An antibody from a biological sample is captured on the bead as described in FIG. 4A. The DST bead comprises a recording tag comprising a sample-specific barcode (SBC), a UMI and spacer region (Sp). The DST beads with the captured antibody is contacted with one or more antigens, wherein each antigen is attached to a coding tag (cTag) comprising identifying information regarding the antigen (antigen barcode, or ABC) and a complementary spacer region (Sp'). Following binding of the antigen to the cognate immobilized antibody, a primer extension step is performed to transfer the identifying information regarding the antibody (UMI) and the sample (sample-specific barcode, or SBC) from rTag to CT, generating an extended coding tag associated with the antigen and comprising a portion complementary to the UMI present in the recording tag and to the sample-specific barcode. After transfer, the one or more antigens with attached extended coding tags are collected and analyzed by sequencing. Analysis of the extended coding tags by NGS can reveal identity of the antigen and/or identity of the immobilized Ab, as well as identity of the biological sample, thereby assessing levels of specific antibodies in multiple samples collected from the subject(s).

FIG. 5A. Using the orthogonal SpyT-SpyC and SnpT-SnpC bioconjugation systems to develop immunoglobulin binding beads. A SpyCatcher-SnoopCatcher (SpyC-SnpC) fusion protein is used to bridge a SpyTag (SpyT) peptide (13 amino acids) attached to capture hairpin DNA comprising recording tag with sample-specific barcode (SBC) and spacer region (Sp) to a SnoopTag (SnpT) peptide fused to a synthetic Z domain peptide (or optionally C2 or HTB1 domain peptide). The synthetic Z peptide contains a photoaffinity moiety (such as benzophenone, BP) for optional photo-induced cross-linking to an antibody molecule after the antibody molecule is captured by binding to the Z peptide. Incubation of the DST beads with a serum sample leads to capture and covalent immobilization (i.e., attachment) of IgG antibodies on the surface of the beads. FIG. 5B. Antibodies are derivatized in solution using the Z domain (Protein A subdomain) or C2 domain (Protein G subdomain), which bind and photoaffinity couple to immunoglobulin molecules. The IgG antibody Z and C2 binding sites are highlighted in circles. The C2 and Z domains are decorated with a photoaffinity agent (BP) and a SpyTag peptide (alternatively, SnoopTag). Binding and subsequent photoaffinity coupling to IgG effectively covalently conjugate the SpyTag to the antibody. The antibody conjugates are subsequently attached to SpyCatcher DST beads for the DST assay. Figure adapted from Kanje S, et al., "Next generation of labeling reagents for quantitative and multiplexing immunoassays by the use of LA-ICP-MS." Analyst (2016), 141(23): 6374-6380.

FIG. 7A. Serum antibody capture and sample barcoding occur on the DST beads. DNA barcoded Protein A/G beads are generated to capture and barcode IgG/IgM/IgA derived from serum samples. Serum antibodies are attached to the barcoded DST beads, washed to remove background serum components, and beads pooled into a single well on a multi-well assay filter plate. Sample pooling enables high-throughput serology. An entire sample plate can be collapsed into a single well on the encoding-based DST assay filter plate enabling up to 384×384=150 k samples to be processed per 384-well assay plate. A solid-phase immunoassay is performed such that positive antigen-antibody interactions are recorded as extended recording tag libraries. Further analysis by NGS enables deconvolution of antibody-antigen interactions for individual serum samples. FIG. 7B shows an exemplary encoding process (similar to FIGS. 2A-2B), which translates specific antibody-antigen binding interactions into nucleic acid libraries that comprise recording tags extended during the encoding step.

FIG. 9. Exemplary limit of detection (LOD) estimation for the DST assay. An antibody targeting the HM-epitope tag was diluted with either PBS-T buffer (left graph) or diluted human serum (1:500 dilution in PBS-T, right graph) to assess the antibody detection limit in different matrices. Resulting samples were exposed to DST beads having recording tags attached to immobilize antibodies, and were subsequently washed to remove excess and non-specifically bound material. For the DST assay, antibodies attached to the beads were incubated with 0.5 nM of coding tag-barcoded HM peptides; then, beads were washed with PBS-T twice to remove unbound material. Encoding reactions were performed to register the antibody-epitope binding interaction, indicated by transfer of coding tag information onto corresponding recording tags, generating extended recording tags. Then, beads were subjected to an additional DNA "capping" process to append PCR primer sequences to extended recording tags. Finally, the recording tags further extended after the capping step were amplified by PCR using the appended PCR primers, and the resulting PCR products were analyzed by next-generation sequencing (NGS) using an Illumina MiSeq; DNA sequences were processed to determine the identity and number of recording tags having specific DNA recording tag/coding tag combinations. Experiments were performed in triplicate. Detection limits of 1 pM and 10 pM (signal-to-noise=3) were observed in PBS-T and diluted human serum, respectively.

A total of 52 Cov2-positive and 11 negative samples were analyzed. Pooled results were essentially identical to the individual encoding results. Thus, no evidence of significant crosstalk between samples during multiplexing was observed. Difference in sample-to-sample encoding rates may reflect existing biological variance.

Only very limited crosstalk was observed between samples, as assessed by relative encoding signal between combined and individual samples. In this context, crosstalk may result from transfer of antibodies from one DST bead to another, resulting in measurable signal on barcoded DST beads that was not observed in the individually analyzed samples. No significant crosstalk is observed in the combined samples, demonstrating that sample multiplexing yields high fidelity measurement of antibody-antigen interactions.

Figure 14:
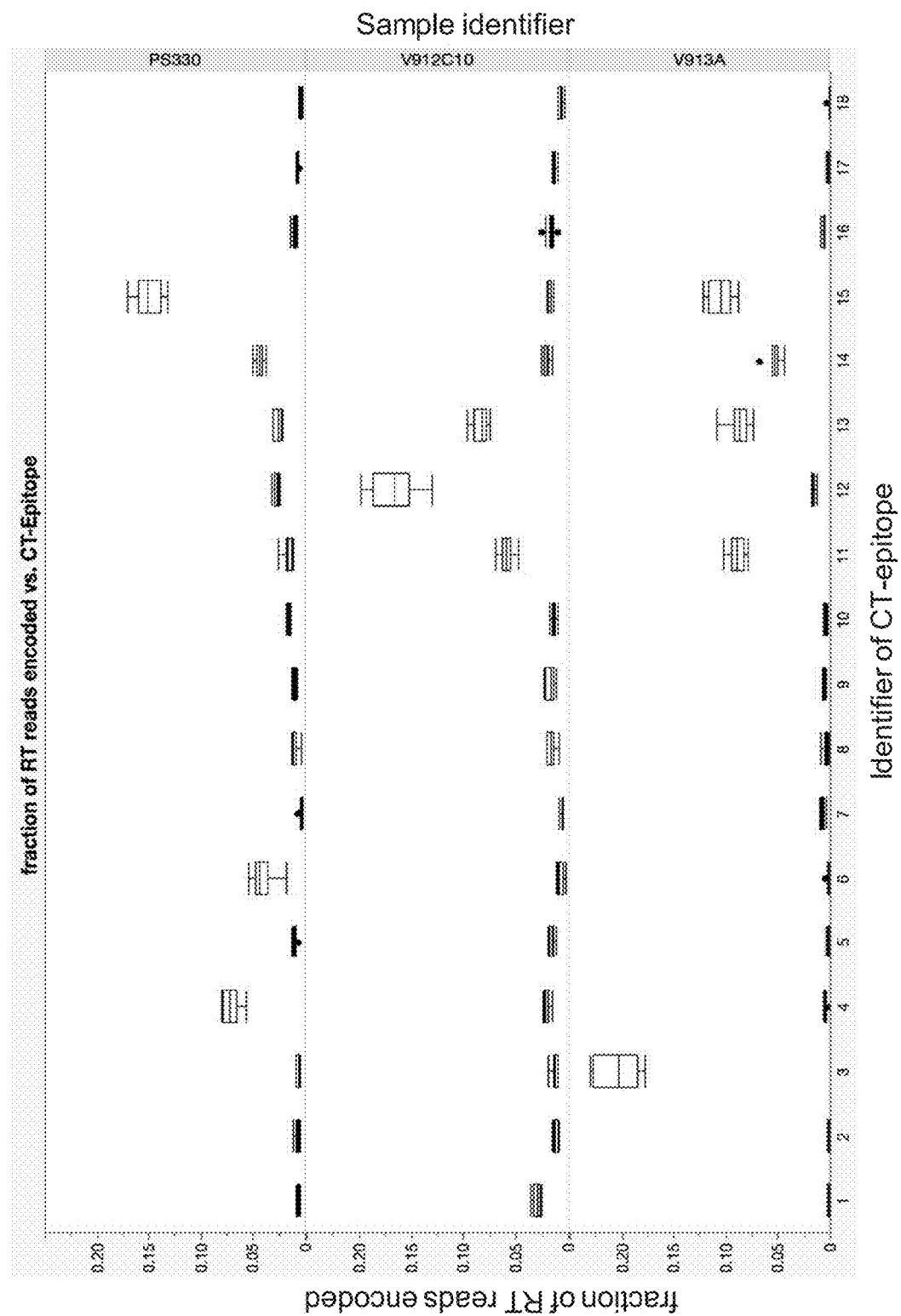

FIG. 14. Exemplary DST assay reproducibility as assessed by sample multiplexing. Individual serum samples (PS330, V912C10, and V913A) were distributed across multiple unique recording tags (SB03, SB09, etc.). Encoding assays were performed separately on the three pooled barcode sets. Data are presented as quantile box-plots. Description of peptide epitopes used in this experiment is provided in Table 1.

Figure 15A:
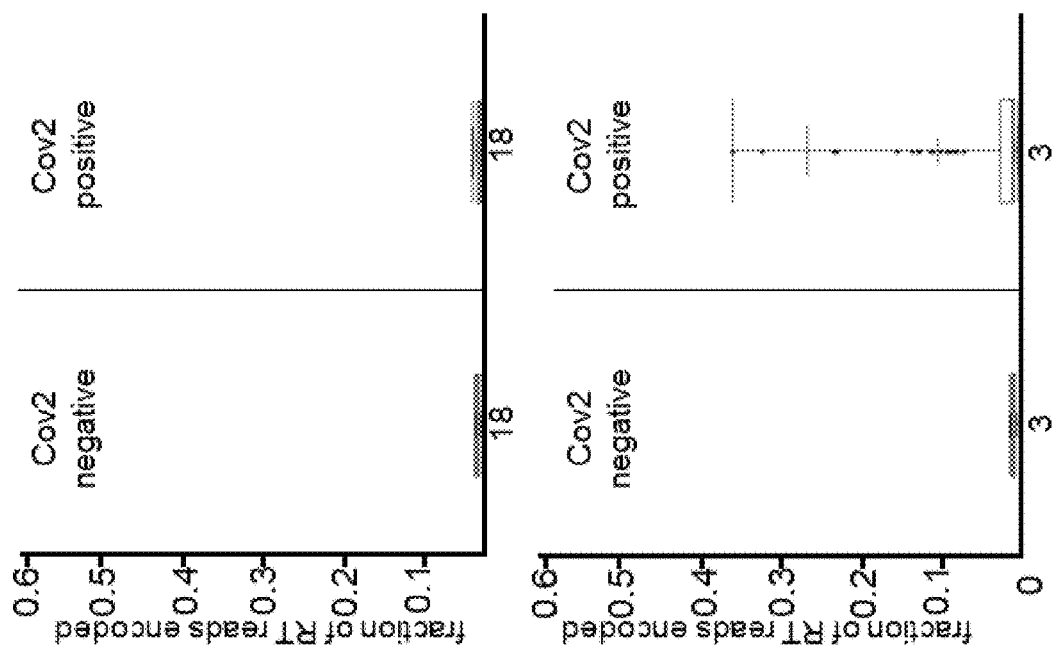
Figure 15B:
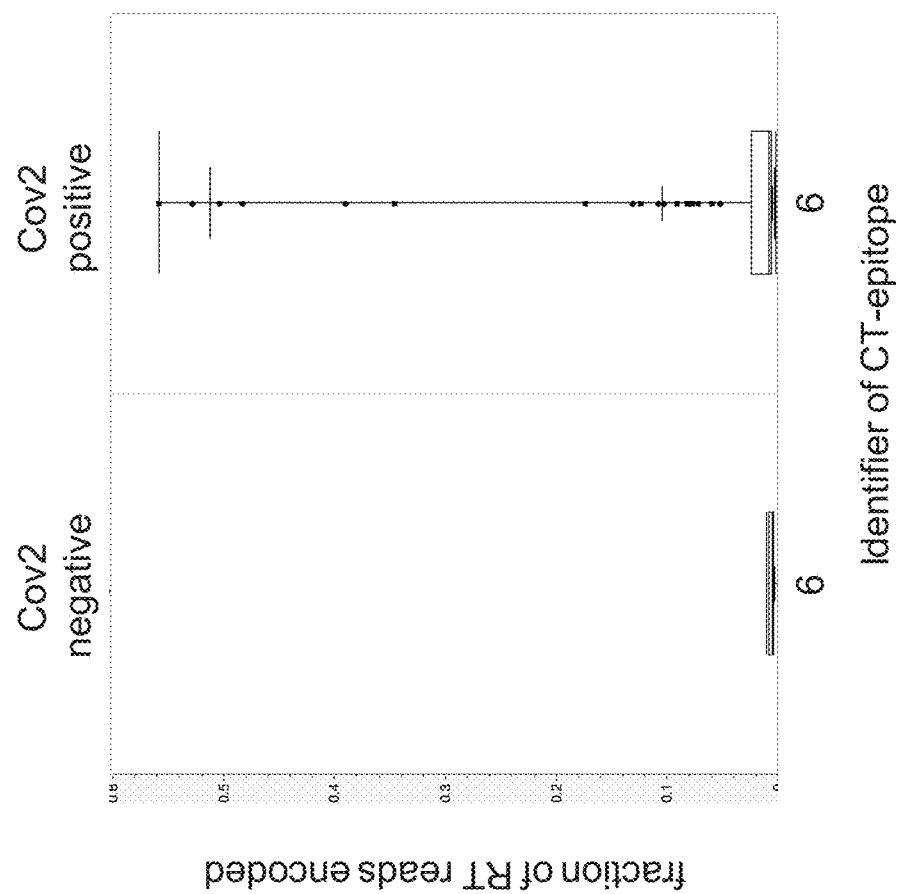

FIGS. 15A-15B. Exemplary detection of COVID-19 antibodies in response to viral infection. Description of peptide epitopes used in this experiment is provided in Table 1. Negative control (scrambled peptide; FIG. 15A, upper panel), spike (FIG. 15A, bottom panel) and nucleocapsid (FIG. 15B) epitopes were evaluated across 52 COVID-19 positive and 11 negative control serum samples in the DST assay with the CT-epitopes. Data are presented as quantile box-plots.

Three representative encoding results are shown: Upper panel of FIG. 15A from a scrambled peptide (random sequence) as a negative control; bottom panel of FIG. 15A from a spike protein peptide; FIG. 15B from a nucleocapsid protein. Encoding reactions were performed as described in Example 7. Signals from two representative epitopes were increased from only the positive samples. There was no difference from the negative control peptide.

Figure 16:
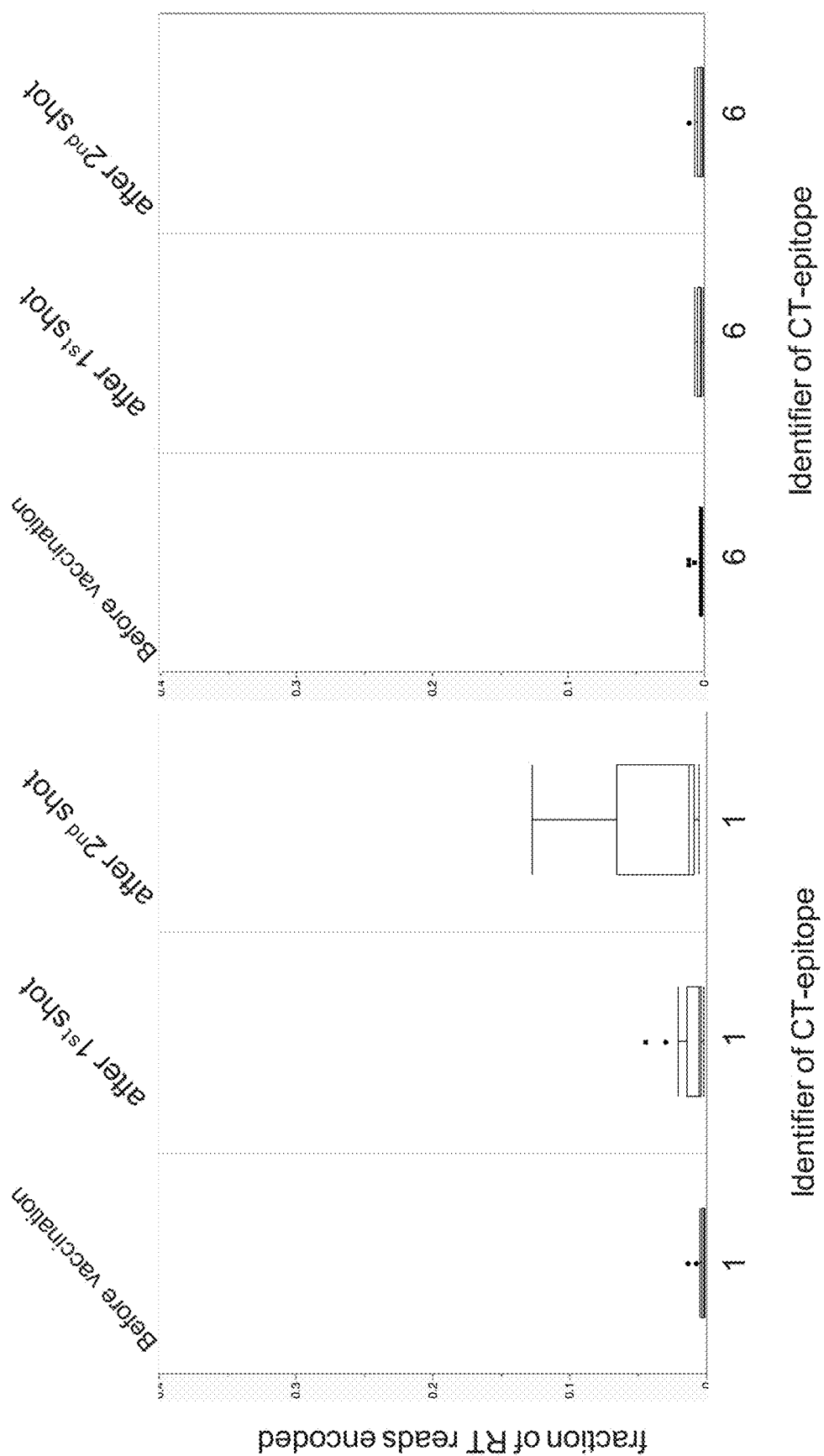

FIG. 16. Vaccination time course. Exemplary detection of COVID-19 antibodies in response to vaccination. Sera were collected roughly one week after the first and second dose. Description of peptide epitopes used in this experiment is provided in Table 1. Spike epitope (left panel, epitope 1) and nucleocapsid epitope (right panel, epitope 6) were used in the DST assay across 11 donors. Data are presented as quantile box-plots. Only the spike epitope produce signals in the DST assay, demonstrating the presence of anti-spike antibodies in serum samples after vaccination.

Figure 17A:
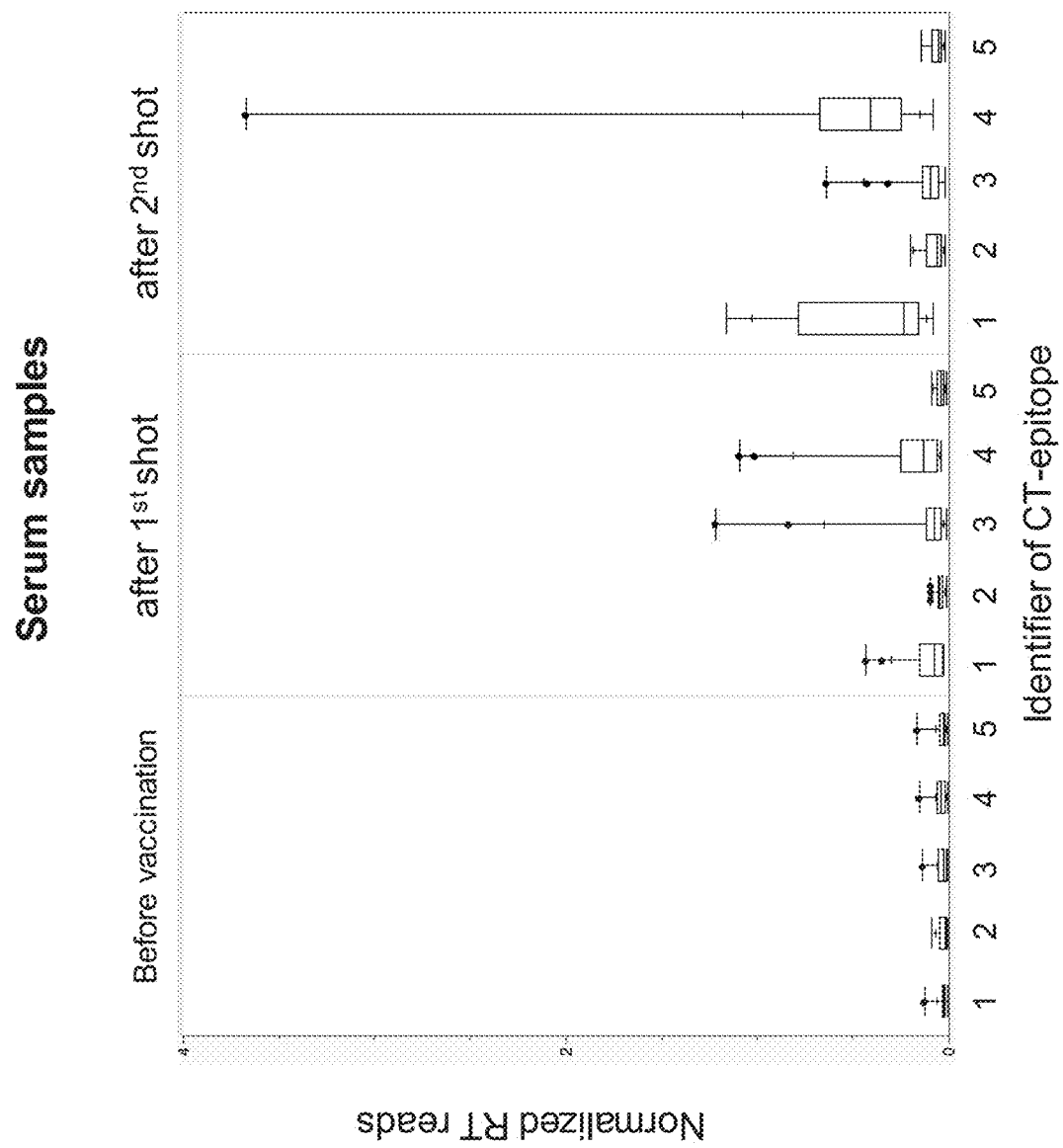
Figure 17B:
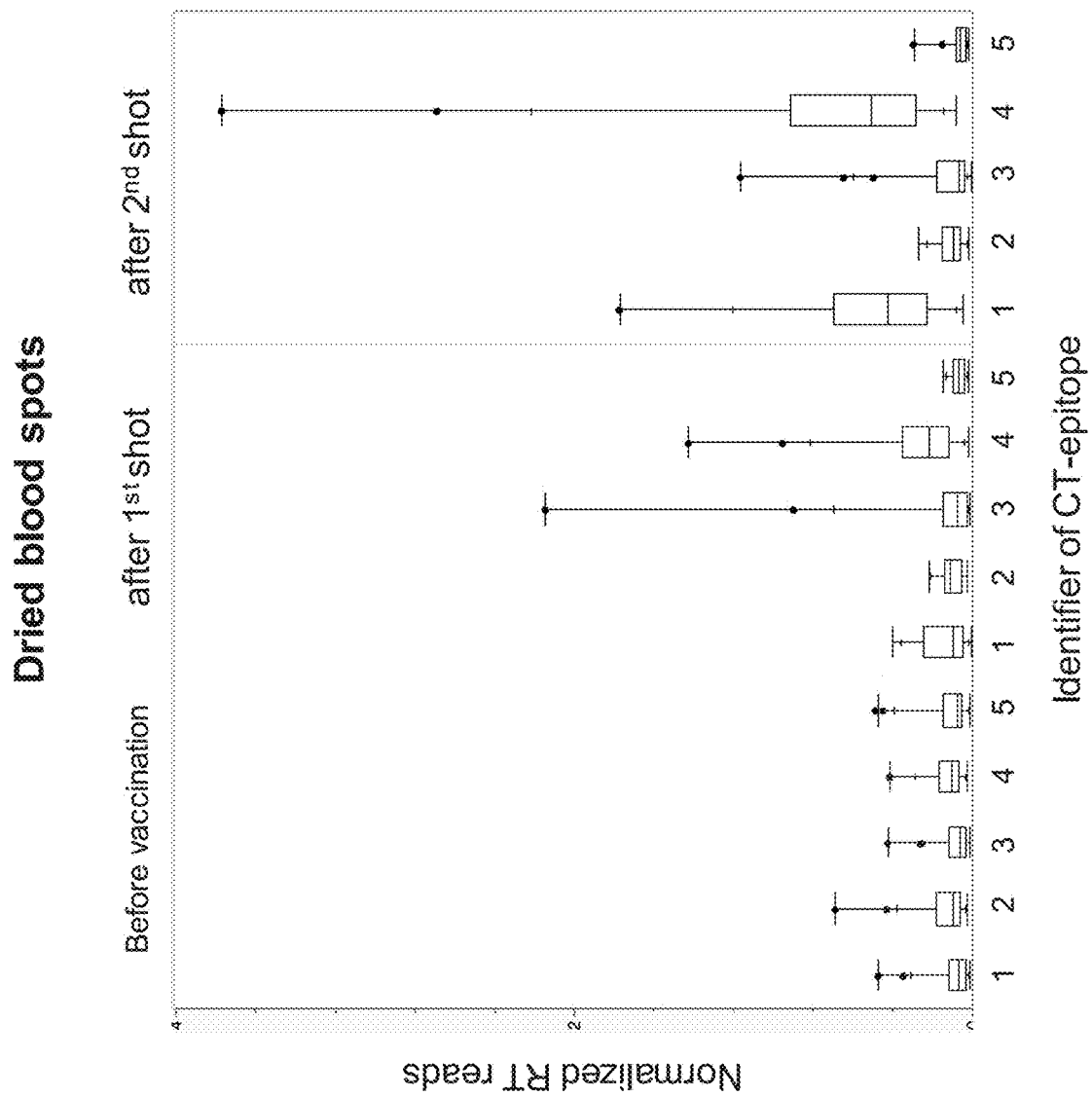

FIGS. 17A-17B. Exemplary evaluation of serum-matched dried blood spot samples corresponding to the vaccination time-course samples. Similar encoding signals can be obtained in the DST assay when utilizing serum samples (FIG. 17A) or corresponding dried blood spot samples (FIG. 17B). Description of peptide epitopes used in this experiment is provided in Table 1.

Figure 18:
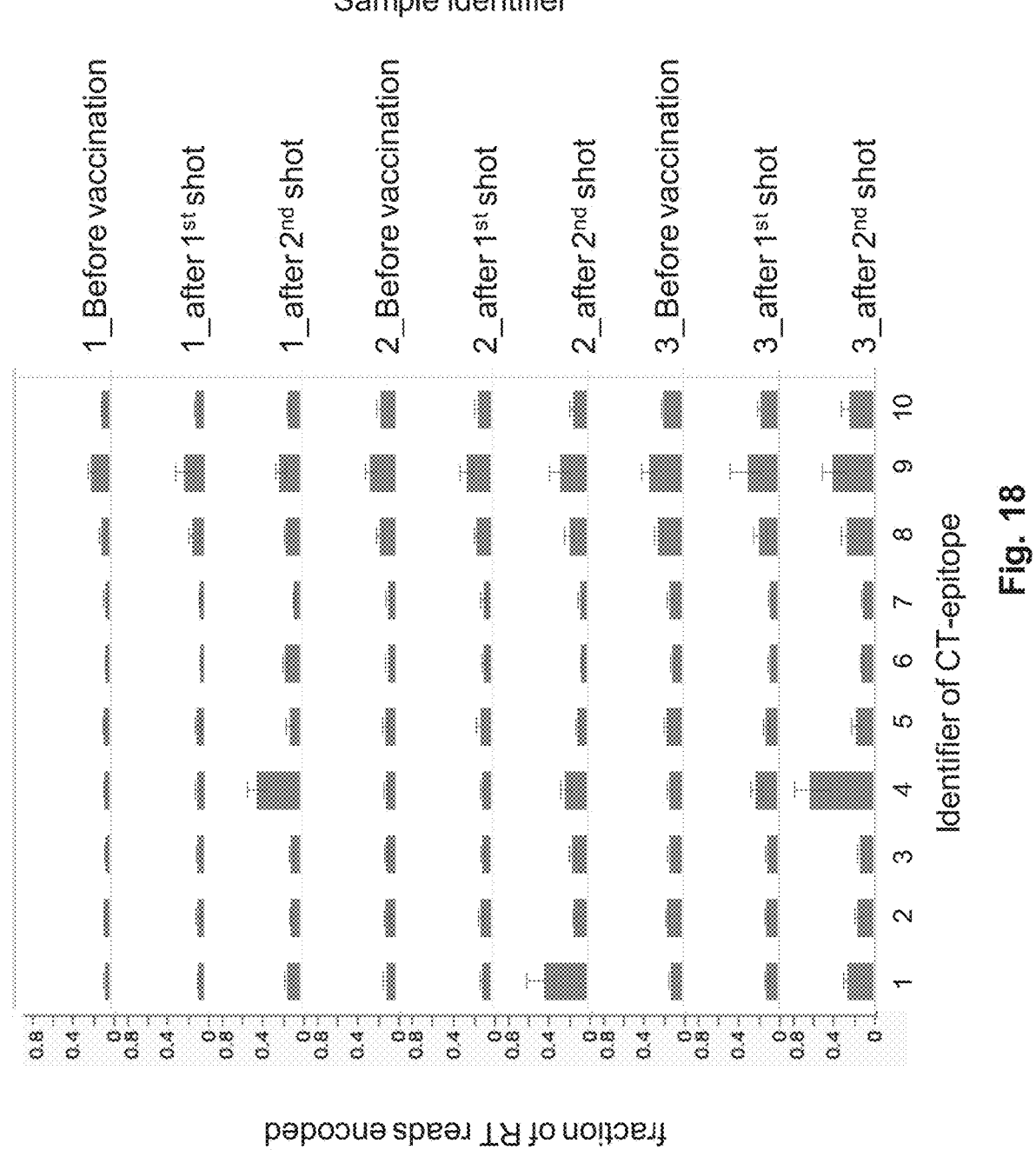

FIG. 18. Exemplary multiplexed encoding. Nine serum samples were analyzed in the automated instrument performing the DST assay and manually in filter plate (data not shown) to compare the reproducibility of the instrument. The experiments in the automated instrument were performed as a quadruplet (4 different cartridges) to ensure the reproducibility. Description of peptide epitopes used in this experiment is provided in Table 1. Samples from 3 different subjects (and 3 samples per each subject) were analyzed, showing reproducible results.

Figure 19A:
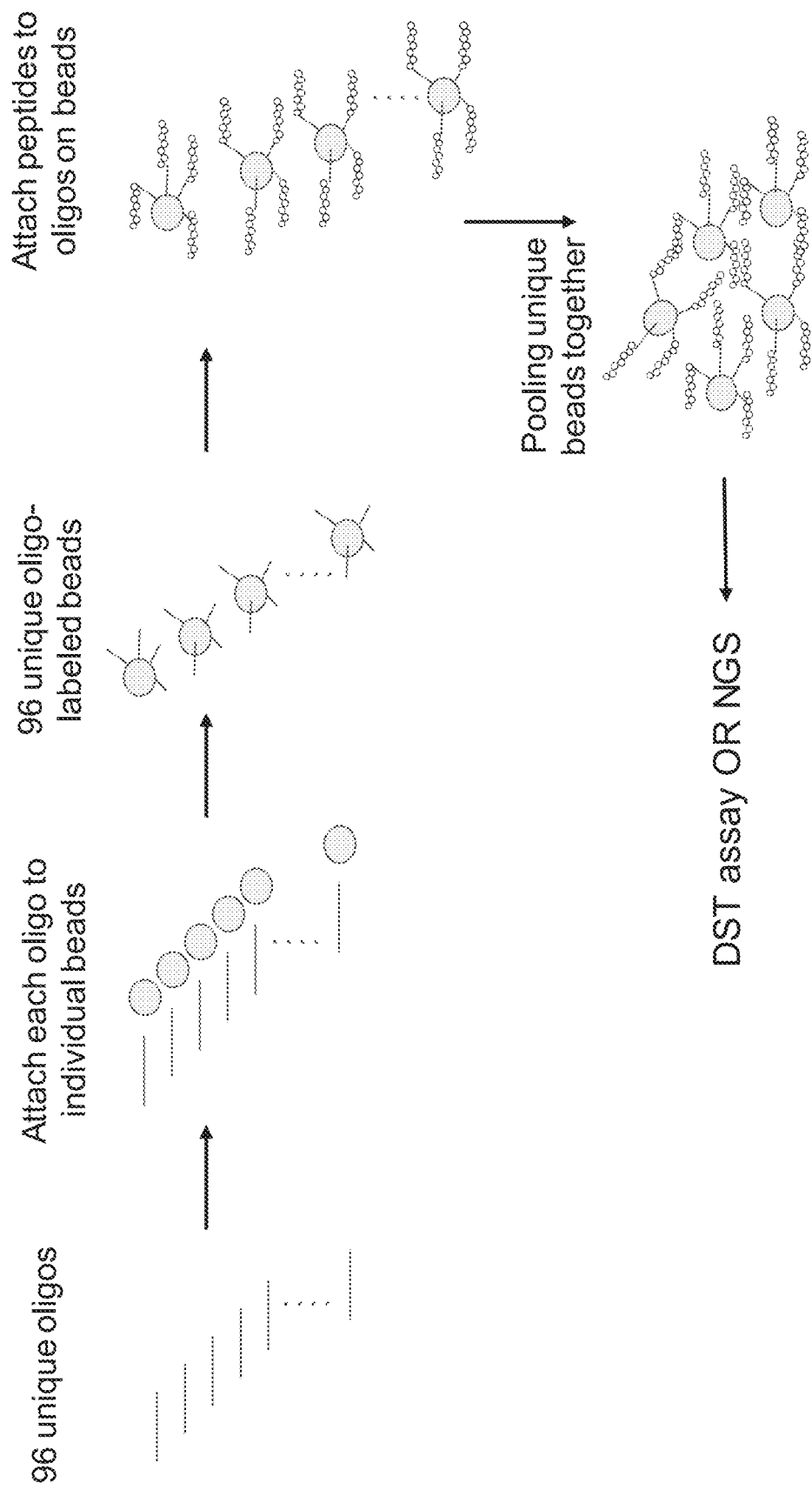
Figure 19B:
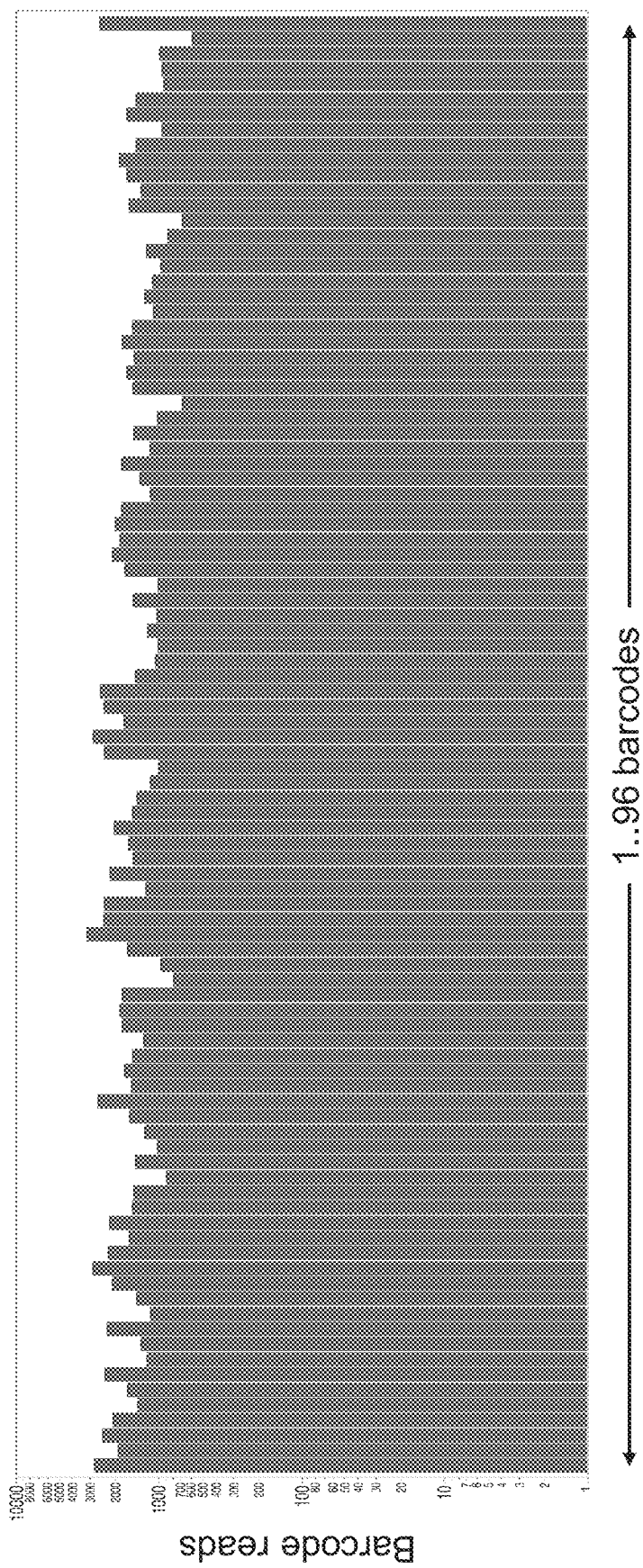

FIGS. 19A-19B. Exemplary multiplexing of 96 samples in a single assay. FIG. 19A shows assay design. 96 unique oligonucleotides representing 96 unique sample-specific barcodes were immobilized on beads, followed by attachment of peptides, generating oligonucleotide-peptide conjugates. Then, 96 unique oligonucleotide-labeled pluralities of beads were pooled together and assayed simultaneously. FIG. 19B shows successful detection of each of 96 unique barcode sequences by NGS.

DETAILED DESCRIPTION

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference.

Definitions

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

As used herein, the singular forms "a," "an" and "the" include plural referents unless the context clearly dictates otherwise. Thus, for example, reference to "a peptide" includes one or more peptides, or mixtures of peptides. Also, and unless specifically stated or obvious from context, as used herein, the term "or" is understood to be inclusive and covers both "or" and "and".

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The term "subject" includes a mammal Mammals include, but are not limited to, domesticated animals (e.g., cows, sheep, cats, dogs, and horses), primates (e.g., humans and non-human primates such as monkeys), rabbits, and rodents (e.g., mice and rats). A "subject" may include birds such as chickens or undomesticated birds. In certain embodiments, the subject is a human.

As used herein, the term "antibody" refers to an immunoglobulin (Ig) molecule or to its antigen-binding fragment (portion) that is a protein present in a sample, e.g., a bodily fluid of a subject. Antibodies may be naturally produced in response to a specific antigen or may be synthetically created by biotechnology methods (e.g., recombinantly produced in a host cell). The term encompasses all intact (full-length) or truncated immunoglobulins present in a subject or in a sample, including immunoglobulins of any class or sub-class, including IgG and sub-classes thereof, IgM, IgE, IgA, and IgD, and antigen-binding fragments thereof. Examples of bodily fluids include blood and saliva. In some embodiments, the term "antibody" may encompass heavy-chain-only antibodies, such as camelid antibodies. An antibody may comprise a "constant region" or "constant domain", which is the part of the polypeptide chain of a light or heavy chain of an antibody that is not directly involved in the antigen binding and is relatively constant in its amino acid sequence between antibody molecules that bind to different antigens. In contrast, "variable region" of an antibody is directly involved in the antigen binding and is different between antibody molecules that bind to different antigens.

As used herein, the term "non-cognate antibody" refers to an antibody that is not capable of binding or binds with low affinity to an antigen as compared to a "cognate antibody", which binds with high affinity to the corresponding antigen. In the context of the disclosed DST assay, for a particular antigen A attached to a coding tag, antibodies non-cognate for antigen A are those that bind with low affinity or not at all to the antigen A, such that such binding does not efficiently support transfer of the coding tag information to the recording tag associated with the antibody under the provided assay conditions. In contrast, binding between antibody cognate for antigen A and antigen A will efficiently support transfer of the coding tag information to the recording tag associated with the antibody under the provided assay conditions.

The term "epitope" is used to refer to an antigenic determinant (antibody binding site). An epitope is any antigenic determinant on an antigen to which an antibody binds. In some embodiments, an antibody binds to a particular epitope based on the 3D structure of the antibody and the cognate (matching) 3D structure of the epitope. Preferably, an epitope comprises a peptide; a linear epitope is formed contiguous amino acid residues, and conformational epitope is formed by the interaction of discontinuous amino acid residues.

The term "antigen" is used to refer to a substance that is specifically recognized by antibodies induced by a humoral or cellular immune response, or that can be bound by preformed antibodies. As used herein, antigen may or may not induce a specific humoral or cellular immune response (may or may not be immunogenic by itself). Antigen may be a part of a larger, immunogenic substance. Antigens can comprise polypeptide(s), lipid(s), carbohydrate(s), nucleic acid(s), fragment(s) of pathogen(s), or small molecule(s). Antigens comprise one or more epitopes recognized by antibodies. An antigen can comprise a single epitope, different independent epitopes, or multiple copies of a single epitope.

The term "neoantigen" is used to refer to a newly formed antigen that has not been previously recognized by the immune system. Neoantigens are often found in oncogenic cells and can be produced via accumulation of mutations and/or abnormal posttranslational modifications that occur in tumor cells.

As used herein, the term "sample" refers to anything which may contain an analyte for which an analyte assay is desired. As used herein, a "sample" can be a solution, a suspension, liquid, powder, a paste, aqueous, non-aqueous or any combination thereof. In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a subject, which comprises an antibody. The biological sample can be a sample obtained directly from a subject or a sample that is processed. For example, blood from a subject can be processed to yield plasma or serum comprising antibodies, which constitutes a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, from a connective, epithelium, muscle or nerve tissue.

As used herein, the terms "subject" and "patient" refer to a mammal, preferably a human.

The terms "level" or "levels" are used to refer to the presence and/or amount of a analyte, e.g., an antibody or a substance that is part of the etiology of a disease, and can be assessed, estimated or determined either qualitatively or quantitatively. A "qualitative" change in the analyte (antibody) level refers to the appearance or disappearance of an analyte that is not detectable or is present in samples obtained from controls. A "quantitative" change in the levels of one or more analytes refers to a measurable increase or decrease in the analyte levels when compared to a control. In some embodiments, assessing level of an antibody comprises determining or estimating quantity of the antibody present in a sample.

As used herein, the term "polypeptide" is used interchangeably with the term "peptide", and encompasses peptides and proteins, and refers to a molecule comprising a chain of two or more amino acids joined by peptide bonds. In some embodiments, a polypeptide comprises 2 to 50 amino acids. In some embodiments, a peptide does not comprise a secondary, tertiary, or higher structure. In some embodiments, the polypeptide is a protein. In some embodiments, a protein comprises 30 or more amino acids, or having more than 50 amino acids. In some embodiments, in addition to a primary structure, a protein comprises a secondary, tertiary, or higher structure. The amino acids of the polypeptides are most typically L-amino acids, but may also be D-amino acids, modified amino acids, amino acid analogs, amino acid mimetics, or any combination thereof. Polypeptides may be naturally occurring, synthetically produced, or recombinantly expressed. Polypeptides may be synthetically produced, isolated, recombinantly expressed, or be produced by a combination of methodologies as described above. Polypeptides may also comprise additional groups modifying the amino acid chain, for example, functional groups added via post-translational modification. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term "amino acid" refers to an organic compound comprising an amine group, a carboxylic acid group, and a side-chain specific to each amino acid, which serve as a monomeric subunit of a polypeptide. An amino acid includes the 20 standard, naturally occurring or canonical amino acids as well as non-standard amino acids. The standard, naturally-occurring (or natural) amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, β-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids. The term "amino acid residue" refers to an amino acid incorporated into a polypeptide that forms peptide bond(s) with neighboring amino acid(s).

As used herein, the term "post-translational modification" refers to modifications that occur on a polypeptide after its translation, e.g., translation by ribosomes, is complete. A post-translational modification may be a covalent chemical modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristoylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a polypeptide. The term post-translational modification can also include peptide modifications that include one or more detectable labels.

As used herein, the term "detectable label" refers to a substance or moiety which can indicate the presence of another substance when associated with it. The detectable label can be a substance that is linked to or incorporated into the substance to be detected. In some embodiments, a detectable label is suitable for allowing for detection and also quantification, for example, a detectable label that emitting a detectable and measurable signal. Detectable labels include any labels that can be utilized and are compatible with the provided binding assay format and include, but not limited to, a bioluminescent label, a biotin/avidin label, a chemiluminescent label, a chromophore, a coenzyme, a dye, an electro-active group, an electrochemiluminescent label, an enzymatic label (e.g., alkaline phosphatase, luciferase or horseradish peroxidase), a fluorescent label, a latex particle, a magnetic particle, a metal, a metal chelate, a phosphorescent dye, a protein label, a radioactive element or moiety, and a stable radical.

As used herein, the term "binding agent" refers to a nucleic acid molecule, a polypeptide, a polysaccharide, a small molecule, or a combination thereof, that binds to, associates, unites with, recognizes, or combines with a binding target. A binding agent may be a naturally occurring, synthetically produced, or recombinantly expressed molecule. A binding agent can be a binding partner, such as an antigen that interacts with an antibody, which represents a binding target. A binding agent may exhibit less selective binding, where the binding agent is capable of binding or configured to bind to a plurality of antibodies. A binding agent may comprise a coding tag, which may be joined to the binding agent by a linker.

The term "specific binding" as used herein generally refers to an binding agent (antigen) that binds to a cognate antibody molecule or an antigen-binding portion thereof more readily than it would bind to a random, non-cognate antibody molecule. The term "specificity" is used herein to qualify the relative affinity by which an antigen binds to a cognate antibody. Specific binding typically means that an antigen binds to a cognate antibody at least twice more likely that to a random, non-cognate antibody (a 2:1 ratio of specific to non-specific binding). Non-specific binding refers to background binding, and is the amount of signal that is produced in a binding assay with an antigen when the cognate antibody molecule is not present in the assay. In some embodiments, specific binding will be at least three times the standard deviation of the background signal. In some specific embodiments, specific binding refers to binding between an antigen and an antibody with a dissociation constant (Kd) of 200 nM or less.

Antigens that are specific for or bind specifically to an antibody avoid binding to a significant percentage of non-target antibodies, e.g., non-target substances present in a testing sample. In some embodiments, antigens of the present disclosure avoid binding greater than about 90% of non-target substances, although higher percentages are clearly contemplated and preferred. For example, antigens of the present disclosure avoid binding about 91%, about 92%, about 93%, about 94%, about 95%, about 96%, about 97%, about 98%, about 99% or more of non-target substances.

As used herein, the term "linker" refers to one or more of a nucleotide, a nucleotide analog, an amino acid, a peptide, an antibody, a polymer, or a non-nucleotide chemical moiety that is used to join two molecules. A linker may be used to join an antigen with a coding tag, a recording tag with an antibody, an antibody with a support, a recording tag with a solid support, two antigens or two epitopes together, etc. In certain embodiments, a linker joins two molecules via enzymatic reaction or chemistry reaction (e.g., a click chemistry reaction).

As used herein, the term "coding tag" refers to a polynucleotide with any suitable length, e.g., a nucleic acid molecule of about 2 bases to about 100 bases, including any integer including 2 and 100 and in between, that comprises identifying information for its associated antigen (e.g., antigen). A "coding tag" may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety). A coding tag may comprise an encoder sequence, which is optionally flanked by one spacer on one side or optionally flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to an antigen, to a complementary sequence hybridized to the coding tag directly attached to an antigen (e.g., for double stranded coding tags), or to coding tag information present in an extended recording tag.

As used herein, the term "barcode" refers to a sequence of nucleotides of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) within a nucleic acid molecule that is used to identify (or provide a unique identifier tag or origin information for) an antibody, an antigen, a set of antigens from a binding cycle, a binding agent, or a sample. For example, a barcode can be used to identify molecules when the molecules from several groups are combined for processing or analyzing in a multiplexed fashion. A barcode can be an artificial sequence or a naturally occurring sequence. In certain embodiments, a barcode can comprise one or more pre-defined sequences. The term "pre-defined" means that sequence of a barcode is predetermined or known prior to identifying or without the need to identify the entire sequence of the nucleic acid comprising the barcode. In certain embodiments, each barcode within a population of barcodes is different. In other embodiments, only a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error-correcting or error-tolerant barcodes. Barcodes can be used to computationally deconvolute the multiplexed sequencing data and identify sequence reads derived from an individual antibody, sample, binding agent, etc. A "sample-specific barcode" refers to a polynucleotide sequence that is used to identify the origin or source of an antibody molecule. For example, a sequence of "AAAA" can be attached to beads to identify antibodies from sample A.

As used herein, the term "encoder sequence" or "encoder barcode" refers to a nucleic acid molecule of about 3 bases to about 30 bases in length that identifies or provides identifying information for its associated antigen. The encoder sequence present in the coding tag may uniquely identify the antigen that is attached to or associated with the coding tag. Alternatively, the encoder sequence may identify its associated antigen as belonging to a member of a set of two or more different antigens. In some embodiments, this level of identification is sufficient for the purposes of analysis. In some embodiments, where an encoder sequence identifies a set of possible antigens, a sequential decoding approach can be used to produce unique identification of each antigen. This is accomplished by varying encoder sequences for a given antigen in repeated cycles of binding (see, Gunderson et al., 2004, Genome Res. 14:870-7).

As used herein, the term "spacer" (Sp) refers to a nucleic acid molecule of about 1 base to about 20 bases (e.g., 1, 2, 3, 4, 5, 6, 7, 8, 9, 10, 11, 12, 13, 14, 15, 16, 17, 18, 19, or 20 bases) in length that is present on a terminus of a recording tag or coding tag. In certain embodiments, a spacer sequence flanks an encoder sequence of a coding tag on one end or both ends. Following binding of an antigen to an antibody, annealing between complementary spacer sequences on their associated coding tag and recording tag, respectively, allows transfer of binding information through a primer extension reaction or ligation to the recording tag. Sp' refers to spacer sequence complementary to Sp. Preferably, spacer sequences within a library of antigens possess the same number of bases. A common (shared or identical) spacer may be used in a library of antigens. A spacer sequence may have a "cycle specific" sequence in order to track antigens used in a particular binding cycle. A spacer sequence may comprise sufficient number of bases to anneal to a complementary spacer sequence in a recording tag to initiate a primer extension (also referred to as polymerase extension) reaction, or provide a "splint" for a ligation reaction, or mediate a "sticky end" ligation reaction.

As used herein, the term "recording tag" refers to a moiety, e.g., a chemical coupling moiety, a nucleic acid molecule, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag of an antigen can be transferred. Identifying information can comprise any information characterizing a molecule such as information pertaining to identity, sample, fraction, partition, spatial location, interacting neighboring molecule(s), cycle number, etc. Additionally, the presence of UMI can also be classified as identifying information. In certain embodiments, after an antigen binds to an antibody, information from a coding tag linked to an antigen can be transferred to the recording tag associated with the antibody while the antigen is bound to the antibody. In other embodiments, after an antigen binds to an antibody, information from a recording tag associated with the antibody can be transferred to the coding tag linked to the antigen while the antigen is bound to the antibody. A recording tag may be directly linked to an antibody, linked to an antibody via a multifunctional linker, or associated with an antibody by virtue of its proximity (or co-localization) on a support. A recording tag may be linked via its 5' end or 3' end or at an internal site, as long as the linkage is compatible with the method used to transfer coding tag information to the recording tag or vice versa. A recording tag may further comprise other functional components, e.g., a universal priming site, unique molecular identifier, a barcode (e.g., a sample-specific barcode, a fraction barcode, spatial barcode, a compartment tag, etc.), a spacer sequence that is complementary to a spacer sequence of a coding tag, or any combination thereof. The spacer sequence of a recording tag is preferably at the 3'-end of the recording tag in embodiments where polymerase extension is used to transfer coding tag information to the recording tag.

As used herein, the term "primer extension", also referred to as "polymerase extension", refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "unique molecular identifier" or "UMI" refers to a nucleic acid molecule of about 3 to about 40 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases) in length providing a unique identifier tag for each macromolecule, antibody or antigen to which the UMI is linked. A antibody UMI can be used to computationally deconvolute sequencing data from a plurality of extended recording tags to identify extended recording tags that originated from an individual antibody. A antibody UMI can be used to accurately count originating antibody molecules by collapsing NGS reads to unique UMIs. An antigen UMI can be used to identify each individual molecular antigen that binds to a particular antibody As used herein, the term "extended recording tag" refers to a recording tag to which information of at least one antigen's coding tag (or its complementary sequence) has been transferred following binding of the antigen to an antibody. Information of the coding tag may be transferred to the recording tag directly (e.g., ligation) or indirectly (e.g., primer extension). Information of a coding tag may be transferred to the recording tag enzymatically or chemically. An extended recording tag may comprise antigen information of 1, 2, 3, 4, 5, 10, 15, 20, 25, 30, 100, 200 or more coding tags. The base sequence of an extended recording tag may reflect the temporal and sequential order of binding of the antigens identified by their coding tags, may reflect a partial sequential order of binding of the antigens identified by the coding tags, or may not reflect any order of binding of the antigens identified by the coding tags. In certain embodiments, the coding tag information present in the extended recording tag represents with at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identity the antibody sequence being analyzed. In certain embodiments where the extended recording tag does not represent the antibody sequence being analyzed with 100% identity, errors may be due to off-target binding by an antigen.

As used herein, the term "solid support" or "support" refers to any solid material, including porous and non-porous materials, to which a polypeptide, such as an antibody, can be associated directly or indirectly, by any means known in the art, including covalent and non-covalent interactions, or any combination thereof. As used herein, the term "bead" refers to any three-dimensional solid support that can be mixed and used in the described assays. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. When solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, a controlled pore bead, a silica-based bead, or any combinations thereof. A bead may be spherical or an irregularly shaped. A bead or support may be porous. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 μm in diameter. In certain embodiments, "a bead" solid support may refer to an individual bead or a plurality of beads. In some embodiments, the bead is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, or between about 200 nm and about 500 nm in diameter. In some embodiments, the nanoparticles can be about 10 nm, about 50 nm, about 100 nm, about 150 nm, about 200 nm, about 300 nm, or about 500 nm in diameter. In some embodiments, the nanoparticles are less than about 200 nm in diameter.

As used herein, the term "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding. In some embodiments, the nucleic acid molecule or oligonucleotide is a modified oligonucleotide. In some embodiments, the nucleic acid molecule or oligonucleotide is a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof. In some embodiments, the nucleic acid molecule or oligonucleotide is backbone modified, sugar modified, or nucleobase modified. In some embodiments, the nucleic acid molecule or oligonucleotide has nucleobase protecting groups such as Alloc, electrophilic protecting groups such as thiranes, acetyl protecting groups, nitrobenzyl protecting groups, sulfonate protecting groups, or traditional base-labile protecting groups.

As used herein, "nucleic acid sequencing" means the determination of the order of nucleotides in a nucleic acid molecule or a sample of nucleic acid molecules. Similarly, "polypeptide sequencing" means the determination of the identity and order of at least a portion of amino acids in the polypeptide molecule or in a sample of polypeptide molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays (See e.g., Service, Science (2006) 311:1544-1546).

As used herein, "single molecule sequencing" or "third generation sequencing" refers to next-generation sequencing methods wherein reads from single molecule sequencing instruments are generated by sequencing of a single molecule of DNA. Unlike next generation sequencing methods that rely on amplification to clone many DNA molecules in parallel for sequencing in a phased approach, single molecule sequencing interrogates single molecules of DNA and does not require amplification or synchronization. Examples of single molecule sequencing methods include single molecule real-time sequencing (Pacific Biosciences), nanopore-based sequencing (Oxford Nanopore), duplex interrupted nanopore sequencing, and direct imaging of DNA using advanced microscopy.

As used herein, "analyzing" the polypeptide means to identify, detect, quantify, characterize, distinguish, or a combination thereof, all or a portion of the components of the polypeptide, e.g., an antibody or antibodies. For example, analyzing polypeptide includes determining all or a portion of the amino acid sequence (contiguous or noncontinuous) of the polypeptide. Analyzing the peptide may include combining different types of analysis, for example obtaining epitope information, amino acid sequence information, post-translational modification information, or any combination thereof.

The term "sequence identity" as used herein refers to a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. "Sequence identity" means the percentage of identical subunits at corresponding positions in two sequences when the two sequences are aligned to maximize subunit matching, i.e., taking into account gaps and insertions. For example, the BLAST algorithm calculates percent sequence identity and performs a statistical analysis of the similarity between the two sequences.

The term "unmodified" (also "wild-type" or "native") as used herein is used in connection with biological materials such as nucleic acid molecules and proteins, refers to those which are found in nature and not modified by human intervention.

As used herein, a polynucleotide or polypeptide variant, mutant, homologue, or modified version include polynucleotides or polypeptides that share nucleic acid or amino acid sequence identity with a reference polynucleotide or polypeptide. For example, variant or modified polypeptide generally exhibits about 25%, 30%, 40%, 50%, 60%, 70%, 80%, 85%, 86%, 87%, 88%, 89%, 90%, 91%, 92%, 93%, 94%, 95%, 96%, 97%, 98%, 99% or more sequence identity to a corresponding wild-type or unmodified polypeptide. The term "modified" or "engineered" (or "variant" or "mutant") as used in reference to polynucleotides and polypeptides implies that such molecules are created by human intervention and/or they are non-naturally occurring. A variant, mutant or modified polypeptide is not limited to any variant, mutant or modified polypeptide made or generated by a particular method of making and includes, for example, a variant, mutant or modified polypeptide made or generated by genetic selection, protein engineering, directed evolution, de novo recombinant DNA techniques, or combinations thereof. A mutant, variant or modified polypeptide is altered in primary amino acid sequence by substitution, addition, or deletion of amino acid residues. In some embodiments, variants of a polypeptide displaying only non-substantial or negligible differences in structure can be generated by making conservative amino acid substitutions in the modified polypeptide. By doing this, modified polypeptide variants that comprise a sequence having at least 90% (90%, 91%, 92%, 93%, 94%, 95%, 96%, 97%, 98%, and 99%) sequence identity with the modified polypeptide sequences can be generated, retaining at least one functional activity of the polypeptide. Examples of conservative amino acid changes are known in the art. Examples of non-conservative amino acid changes that are likely to cause major changes in protein structure are those, for example, that cause substitution of a hydrophilic residue to a hydrophobic residue. Methods of making targeted amino acid substitutions, deletions, truncations, and insertions are generally known in the art. For example, amino acid sequence variants can be prepared by mutations in the DNA. Methods for polynucleotide alterations are well known in the art, for example, Kunkel et al. (1987) Methods in Enzymol. 154:367-382; U.S. Pat. No. 4,873,192 and the references cited therein.

The terms "corresponding to position(s)" or "position(s) . . . with reference to position(s)" of or within a polypeptide or a polynucleotide, such as recitation that nucleotides or amino acid positions "correspond to" nucleotides or amino acid positions of a disclosed sequence, such sequence set forth in the Sequence Listing, refers to nucleotides or amino acid positions identified in the polynucleotide or in the polypeptide upon alignment with the disclosed sequence using a standard alignment algorithm, such as the BLAST algorithm (NCBI). One skilled in the art can identify any given amino acid residue in a given polypeptide at a position corresponding to a particular position of a reference sequence, such as set forth in the Sequence Listing, by performing alignment of the polypeptide sequence with the reference sequence (for example, by using BLASTP publicly available through the NCBI website), matching the corresponding position of the reference sequence with the position in polypeptide sequence and thus identifying the amino acid residue within the polypeptide.

As used herein, the term "associated with", e.g., "macromolecule associated with a component" indicates that the component may or may not be directly attached to the macromolecule by means of one or more covalent bond(s), but instead can be associated, or co-localized, with the macromolecule by means of non-covalent interactions, or, alternatively, be associated indirectly through a solid support (for example, when the macromolecule is attached to the solid support, and the component is independently attached to the solid support in a proximity to the macromolecule. The terms "attaching", "joining" and "linking" are used herein interchangeably and refer to either covalent or non-covalent attachment.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Throughout this disclosure, various disclosed methods comprise steps, e.g., a), b), c), d), e) and so on. It should be understood that these steps can be performed in any reasonable order, unless specifically stated otherwise.

Recently, a high-throughput single molecule peptide sequencing and analysis platform, termed ProteoCode™ Next-Generation Protein Assay (NGPA) has been described (for example, in US 2019/0145982 A1, US 2020/0348308 A1, US 2020/0348307 A1, WO 2020/223000, the contents of which are incorporated herein by reference in their entireties) that enables digital sequencing and identification of proteins within a sample. The ProteoCode™ assay encodes intermolecular interaction events into polynucleotide sequences in a massively-parallelized manner. Exemplary NGPA suitable for analyzing a macromolecule (e.g., polypeptide) analyte (FIG. 1) comprises the following steps: (a) providing the polypeptide analyte and an associated recording tag joined to a solid support; (b) contacting the polypeptide analyte with a first binding agent capable of binding to the polypeptide analyte, wherein the first binding agent comprises a first coding tag that comprises identifying information regarding the first binding agent; (c) following binding of the first binding agent to the polypeptide analyte, transferring the identifying information regarding the first binding agent from the first coding tag to the recording tag to generate a first order extended recording tag; (d) optionally, repeating steps (b) and (c) one or more times by replacing the first binding agent with a second or higher order binding agent capable of binding to the polypeptide analyte, wherein the second or higher order binding agent comprises a second or higher order coding tag that comprises identifying information regarding the second or higher order binding agent; and by transferring the identifying information regarding the second or higher order pbinding agent from the second or higher order coding tag to the first or higher order extended recording tag to generate a further extended recording tag; and (e) analyzing the first order extended recording tag or the further extended recording tag, wherein analyzing comprises a sequencing method, and obtaining the identifying information regarding the first binding agent and, optionally, the identifying information regarding the second or higher order binding agent to provide information regarding the polypeptide analyte, thereby analyzing the polypeptide analyte.

in the described NGPA assay, binding history of the immobilized polypeptide is recorded in the recording tag associated with the immobilized polypeptide and extended after one or more cycles of binding and transferring (steps (b) and (c), refers to as an "encoding cycle", as used herein). In preferred embodiments, in the described NGPA assay, multiple (at least 1000, at least 10,000, or at least 100,000) polypeptide analytes are analyzed in parallel (simultaneously in a single assay). In preferred embodiments, recording tags extended after the final encoding cycle and obtained from different polypeptide analytes, are pooled together and analyzed via next generation sequencing (NGS); then, information regarding the interaction events (binding history) is decoded (the identifying information regarding the specific binding agents is used to obtain information regarding the immobilized polypeptide).

In preferred embodiments of the NGPA assay, binding agent (e.g., an antibody, an aptamer or an antigen) is configured to recognize a specific epitope on the immobilized polypeptide (FIG. 1) or antigen-binding site of an antibody. In preferred embodiments, for successful encoding (which comprises transferring the identifying information regarding the binding agent bound to the peptide from the coding tag of the binding agent to the recording tag), binding agents have affinity (Kd) to a component of the polypeptide of less than 500 nM, and preferably less than 100 nM; sometimes in the range of 10-100 nM, or in the range of 1-10 nM.

Figure 2C:
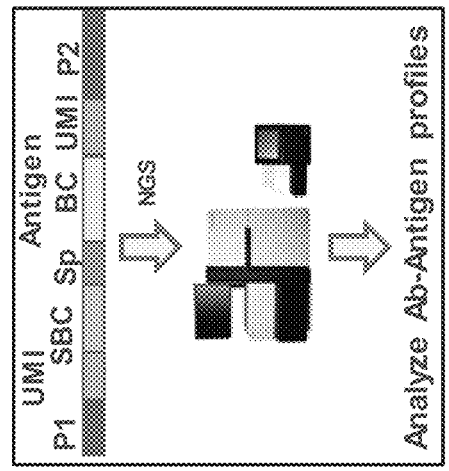
FIGS. 2A-2C. Exemplary encoding-based DST antibody profiling assay. Antibody molecules from a biological sample taken from a subject are attached to a support (e.g., beads) and each antibody molecule can be associated with a recording tag (rTag) comprising sample-specific barcode. The attachment of the antibody molecules does not rely on antigen-antibody binding, e.g., the attachment does not require using immobilized antigens to capture antibodies from the biological sample. As such, the rTag can be used to identify the sample (e.g., through the sample-specific barcode) but does not correspond to any particular antigen or an antigen binding molecule (e.g., antibody) thereof that may be present in the sample. A pool of peptide immunoassay antigens is labeled with DNA-barcoded coding tags (cTag) comprising antigen barcodes (encoder sequences). An antigen barcode can be an antigen-specific barcode that is specific to (e.g., uniquely identifies) an epitope of an antigen (e.g., each barcode corresponds to a different epitope of the same antigen). Alternatively, an antigen-specific barcode is specific to (e.g., uniquely identifies) an antigen, and the same barcode can correspond to different epitopes of the antigen. In some examples, an antigen barcode can correspond to and be shared by multiple different epitopes of the same antigen and/or different antigens (e.g., multiple different RBD epitopes of the S protein of one or more SARS-CoV-2 variants). In some examples, an antigen barcode can correspond to and be shared by multiple different antigens (e.g., epitopes in S1 or S2 of the same SARS-CoV-2 variant).
Figure 2B:
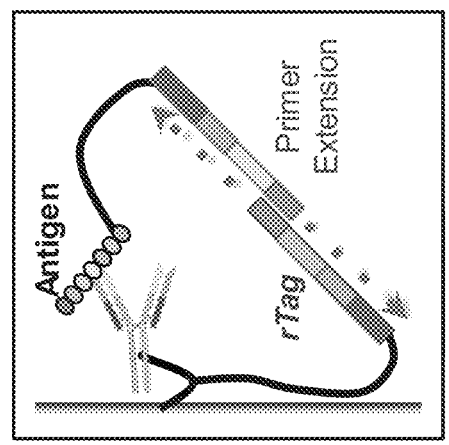
Figure 2A:
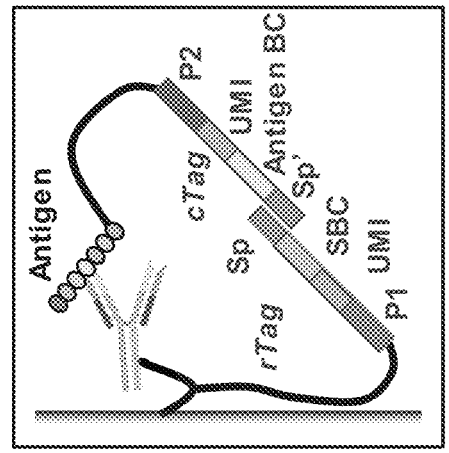

Several aspects of this digital encoding process that translates polypeptide binding events into DNA-encoded libraries are repurposed herein to measure the antibody humoral response in a large number of samples against a broad panel of antigens (the proposed methods referred to as Digital Serotyping (DST) assay herein; see FIGS. 2A-2C). In one particular embodiment, antibodies from a subject are attached to beads and coupled to DNA barcoded protein A/G beads providing sample identification, and upon binding of an antibody to a DNA-tagged assay antigen (FIG. 2A), information is transferred by a polymerase-mediated primer extension step (FIG. 2B). The composite DNA tag generated by proximity interaction is composed of barcodes (sample and analyte), priming sites and an optional unique molecular identifier (UMI) that enables accurate count of binding interactions between antigens and antibodies. This format allows for encoding binding interactions between synthetic, pathogen-derived epitopes and serum antibodies from individual donors in a highly multiplexed fashion.

The disclosed variants of the Digital Serotyping (DST) assay provide improved sensitivity using digital single molecule counting (by using NGS), and improved specificity by using multiple antigens to provide better discrimination power. Multiplexing can be achieved by using sample barcoding prior to serotyping to facilitate population level studies, as well as by using antigen barcoding to scale the number of antigens profiled per sample. The DST assay can be designed to be restricted to detection of a single pathogen, such as CoV2, or designed to profile a comprehensive set of pathogens, showing excellent flexibility; the major determinant is the total amount of NGS sequencing required.

In a preferred embodiment of the DST assay, a method for sample analysis is provided, comprising: a) (i) separately contacting a plurality of different antibodies of each sample of a plurality of samples with a binding element configured to bind to the plurality of different antibodies in the sample, thereby obtaining binding element-antibody conjugates; and (ii) attaching either the binding element or the binding element-antibody conjugates to a bead, wherein the binding element is attached to the bead before or after contacting the plurality of different antibodies, wherein the binding element is associated with a recording tag comprising a sample-specific barcode before or after attachment to the bead, thereby obtaining a plurality of beads comprising attached binding element-antibody conjugates each associated with the recording tag from each sample; b) mixing the pluralities of beads comprising attached binding element-antibody conjugates from the plurality of samples, thereby obtaining a mixture of beads; c) contacting the mixture of beads with a binding agent comprising an antigen and a coding tag attached thereto, wherein the coding tag comprises an encoder sequence that comprises identifying information regarding the antigen; d) following binding of the antigen to an antibody attached to a bead of the mixture of beads, allowing transfer of identifying information between the coding tag and the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

In some embodiments of the DST assay, in a), beads comprising the attached binding element and the recording tag comprising a sample-specific barcode and associated with the binding element are contacted with the plurality of different antibodies of each sample.

In the first variant of the DST assay, a method for sample analysis is provided, comprising: a) separately contacting each sample of a plurality of samples with a plurality of beads, wherein each bead of the plurality of beads contacted with the sample comprises i) a recording tag comprising a sample-specific barcode and ii) an associated binding element configured to bind to a plurality of different antibodies in the sample, thereby obtaining a plurality of antibody-bound beads from each sample; b) mixing the pluralities of antibody-bound beads from the plurality of samples, thereby obtaining a mixture of beads; c) contacting the mixture of beads with a binding agent comprising an antigen and a coding tag attached thereto, wherein the coding tag comprises an encoder sequence that comprises identifying information regarding the antigen; d) following binding of the antigen to an antibody attached to a bead of the mixture of beads, allowing transfer of identifying information between the coding tag and the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

In the second variant of the DST assay, a method for sample analysis is provided, comprising: a) separately contacting each sample of a plurality of samples with i) a nucleic acid tag comprising a sample-specific barcode, and ii) a binding element configured to bind to a plurality of different antibodies in the sample, thereby obtaining a plurality of nucleic acid-bound antibody-binding agent complexes for each sample; b) mixing the pluralities of nucleic acid-bound antibody-binding agent complexes for the plurality of samples and immobilizing them on a plurality of beads, wherein the plurality of beads optionally comprises a plurality of nucleic acid recording tags, thereby obtaining a mixture of beads comprising a plurality of immobilized antibodies each associated with a nucleic acid tag or recording tag; c) contacting the mixture of beads with a binding agent comprising an antigen and a coding tag attached thereto, wherein the coding tag comprises an encoder sequence that comprises identifying information regarding the antigen; d) following binding of the antigen to an antibody attached to a bead of the mixture of beads, allowing transfer of identifying information between the coding tag and the nucleic acid tag or the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

Various embodiments apply equally to the DST assay variants provided herein but will for the sake of brevity be recited only once. Thus, various of the following embodiments apply equally to the assay variants recited above.

Figure 7A:
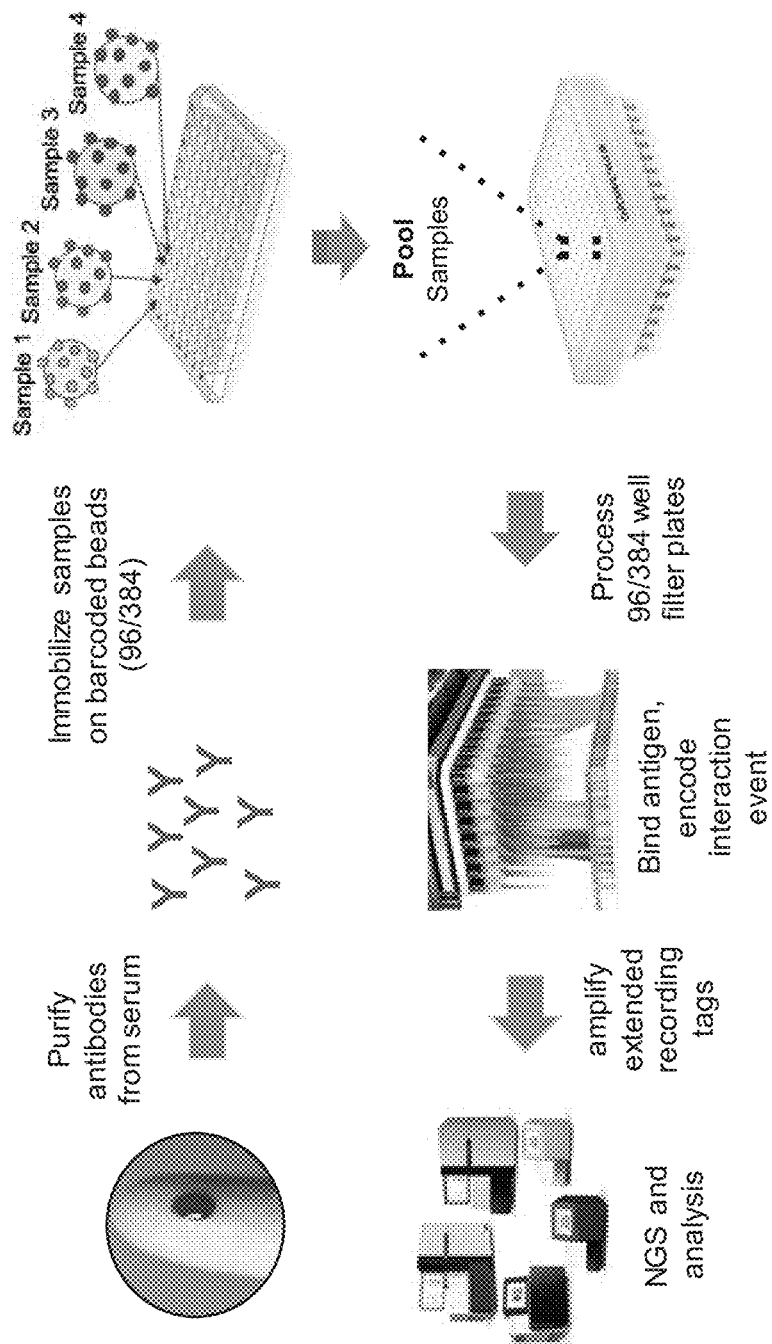
FIGS. 7A-7B. Exemplary population-wide serotyping (DST) assay setup.
Figure 7B:
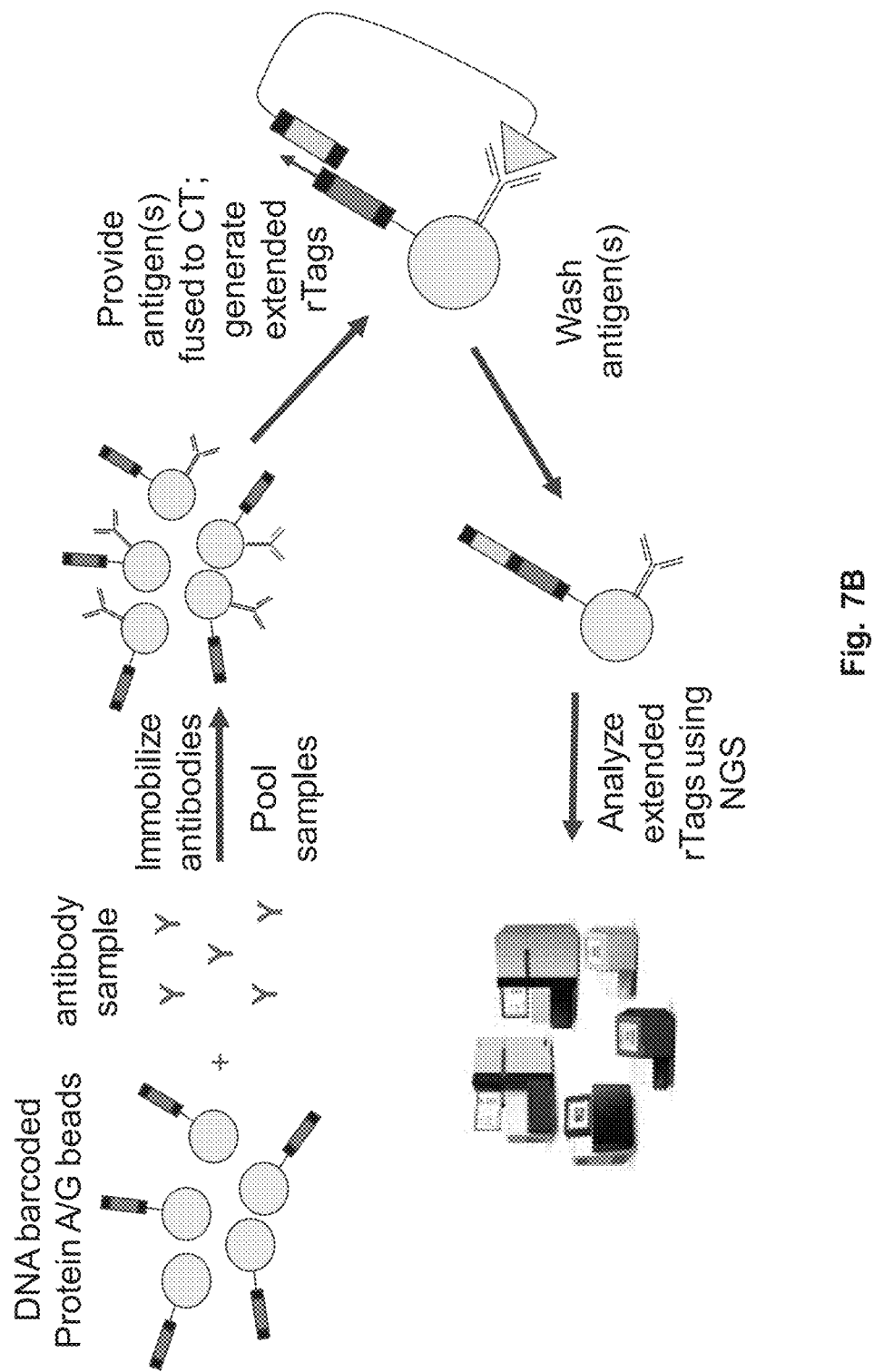

The disclosed variants of the DST assay offer unique capabilities compared to traditional immunoassay due to ability to process multiple pooled samples in a single assay and encode binding interactions in DNA libraries in a high throughput manner FIGS. 7A-7B show exemplary embodiment of the DST assay, where sample pooling enables high-throughput serology. An entire sample plate can be collapsed into a single well on the encoding-based DST assay filter plate enabling up to 384×384=150 k samples to be processed per 384-well assay plate (FIG. 7A). FIG. 7B shows an exemplary encoding process, which translates specific antibody-antigen binding interactions into nucleic acid libraries (comprising recording tags extended during the encoding step). Combining sample multiplexing with high throughput encoding of binding interactions results in ability to generate population scale immune repertoire profiling or perform population scale serology surveillance. The disclosed variants of the DST assay are also applicable for epitope mapping, drug discovery and other applications.

Some variants of the DST assay include solution-phase tagging of antibodies with nucleic acid tags, whereas in the first variant of the DST assay antibodies are tagged with nucleic acid tags attached to a solid support, such as beads. In some embodiments of the DST assay, nucleic acid tags are already present on the solid support (e.g., plurality of beads) before contacting beads with antibody molecules. In some embodiments, nucleic acid tags attached to beads are used for immobilization of antibody molecules on the beads. In some embodiments, nucleic acid tags are attached to antibody molecules before immobilization, and recording tags are formed upon immobilization on the solid support (the presence of nucleic acid tags on the solid support before immobilization is not required). In the second variant of the DST assay, the nucleic acid tag comprising a sample-specific barcode may comprise recording tag; alternatively, the nucleic acid tag may be used to generate a recording tag configured to be associated with the immobilized antibody upon immobilization on the solid support.

In some embodiments of the DST assay, when contacting each sample of the plurality of samples with a plurality of beads, each bead of the plurality of beads comprises a recording tag and an associated binding element configured to bind to antibodies from the plurality of samples, and the recording tag of each bead from the pluralities of beads comprises a sample-specific barcode that is the same for beads within each plurality of beads that are contacted with the same sample, and is different for beads from different pluralities of beads that are contacted with different samples. In some embodiments, some of the sample-specific barcodes present on beads that are in contact with the same sample may differ from other sample-specific barcodes, such as they may be defective for various reasons. For example, in some embodiments, less than 0.1%, less than 0.2%, less than 0.5%, less than 1%, less than 2% or less than 5% of sample-specific barcodes that are specific to the same sample are defective and are different from other sample-specific barcodes that are specific to the same sample. Defective barcodes may be filtered out during the analyzing step, and thus may not interfere with obtaining information regarding the antigen, the antibody interacting with the antigen, and the sample that contained the antibody.

In some embodiments of the DST assay, the binding element can be associated with or attached to the sample-specific barcode before contacting step; alternatively, the binding element and specific barcode can independently contact antibodies.

In preferred embodiments of the disclosed methods, the barcodes and encoder sequences are comprised of a random nucleotide sequence (via oligonucleotide synthesis using a mixed base (e.g. N), much like a unique molecular identifier (UMI), but in this case the barcode contains a unique sample or antigen identifier). General methods of generating barcodes, UMIs or encoder sequences are known in the art, and can be found, for example, in US 20190145982 A1, U.S. Pat. No. 10,144,950 B2; US 20180273933 A1, US 20160253584 A1, incorporated herein by reference. In some embodiments, barcodes are constructed through split-pool synthesis using chemical synthesis or enzymatic synthesis on beads and subsequent cleavage off the beads (Delley and Abate. 2021. "Modular Barcode Beads for Microfluidic Single Cell Genomics." Scientific Reports 11 (1): 10857; Zilionis, et al., 2017. "Single-Cell Barcoding and Sequencing Using Droplet Microfluidics." Nature Protocols 12 (1): 44-73). In some embodiments, barcodes (or encoder sequences) constitute a library of unique barcodes (or encoder sequences) such that the number of unique barcodes (or encoder sequences) exceeds the number of samples (or antigens) by at least hundred-fold or greater. In this way, "collisions" between nucleic acid sequences with the same barcode are minimized effectively assigning associated analytes to unique barcodes.

In some embodiments of the DST assay, following binding of the antigen to the first antibody, the transfer of identifying information occurs from the coding tag to the recording tag associated with the first antibody, thereby generating the extended recording tag, and the encoder sequence or the complement thereof transferred to the extended recording tag is analyzed (together with the sample-specific barcode) to decode identities of the antigen, the first antibody that binds to the antigen, and the sample that contained the first antibody that binds to the antigen. In preferred embodiments of the DST assay, the transfer occurs through a primer extension reaction and/or ligation. In other embodiments of the DST assay, following binding of the antigen to the first antibody, the transfer of identifying information occurs from the recording tag associated with the first antibody to the coding tag attached to the antigen, thereby generating the extended coding tag attached to the antigen, and the sample-specific barcode or the complement thereof transferred to the extended coding tag is analyzed (together with the encoder sequence) to decode identities of the antigen, the first antibody that binds to the antigen, and the sample that contained the first antibody. In these embodiments, recording tags or nucleic acid tags attached to beads and associated with antibody molecules may further comprise a unique molecular identifier (UMI), which distinguishes different antibody molecules attached to different beads. In preferred embodiments of the DST assay, the transfer occurs through a primer extension reaction and/or ligation.

In some embodiments of the DST assay, the identifying information transferred after binding of the antigen to a cognate antibody attached to a bead comprises the encoder sequence (i.e., the antigen barcode) or a complement thereof, and optionally also comprises a UMI present on the coding tag associated with the antigen. In some embodiments of the DST assay, the identifying information transferred after binding of the antigen to a cognate antibody attached to a bead comprises the sample-specific barcode or a complement thereof, and optionally also comprises a UMI present on the recording tag associated with the antibody on the bead.

In some embodiments of the DST assay, after the transfer of identifying information, the extended coding tags attached to the antigen(s) are formed, wherein each extended coding tag comprises the encoder sequence, the sample-specific barcode or a complement thereof, and, optionally, a UMI or a complement thereof. In these embodiments, after the binding and transfer steps, antigens with attached extended coding tags are collected and analyzed using a nucleic acid sequencing. In some other embodiments of the DST assay, after the transfer of identifying information, the extended recording tags attached to the beads are formed, wherein each extended recording tag comprises the encoder sequence or a complement thereof, the sample-specific barcode, and, optionally, a UMI. In these embodiments, after the binding and transfer steps, extended recording tags may be optionally amplified by a polymerase chain reaction and analyzed using a nucleic acid sequencing.

In some embodiments of the DST assay, analyzing the encoder sequence or a complement thereof and the sample-specific barcode or a complement thereof comprises sequencing all or a portion of these sequences. To perform sequencing, these sequences may be amplified, and optionally attached to adaptor sequences suitable for a particular sequencing platform.

In some embodiments of the DST assay, each bead of the plurality of beads comprises a recording tag and an associated binding element configured to bind to antibodies from the plurality of samples. In these embodiments, both recording tag and the binding element are directly or indirectly (e.g., via a linker) attached to the bead. Various ways of attachment and association between the recording tag and the binding element are possible. Attachment can be covalent, non-covalent, or through combination of covalent and non-covalent interactions. In some embodiments, attachment methods include bioorthogonal click chemistry methods. Some specific examples of attachment methods are described below. In some embodiments, the association between the recording tag and the binding element may be direct (e.g., the recording tag is attached to the binding element) or indirect (e.g., the recording tag is not attached to the binding element, but instead is associated through the bead (the recording tag and the binding element are independently attached to the same bead)).

In some embodiments, interactions between the binding element and antibody molecules can be covalent or non-covalent. In preferred embodiments, non-covalent initial interactions between the binding element and antibody molecules become covalent by cross-linking the antibody molecules to the binding element.

In preferred embodiments of the DST assay, nucleic acid tags are used that comprise barcodes, such as sample-specific barcodes or antigen barcodes (i.e., encoder sequences). In some embodiments, error-correcting or error-tolerant barcodes can be used to decrease potential errors during analyzing and decoding of barcode sequences. Nucleic acid barcodes can be designed to be tolerant to error-prone NGS sequencers, such as nanopore-based sequencers where the current base call error rate is around 5-10%. A number of error correcting code systems have been described in the art and can be used herein. These include Hamming codes, Lee distance codes, asymmetric Lee distance codes, Reed-Solomon codes, Levenshtein codes, and others. Error-tolerant barcodes can be generated based on Hamming and Levenshtein codes using R Bioconductor package, "DNAbarcodes", which are capable of correcting insertion, deletion, and substitution errors, depending on the design parameters chosen (see, e.g., US 20190145982 A1 and Buschmann and Bystrykh, 2013, Levenshtein error-correcting barcodes for multiplexed DNA sequencing. BMC Bioinformatics 14, 272 (2013), incorporated herein by reference).

In some embodiments of the DST assay, the method comprises contacting each sample of the plurality of samples with a nucleic acid tag comprising a sample-specific barcode, and with a binding element configured to bind to antibodies from the samples, thereby obtaining antibodies bound to the nucleic acid tag and to the binding element. This step may be performed in solution without prior attachment of tags or the binding element to beads. Various binding configurations can be utilized to obtain antibodies bound to the nucleic acid tag and to the binding element. In some embodiments, the binding element may be associated directly or indirectly with the nucleic acid tag comprising a sample-specific barcode, and then this conjugate may bind to antibodies from the samples. In some embodiments, the binding element may not be associated with the nucleic acid tag comprising a sample-specific barcode, and instead these moieties independently interact with antibodies from the samples. A skilled person will recognize other possibilities for obtaining antibodies bound to the nucleic acid tag and to the binding element.

In some embodiments of the DST assay, nucleic acid tags are configured to attach to polypeptides, such as antibodies or the polypeptide-based binding element. Various attachment approaches of nucleic acid tags to polypeptides are known in the art and can be utilized in the disclosed methods. For example, five different examples of amino acid residues on polypeptides that can be modified directly with activated DNA tags are described (Lundblad, R (2014) Chemical reagents for protein modification. Boca Raton, CRC Press, Taylor & Francis Group) using activation with heterobifunctional amino acid site-specific reagents or indirectly via click chemistry heterobifunctional reagent that site-specifically labels amino acid residues with a click moiety that is later used to attach a cognate click moiety on the DNA tag. A typical protein input comprises 1 µg protein in 50 µl appropriate aqueous buffer containing 0.1% RapiGest™ SF surfactant, and 5 mM TCEP. RapiGest™ SD is useful as an acid degradable surfactant for denaturing proteins into polypeptides for improving labeling or digestion. The following amino acid labeling strategies can be used: cysteines using maleimide chemistry-200 µM Sulfo-SMCC-activated DNA tags are used to site-specifically label cysteines in 100 mM MES buffer (pH 6.5)+1% TX-100 for 1 hr.; lysines using NHS chemistry-200 µM DSS or BS3-activated DNA tags are used to site-specifically label lysine on solution phase proteins or the bead-bound peptides in borate buffer (50 mM, pH 8.5)+1% TX-100 for 1 hr. at room temp; tyrosine is modified with 4-Phenyl-3H-1,2,4-triazoline-3,5(4H)-diones (PTAD) or diazonium chemistry—for diazonium chemistry, DNA Tags are activated with EDC and 4-carboxylbenzene diazonium tetrafluoroborate (Aikon International, China). The diazo linkage with tyrosine is created by incubating the protein or bead-bound peptides with 200 µM diazonium-derivatized DNA tags in borate buffer (50 mM, pH 8.5)+1% TX-100 for 1 h on ice (Nguyen et al., 2015, "Site-Specific N-Terminal Labeling of Peptides and Proteins using Butelase 1 and Thiodepsipeptide." Angew Chem Int Ed Engl 54(52): 15694-15698). Aspartate/glutamate is modified using EDC chemistry—an amine-labeled DNA tag is incubated with the bead-bound peptides and 100 mM EDC/50 mM imidazole in pH 6.5 MES for 1 hr. at room temperature (Basle et al., 2010, Chem. Biol. 17:213-227). After labeling, excess activated DNA tags are removed using protein binding elution from C4 resin Zip-Tips (Millipore). The eluted proteins are brought up 50 µl 1×PBS buffer. In some embodiments, a specific type of amino acid residues in polypeptides is modified prior to attachment of nucleic acid tags. For example, a specific type of amino acid residues can be modified with a reactive handle, and then the reactive handle can react with modified nucleic acid tags covalently attaching them to the specific type of amino acid residues. In some embodiments, the first and/or second reactive handles used to attach specific amino acid residues of the polypeptide and nucleic acid tags comprise a bio-orthogonal reactive group (click chemistry reagent). In preferred embodiments, the bio-orthogonal reactive group is a reaction partner for an inverse electron demand Diels—Alder (IEDDA) reaction. Some examples of reactions useful for the attachment that can be utilized herein are disclosed, for example, in U.S. Pat. Nos. 10,697,974 B2, 8,236,949 B2, 9,169,283 B2, 10,611,738 B2, 10,442,789 B2, 10,006,917 B2, and in Fox J M, et al., "General, Divergent Platform for Diastereoselective Synthesis of trans-Cyclooctenes with High Reactivity and Favorable Physiochemical Properties. Angew Chem Int Ed Engl. 2021 Mar. 19", incorporated herein by reference.

In some embodiments of the DST assay, the method comprises mixing the antibodies bound to the nucleic acid tag and to the binding element from different samples; and immobilizing the antibodies on a plurality of beads, wherein the plurality of beads optionally comprises a plurality of nucleic acid recording tags, thereby forming a plurality of immobilized antibodies each associated with a nucleic acid tag or recording tag. Various immobilization approaches of antibody molecules to beads are known in the art and can be utilized in the disclosed methods. In some embodiments, antibody molecules may be directly immobilized to beads. For example, antibody molecules may first be labeled with a strained alkyne-modified nucleic acid tag followed by immobilization on azide-activated beads. In a particular embodiment, azide-derivatized Dynabeads beads are generated by reacting commercially available amine Dynabeads® M-270 beads with an azide PEG NHS ester heterobifunctional linker (JenKem Technology, TX). Further, the surface density of azide can be titrated by mixing in methoxy or hydroxyl PEG NHS ester in the appropriate ratio. For a given antibody sample, 1-2 mg azide-derivitized Dynabeads® M-270 beads (~1.3×108 beads) is diluted in 100 µl borate buffer (50 mM sodium borate, pH 8.5), 1 ng nucleic acid tag-antibody is added, and incubated for 1 h at 23-37° C. followed by washing 3× with 200 µl borate buffer. Other bioorthogonal click chemistry reactions can be used for immobilization of antibody molecules on beads, which are disclosed, for example, in U.S. Pat. No. 10,697,974 B2, 8,236,949 B2, 9,169,283 B2, 10,611,738 B2, 10,442,789 B2, incorporated herein by reference. In some embodiments, specific amino acid residues (such as Lys) of antibody molecules may be labeled and used for the immobilization.

In some embodiments, antibody molecules are attached to a plurality of beads, wherein the plurality of beads comprises a plurality of nucleic acid recording tags, and immobilization of antibody molecules occurs through nucleic acid hybridization. Exemplary methods of immobilization of polypeptide molecules on a solid support (such as beads) through nucleic acid hybridization are disclosed in US 2022/0049246 A1, incorporated herein by reference Immobilization through nucleic acid hybridization can be faster and can require smaller concentrations of polypeptide analytes compared to click chemistry-based immobilization (e.g., 10 nM concentration of polypeptide analytes in a ~15 min hybridization step, see US 2022/0049246 A1), thus increasing immobilization efficiency.

In some embodiments, antibody molecules are attached to a plurality of beads, wherein the plurality of beads comprises binding element configured to bind to antibodies.

In preferred embodiments, antibody molecules are attached to a plurality of beads via regions distinct from epitope-binding regions, such as via conservative regions shared among different antibodies (e.g., a portion of Fc region of antibody molecules), and not via complementarity-determining regions (CDRs). In some embodiments, the binding element is configured to bind to antibodies from the plurality of samples via regions distinct from epitope-binding regions (e.g., distinct from CDRs). The advantage of this approach is such immobilization is more uniform, and all antibodies are immobilized including antibodies of various affinities and concentrations. When epitope-binding regions of antibody molecules are used for immobilization or interaction with the binding element, lower affinity or low titer (rare) antibodies may not be immobilized effectively. This immobilization approach will result in better sensitivity and linearity for the DST assay. To increase signal from lower affinity antibodies after immobilization, the antigen concentration in solution may be increased, driving efficiency of the binding reaction.

In some embodiments, the nucleic acid tag interacts with a capture DNA attached to the solid support via nucleic acid hybridization, and this interaction is used for the immobilization of the nucleic acid tag-antibody conjugate. In some embodiments, recording tag associated with the immobilized antibody can be formed from the nucleic acid tag associated with the immobilized antibody via primer extension or ligation. The recording tag can be associated with the immobilized antibody either directly (e.g., using a covalent bond), or indirectly, for example, via a linker or via the solid support. In some embodiments, after antibody immobilization, the recording tag is attached to the solid support, and the antibody is also independently attached to the solid support, without direct attachment to the recording tag. Nevertheless, such indirect association between the recording tag and the antibody supports further method steps, such as transfer of the identifying information regarding the antigen following binding of the antigen to the immobilized antibody, because the antigen and the attached coding tag can interact with the antibody and the recording tag, respectively, independent of each other. In some embodiments, the antigen is attached to the coding tag via a flexible linker, such as peptide linker, to provide more efficient interaction with their interaction partners (the antibody and the recording tag, respectively).

In some embodiments of the DST assay, assessing the levels of the antibody comprises detecting the presence of the antibody in several or multiple samples in a single assay. In these embodiments, only qualitative assessment of antibody levels is used. In other embodiments, quantitative or semi-quantitative assessment of antibody levels is used. In these embodiments, levels of the antibody in different samples can be compared.

In some embodiments of the DST assay, analyzing the one or more recording tags extended after encoding cycles can comprise releasing the one or more extended recording tags, or copy thereof, or complement thereof, from the mixture of beads; optionally amplifying the extended recording tags or complement thereof; sequencing the released extended recording tags or complement thereof; associating sequence information of each released extended recording tag with the identifying information regarding the antigen and the subject (using the sample-specific barcode), and thus obtaining information regarding the presence or the level of an antibody that binds the antigen in the particular sample.

Large numbers of peptide epitope antigens conjugated to DNA coding tags (antigen-DNA conjugates) can easily be constructed by high-throughput peptide synthesis and DNA conjugation. The DNA can be appended with a peptide comprised of a linker sequence and a non-standard amino acid capable of "click-chemistry" bioconjugation. An exemplar sequence is GSGSGSK$_{azide}$ (SEQ ID NO: 1), wherein the lysine-azide group can easily be "click" conjugated to an alkyne or strained alkyne on a synthetic oligonucleotide. Alternately, peptide-DNA conjugates can be synthesized using cDNA display techniques in which a DNA coding tag can be incorporated into the peptide sequence during cDNA display of a peptide sequence library. Known peptide epitopes for pathogenic proteins can be synthesized with GSGSGSK peptide linker (SEQ ID NO: 1) wherein the C-terminal lysine is azide modified. Unique DNA tags may be appended to each peptide using DBCO-mediated click chemistry with a PEG linker to improve solubility.

In preferred embodiments, the described Digital Serotyping (DST) assay provides population-level serotyping of serum/tissues important to infectious disease monitoring and surveillance. Moreover, the methods described herein help to perform population-level serotyping by enabling processing of millions of samples per lab. This is further facilitated by enablement of ultra-low cost per sample analysis due to economies of scale realized from the large-scale sample and analyte multiplexing. In addition, the described technology is highly adaptable allowing almost real-time deployment of updated antigen sequences to keep abreast of evolving infectious subtypes and strains, whether for influenza, Covid-19, or other infectious diseases. Finally, the antigen multiplexing capability of the DST assay enables differential detection of exposure to multiple infectious agents, and increases sensitivity and specificity for testing for a specific infectious agent. Other advantages or this approach include the ability to use either tiled peptide antigens enabling antibody epitope mapping, and or to use glycosylated protein fragments expressed in mammalian cells or engineered yeast cells mimicking mammalian glycosylation (Pichia GlycoSwitch® technology, Research Corporation Technologies, AZ) which provides a more native epitope in the assay. Additionally, DST assay provides greatly improved limits of detection enabling serotyping from limited material inputs (e.g., drop of blood, dried blood spots, etc.) or from low titer antibodies.

In some embodiments of the DST assay, the binding element comprises an immunoglobulin-binding protein or peptide selected from the group consisting of: Protein A, Protein G, Z domain of Protein A, C2 domain of Protein G, HTB1 domain of Protein G, Protein L, Protein LG, Protein AG, Protein AL, Protein LG, Protein AGL, Protein M, IbpM, FC-III peptide, immunoglobulin-binding fragments thereof, and an immunoglobulin-binding derivative(s) thereof (e.g., FC-III bicyclic derivatives including FcBP-2 and FC-III-4C) (Witting, et al., 2021. "Affinity-Based Methods for Site-Specific Conjugation of Antibodies." Bioconjugate Chemistry 32 (8): 1515-24; Muguruma, et al. 2019. "Kinetics-Based Structural Requirements of Human Immunoglobulin G Binding Peptides." ACS Omega 4 (11): 14390-97).

Fragments of immunoglobulin-binding proteins retain immunoglobulin-binding properties despite missing some of the amino acid sequence of the proteins. Derivatives of an immunoglobulin-binding protein comprise immunoglobulin-binding proteins having at least 30%, at least 40%, at least 50%, at least 60%, at least 70%, at least 80%, at least 90%, or at least 95% sequence identity to the immunoglobulin-binding protein and retaining immunoglobulin-binding property. In some embodiments, the binding element consists of or consists essentially of an immunoglobulin-binding protein selected from the group consisting of: Protein A, Protein G, Z domain of Protein A, C2 domain of Protein G, Protein L, Protein LG, Protein AG, Protein AL, Protein M, IbpM, immunoglobulin-binding fragments thereof, and an immunoglobulin-binding derivative(s) thereof. In some embodiments, the binding element comprises an immunoglobulin-binding protein or peptide having an amino acid sequence that is at least 90% identical to one of the sequences set forth in SEQ ID NO: 38-41 and SEQ ID NO: 44-48.

In some embodiments of the DST assay, the binding element specifically binds to a feature or to a component of antibody molecules. In some embodiments, the binding element specifically binds to a heavy chain, a light chain or a glycan sites of antibody molecules. In some embodiments, the binding element specifically binds to a particular isotype of antibodies, such as binds IgG molecules. In other embodiments, the binding element specifically binds to a particular subclass of antibodies, such as subclass of IgG molecules, for example binds IgG3. As an example, the binding element can comprise Fcγ receptor (FcγR) specific for a particular IgG antibody subclass. Specificity of the IgG Fc domain for different classes of FcγRs is largely determined by the primary amino acid backbone sequence of the varying IgG subclasses (IgG1, IgG2, IgG3, and IgG4 in humans). In other embodiments, the binding element binds to two or more isotypes or subclasses of antibodies. As an example, the binding element can comprise Protein L that binds to representatives of all antibody classes, including IgG, IgM, IgA, IgE and IgD.

In some embodiments, for solution-phase labeling of plasma immunoglobulins with sample-specific barcodes, it is useful to employ subdomains of Protein A or G or L, which limit binding stoichiometry to 1:1 between the subdomain and the Fc portion of the heavy chain of the antibody (Wittig, 2021). Exemplar immunoglobulin binding protein subdomains include the Protein A subdomain, the Z domain; and the Protein G subdomain, the C2 domain (Perols, 2014) and the HTB1 domain (Hui, et al. 2015. "LASIC: Light Activated Site-Specific Conjugation of Native IgGs." Bioconjugate Chemistry 26 (8): 1456-60). The immunoglobulin IgG is bound by C2 or Z and IgM by C2. The C2, HTB1, and Z subdomains are compact (~55-60 amino acids), bind immunoglobulins with low nM affinity, and can be photoaffinity coupled to immunoglobulins using synthetic incorporation of benzophenone (BP or 4-benzoylphenylalanine (BPA) moieties (Perols, 2014, Kanje, Herrmann et al. 2016, Stiller, Aghelpasand et al. 2019). Commercial kits for antibody labeling with DNA tags using a variant of the C2 protein, called oYo-Link® Oligo Custom conjugation can also be used (AlphaThera, PA).

Alternatively, immunoglobulin binding peptides have also been developed with an exemplar peptide being the FC-III 13-mer cyclic peptide generated by phage display of peptides for Fc-mediated antibody binding (Choe, et al. 2016. "Fc-Binding Ligands of Immunoglobulin G: An Overview of High Affinity Proteins and Peptides." Materials 9 (12)). FC-III has been subsequently engineered to increase its immunoglobulin binding affinity to low nM levels. The advantage of the FC-III cyclic peptide is that it can be easily synthesized on standard peptide synthesizers and "clickchemistry" non-natural amino acids incorporated during synthesis. Additionally, benzophenone can be incorporated into the FC-III peptide for photo-crosslinking to antibodies, similar to the Z and C2 subdomains (Park, et al. 2018. "Peptide-Directed Photo-Cross-Linking for Site-Specific Conjugation of IgG." Bioconjugate Chemistry 29 (10): 3240-44).

In some embodiments of the DST assay, the binding element comprises a synthetic ligand that is able to selectively and strongly bind to antibodies. For example, small molecules have been developed to mimic the binding properties of bacterial proteins that bind to antibodies (Roque A., et al., Affinity-based methodologies and ligands for antibody purification: Advances and perspectives. J. Chromatogr. A 2007, 1160, 44-55; Fassina G, et al., Novel ligands for the affinity-chromatographic purification of antibodies. J. Biochem. Biophys. Methods 2001, 49, 481-490; Kabir S Immunoglobulin purification by affinity chromatography using protein A mimetic ligands prepared by combinatorial chemical synthesis. Immunol. Investig. 2002, 31, 263-278). High throughput screening methods of small molecule candidates can used to select ligands having high affinity towards antibodies.

In some embodiments, the binding element comprises a branched- and cyclic peptide-based high affinity ligand that specifically bind to IgG molecules through interaction with the Fc-domain (Choe W, et al., Fc-Binding Ligands of Immunoglobulin G: An Overview of High Affinity Proteins and Peptides. Materials (Basel). 2016 Dec. 8; 9(12):994). Examples of such branched or cyclic IgG-interacting peptides include PAM, FcRM, Fc-III-4C, FcBP-2 (Choe W, et al., Materials (Basel). 2016 Dec. 8;9(12):994, and references herein). The reported affinity constants (represented by equilibrium dissociation constant, Kd) for these ligands are reported to be from 2 nM to 1 uM. In some embodiments, antibodies from biological samples can be attached to beads using a selective reaction with antibody glycans (Zeglis, et al. 2013. "Enzyme-Mediated Methodology for the Site-Specific Radiolabeling of Antibodies Based on Catalyst-Free Click Chemistry." Bioconjugate Chemistry 24 (6): 1057-67). In general, IgG antibodies contain a conserved N-linked glycosylation site on the CH2 domain of each heavy chain of the Fc region amenable to labeling.

In some embodiments, antibodies from samples are attached to beads using a selective reaction with antibody glycans. In one example, carbohydrate-binding modules (CBMs) derived from carbohydrate related enzymes, which have function for specific recognition of certain carbohydrates, can be utilized. In another example, GlyCLICK enables site-specific and quantitative conjugation of IgG from several species and subclasses utilizing click-chemistry reagents (Sadiki A, et al., Site-specific conjugation of native antibody. Antib Ther. 2020 December; 3(4):271-284). First, antibodies are deglycosylated using the Fc specific Endoglycosidase (EndoS2) that hydrolyzes the Fc glycans to the inner most GlcNAc moiety on several subclasses and species of IgG. The enzyme removes all glycoforms, including; high-mannose, hybrid, complex, and bisecting type glycans. Then, azide-containing UPD-GalNAz reagent is enzymatically attached to the exposed GlcNAc on antibodies using the β-1,4-Galactosyltransferase Y289L (GalT) to generate an azide-functionalized antibody (commercially available from Genovis AB, Sweden). The azide-functionalized antibody can react with an alkyne-carrying reagent attached to beads, producing beads with Fc-immobilized antibody molecules ready for the DST assay.

In some embodiments, different antibody immobilization approaches known in the art can be employed. In preferred embodiments, coupling antibody molecules to a solid support (e.g., beads) should not result in the loss of its biological functionality, such as antigen binding, which can be achieved with oriented immobilization. Several functional moieties on the antibody surface can be utilized during coupling to beads, among them are lysine residues, cysteine residues and polysaccharides moieties. For example, amino groups on Lys residues are distributed over the entire antibody surface, and they have the capacity to react toward many reactive groups (aldehyde, tosyl and epoxy groups) without prior activation. Other examples include using carbodiimide conjugation to achieve amide bonds; using reducing reagents to break the disulfide groups and introduce antibody fragments with free sulfhydryl groups; using thiol-maleimide coupling to achieve site-direct immobilization. Various techniques to achieve site-specific and oriented immobilization of antibody molecules are disclosed, for example, in Shipeng Gao, et al., Oriented immobilization of antibodies onto sensing platforms—A critical review, Analytica Chimica Acta, 2021, 338907.

In some embodiments of the DST assay, the binding element configured to bind antibodies from the samples comprises the antigen. This format of the DST assay resembles a "sandwich" ELISA assay. In these embodiments, specific antibodies from the samples bind to the antigen and then are attached to beads or on a solid support. Then, immobilized antibodies are contacted with the antigen attached to a coding tag comprising identifying information regarding the antigen, wherein the antigen bind to the second antigen-recognizing region ("arm") of the antibody molecules. This increases assay specificity, since antigen identity identified after sequencing the released extended recording tags should match the antigen used during initial binding, if the binding was specific. In other embodiments, the binding element configured to bind antibodies from the samples does not comprise the antigen.

In some embodiments of the DST assay, antibodies (IgG, IgM, and IgA) from biological fluids, such as serum, plasma or blood, can be enriched from abundant components using immobilized Protein A/G fusion protein (Choe, W., et al., "Fc-Binding Ligands of Immunoglobulin G: An Overview of High Affinity Proteins and Peptides." Materials (Basel) (2016), 9(12). Protein A/G binds to all human subclasses of IgG, IgA, and IgM, as well as to mouse monoclonal IgGs and rabbit polyclonal IgGs. This feature makes it compatible with the non-human antibody controls. The attachment of sample-specific barcodes and DNA encoding technology to Protein A/G beads enables high-throughput biological analysis using NGS technology and enables population-scale studies with digital resolution (Kebschull, J. M. and A. M. Zador (2018). "Cellular barcoding: lineage tracing, screening and beyond." Nat Methods 15(11): 871-879).

Figure 4A:
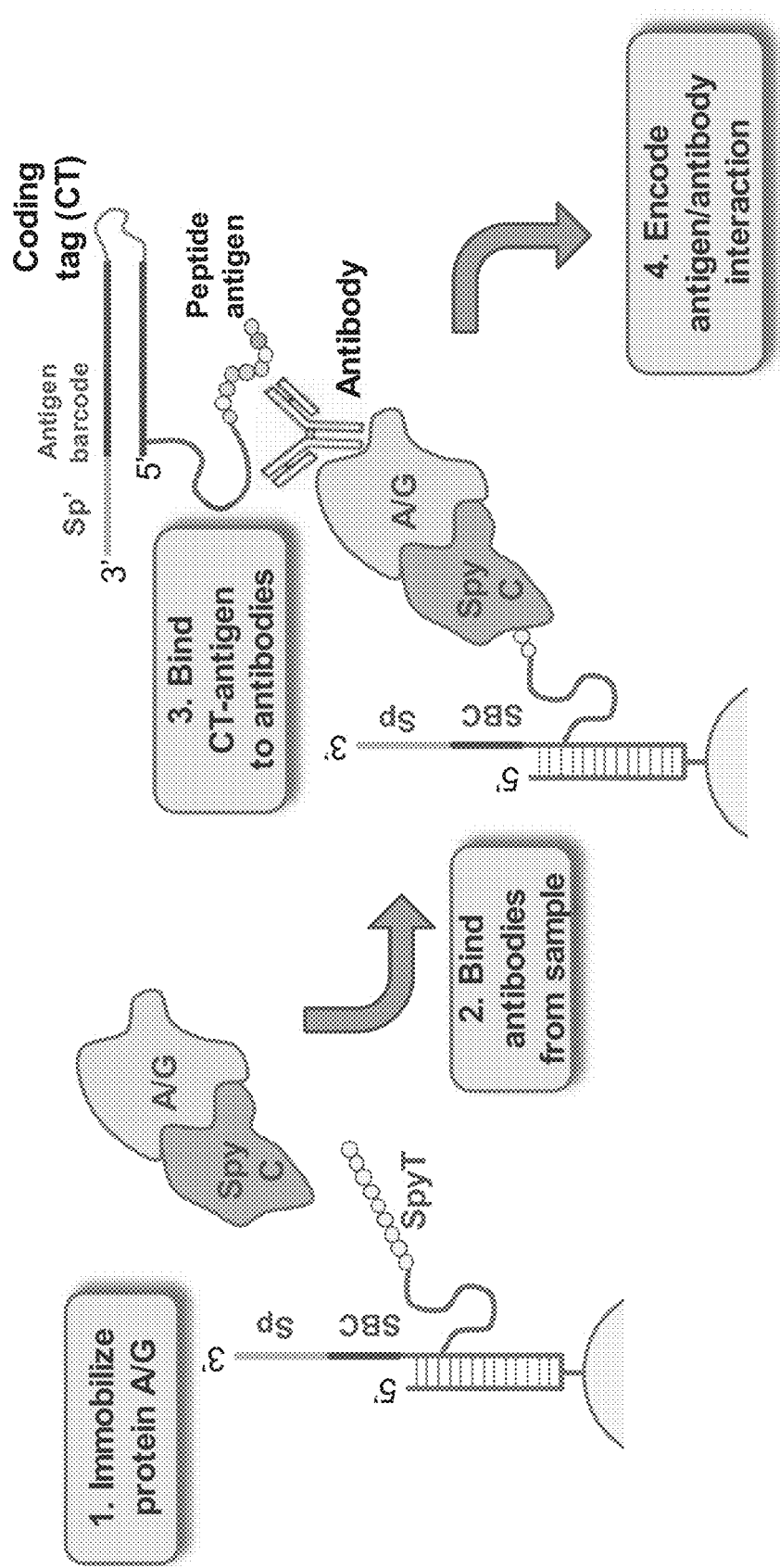
FIG. 4A. Exemplary design of the DST assay. Capture hairpin DNA comprising recording tag with sample-specific barcode (SBC) and spacer region (Sp) is attached on the DST bead. A SpyTag (SpyT) peptide (13 amino acids) is attached to the capture hairpin DNA. Next, the SpyC-Protein A/G fusion protein is covalently coupled via the SpyTag peptide (SpyT) to the capture DNA on the bead and is used to capture an antibody from a biological sample, such as a plasma or a serum sample. Next, the DST beads with the captured antibody is contacted with one or more antigens, wherein each antigen is attached to a coding tag (CT) comprising identifying information regarding the antigen (antigen barcode) and a complementary spacer region (Sp'). Next, following binding of a cognate antigen to the captured antibody, transfer of the identifying information regarding the antigen occurs via interaction between Sp-Sp' spacer regions followed by primer extension reaction, generating an extended recording tag comprising a portion complementary to the antigen-specific barcode, thereby encoding antigen/antibody interaction.
Figure 5A:
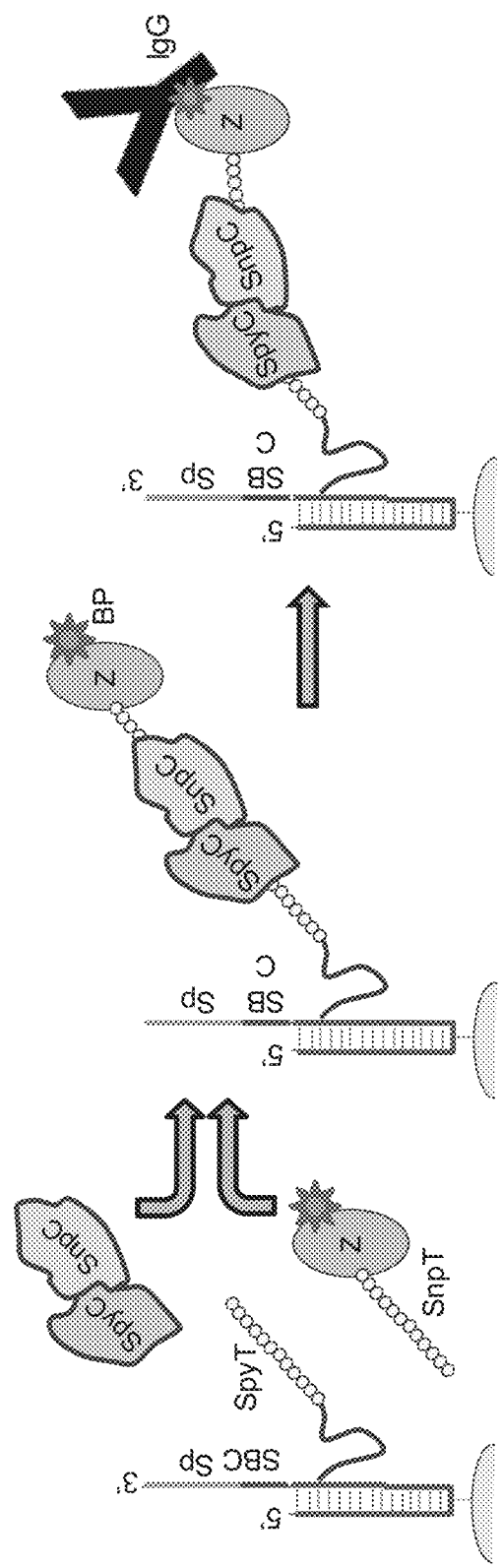
FIGS. 5A-5B. Exemplary design of DNA-barcoded antibody capture beads (DST beads).

In preferred embodiments of the DST assay, IgG, IgM, or IgA antibody molecules are enriched from a sample and coupled to barcoded DST beads comprising an immunoglobulin-binding protein. In some embodiments, coupling antibody molecules to DST beads is a covalent coupling. In some embodiments, covalent coupling is performed by crosslinking of the antibody molecules to the immunoglobulin-binding protein. In some embodiments, crosslinking is performed by addition of a reagent, such as photoaffinity probe or a crosslinking agent. In some embodiments, the binding element (e.g., immunoglobulin-binding protein) is attached to barcoded DST beads via SpyCatcher-SpyTag interaction. The SpyTag peptide forms an irreversible covalent bond to the SpyCatcher protein via a spontaneous isopeptide linkage, thereby offering a genetically encoded way to create a covalent linkage that resist force and harsh conditions. In a particular embodiment, the binding element is expressed as a fusion protein comprising the SpyCatcher protein (FIG. 4A). In other embodiments, the binding element (e.g., immunoglobulin-binding protein) is attached to barcoded DST beads via SnoopTag-SnoopCatcher peptide-protein interaction (FIG. 5A). The SnoopTag peptide forms an isopeptide bond with the SnoopCatcher protein. Details on conditions and properties of the SpyCatcher-SpyTag and SnoopTag-SnoopCatcher interactions are disclosed in U.S. Pat. Nos. 9,547,003 B2, 10,526,379 B2, 10,889,622 B2, 10,527,609 B2. In yet other embodiments, the binding element (e.g. immunoglobulin-binding protein) is attached to barcoded DST beads via the HaloTag® protein fusion tag and its chemical ligand. HaloTag is a modified haloalkane dehalogenase designed to covalently bind to synthetic ligands (HaloTag ligands). Details on conditions and properties of the HaloTag-based immobilization approach are disclosed in U.S. Pat. No. 10,604,745 B2, 10,246,690 B2, 10,101,332 B2, and 11,028,424 B2.

In some embodiments, the disclosed methods further comprise covalently cross-linking the antibodies from the samples to the binding element. In preferred embodiments, the cross-linking is achieved by adding a cross-linking reagent. The cross-linking can be either chemical or photo-crosslinking. In preferred embodiments, the binding element configured to bind antibodies comprises an immunoglobulin-binding protein. In these embodiments, protein-to-protein cross-linkers can be used for covalent attachment of antibody molecules to the immunoglobulin-binding protein. In one specific embodiment, such cross-linkers include the $SM(PEG)_n$ reagents, which are heterobifunctional cross-linkers with N-hydroxysuccinimide (NHS) ester and maleimide groups that allow covalent conjugation of amine- and sulfhydryl-containing molecules. PEG spacers present in the cross-linkers improve water solubility of conjugate, stabilizing its structure. Specific examples of these cross-linkers include NHS-PEG2-Maleimide (succinimidyl-RN-maleimidopropionamido)-diethyleneglycoll ester) and NHS-PEG6-Maleimide (succinimidyl-RN-maleimidopropionamido)-hexaethyleneglycoll ester).

In another embodiment, protein-to-protein cross-linker is BS3 (bis(sulfosuccinimidyl)suberate), an amine-to-amine crosslinker. BS3 contains an amine-reactive N-hydroxysulfosuccinimide (NHS) ester at each end of an 8-carbon spacer arm. NHS esters react with primary amines at pH 7-9 to form stable amide bonds, along with release of the N-hydroxysulfosuccinimide leaving group. Proteins, including antibodies, generally have several primary amines in the side chain of lysine (K) residues and the N-terminus of each polypeptide that are available as targets for NHS-ester crosslinking reagents.

In yet another embodiment, protein-to-protein cross-linker is DMP (dimethyl pimelimidate) that contains an amine-reactive imidoester group targeting primary amines at each end of a 7-atom spacer arm. Imidoesters react with amines at alkaline pH values (pH 8-10) to form amidine bond, which retains net charge character of protein primary amine to which it reacts. Other related cross-linkers include DMA (dimethyl adipimidate) and DMS (dimethyl suberimidate).

In some embodiments of the DST assay, each bead of the plurality of beads contacted with the sample comprises: i) a recording tag covalently attached to the bead and comprising a sample-specific barcode, and ii) an associated binding element covalently attached to the bead and configured to bind to a plurality of different antibodies in the sample. In some embodiments, obtaining a plurality of antibody-bound beads comprises obtaining a plurality of beads each comprising antibodies from a sample covalently attached to the bead.

In some embodiments of the DST assay, the plurality of samples comprises at least 5 samples. In some embodiments of the DST assay, the plurality of samples comprises at least 10 samples. In some embodiments of the DST assay, the plurality of samples comprises at least 100 samples. In some embodiments of the DST assay, the plurality of samples comprises at least 3, 5, 10, 15, 20, 25, 30, 40, 48, 50, 60, 70, 80, 98, 100, 150, 200 samples. In some embodiments, each sample from the plurality of samples is obtained from a different subject from the plurality of subjects, allowing for assessing level(s) of an antibody or antibodies in multiple subjects at the same time (in a single reaction). In some embodiments, at least a fraction of samples (e.g., at least 2 samples, at least 3 samples, at least 5 samples, at least 10 samples, at least 100 samples, at least 200 samples, or up to 1000 samples) from the plurality of samples is obtained from a unique subject (individual) from the plurality of subjects. In some embodiments, the extended recording tag or the extended coding tag is amplified and additionally indexed during the amplification. In some embodiments, an additional stage of sample indexing is employed at the amplification step of the extended recording tag or the extended coding tag to combinatorically increase the possible number of samples that can be sequenced in a single NGS run. This additional stage of indexing could be row/column indexing of a 96-well filter plate in which 384 samples are indexed per well at the bead level and then indexed across the reaction plate generating a total number of indexed samples of 384×96=36,864 indexed samples in a single NGS run.

In some embodiments of the DST assay, sample is a biological sample. In some embodiments, each biological sample of the plurality of biological samples comprises blood, plasma, serum, urine and/or saliva. In some embodiments of the DST assay, biological sample can be any biological fluid comprising antibodies. In some embodiments of the DST assay, biological sample can be a dry blood spot, or any other form of a preserved biological fluid comprising antibodies that is used for transportation or storage.

In some embodiments of the DST assay, the plurality of samples comprise samples obtained from one or more subjects. For example, one or more samples may be obtained from the same subject taken from different timepoints and/or different tissues and/or after different treatments, and so on. Additional sample(s) may include samples obtained from a second subject (different from the first subject), optionally taken from different timepoints and/or different tissues and/or after different treatment, and so on. In some embodiments, the plurality of samples comprising at least one antibody is obtained by processing and/or purifying biological samples obtained from a plurality of subjects. In some embodiments, each sample of the plurality of samples is obtained from a different subject.

The plurality of samples can comprise samples obtained from the same subject, for instance, from different tissues or organs of the subject and/or at different time points.

In some embodiments, two samples obtained from the same subject can be separately contacted with a first plurality of beads comprising a first sample-specific barcode and with a second plurality of beads comprising a second sample-specific barcode, respectively, where the first and second sample-specific barcodes are different nucleic acid barcodes. Sample analysis using the first and second sample-specific barcodes can be compared and used to validate the assay.

In some embodiments of the DST assay, the antigen comprises a peptide sequence from an influenza virus, and the method detects an antibody that binds to the peptide sequence derived from the influenza virus. These embodiments can be used to provide diagnostics or serotyping for the influenza infection in patients (subjects). In some embodiments, the plurality of binding agents comprises peptide sequences from a H1N1 flu virus (swine flu), such as any one of the sequences set forth in SEQ ID NO: 23-SEQ ID NO: 34.

In some embodiments of the DST assay, the antigen comprises a peptide sequence from a SARS-CoV-2 virus, and the method detects an antibody that binds to the peptide sequence derived from the SARS-CoV-2 virus. These embodiments can be used to provide diagnostics or serotyping (analysis of previous exposures to the virus) for the COVID-19 infection in patients (subjects). In some embodiments, the plurality of binding agents comprises peptide sequences from a SARS-CoV-2 spike (S) protein, a SARS-CoV-2 Envelope (E) protein, a SARS-CoV-2 Membrane (M) protein, and/or a SARS-CoV-2 Nucleocapsid (N) protein, such as any one of the sequences set forth in SEQ ID NO: 4-SEQ ID NO: 13. In some embodiments, the plurality of binding agents comprises peptide sequences from a SARS-CoV-2 spike (S) protein, such as any one of the sequences set forth in SEQ ID NO: 4-SEQ ID NO: 8.

In some embodiments of the DST assay, the antigen comprises a peptide sequence from a pathogen different from SARS-CoV-2 virus or influenza virus. Antigen information for this pathogen may be extracted from public resources known to the skilled in the art, and methods disclosed herein can be utilized to set up a DST assay to detect exposure to this pathogen among multiple subjects.

Standard techniques known in the art can be used to collect, preserve and prepare biological samples for the DST assay. In one example, saliva sample containing antibody is prepared as follows (based on Isho B, et al., Persistence of serum and saliva antibody responses to SARS-CoV-2 spike antigens in COVID-19 patients. Sci Immunol. 2020 Oct. 8; 5(52):eabe5511). Salivette® tubes are used to collect samples according to manufacturer instructions (Sarstedt). These tubes include a cotton swab that subjects are instructed to chew for set amount of time. The swab is then transferred into an inner tube which is then inserted into an outer tube that catches liquid saliva upon centrifugation at 1000×g for 3 min (Centrifuge 5910 R, Eppendorf). Salivary flow is controlled by establishing a fixed amount of collection time (2 min) for each subject. Prior to saliva collection, subjects are fasted, refrained from taking oral medication, and are not brushed their teeth for a minimum of 30 min.

In some embodiments, collected biological samples, such as serum or saliva samples, undergo pathogen inactivation. A variety of methods for pathogen inactivation are known and can be utilized. For example, envelop viruses are inactivated in non-ionic detergents, such as Triton® X-100. For example, 10% Triton X-100 is added to the collected biological samples to a final dilution of 1% Triton X-100 and incubated for 1 hour at room temperature. Inactivated samples can be immediately frozen and stored at −80° C. In some embodiments, heat inactivation is not recommended, as it can destroy IgG and IgA molecules.

Timing of biological sample collection from subjects can be important for antibody detection. Typically, IgA and IgM antibodies undergo rapid decay after infection, while IgG antibodies remain relatively stable up to 3-4 months after an acute infection. For example, serum and saliva IgG antibodies to SARS-CoV-2 are maintained in the majority of COVID-19 patients for at least 3 months after infection; and IgG responses in saliva may serve as a surrogate measure of systemic immunity to SARS-CoV-2 based on their correlation with serum IgG responses (Isho B, et al., Persistence of serum and saliva antibody responses to SARS-CoV-2 spike antigens in COVID-19 patients. Sci Immunol. 2020 Oct. 8; 5(52):eabe5511).

In some embodiments of the DST assay, the antigen is or comprises a polypeptide comprising an amino acid sequence from 5 to 1000 amino acid residues, and comprises one or more epitopes for antibody binding. In some embodiments, the antigen is or comprises a peptide comprising an amino acid sequence from 5 to 60 amino acid residues, from 7 to 30 amino acid residues, from 7 to 20 amino acid residues, from 10 to 30 amino acid residues, or having 5, 6, 7, 8, 9, 10, 11, 12, 13, 14, 15, 16, 17, 18, 19, 20, 25 or 30 amino acid residues in length.

In some embodiments of the DST assay, the plurality of binding agents comprises portions from the same biological molecule and/or portions from different biological molecules. For example, two or more different antigens can be obtained from the same biological molecule (such as, for example, a viral protein) and each can be separately attached to a coding tag comprising an encoder sequence that comprises identifying information regarding the attached antigen. Having two or more different antigens for the same pathogen may be beneficial for increasing sensitivity and/or specificity of the DST assay.

In some embodiments of the DST assay, the binding element is configured to bind to an antibody constant region, optionally wherein the binding element comprises an immunoglobulin Fc-binding domain and is not configured to bind to an antibody variable region.

In some embodiments, the DST assay further comprises covalently cross-linking the antibodies to the binding element in the plurality of antibody-bound beads in a).

In some embodiments of the DST assay, in c), the mixture of beads is contacted with a plurality of binding agents each comprising a different antigen, wherein each different antigen is attached to a different coding tag comprising an encoder sequence that comprises identifying information regarding the antigen attached thereto.

In some embodiments of the DST assay, the antigen comprises a peptide sequence from a SARS-CoV-2 virus, and the method detects an antibody that binds to the peptide sequence.

In some embodiments of the DST assay, the plurality of binding agents comprises peptide sequences from a SARS-CoV-2 spike (S) protein, a SARS-CoV-2 Envelope (E) protein, a SARS-CoV-2 Membrane (M) protein, and/or a SARS-CoV-2 Nucleocapsid (N) protein.

In some embodiments of the DST assay, the plurality of binding agents comprises peptide sequences from a SARS-CoV-2 spike (S) protein.

In some embodiments of the DST assay, for each binding agent of the plurality of binding agents, the antigen is attached to the coding tag using mRNA or cDNA display.

In some embodiments of the DST assay, presence/absence, level, and/or activity the antibody to the antigen in the sample is/are analyzed in e).

In some embodiments of the DST assay, following binding of the antigen to the antibody, the transfer of identifying information occurs from the coding tag to the recording tag associated with the binding element bound to the antibody, thereby generating the extended recording tag, and wherein the encoder sequence or the complement thereof in the extended recording tag is analyzed in e).

In some embodiments of the DST assay, comprising capping the extended recording tag with a polynucleotide that comprises a universal priming site for sequencing, and the capping comprises hybridizing and/or ligating the polynucleotide to the extended recording tag.

In some embodiments of the DST assay, the binding agent is a first binding agent, the method further comprising contacting the mixture of beads with a second binding agent comprising an antibody-binding portion, and (i) a second coding tag comprising identifying information regarding the antibody-binding portion, or (ii) a detectable label; and the method comprises transferring the identifying information in the second coding tag to the extended recording tag to generate a further extended recording tag, or detecting the detectable label.

In some embodiments of the DST assay, the antibody-binding portion is configured to bind to an antibody variable region, and the mixture of beads is contacted with the second binding agent after contacting with the first binding agent and generating the extended recording tag. In some embodiments of the DST assay, the antibody-binding portion is an antigen or an anti-idiotypic antibody. In some embodiments of the DST assay, the antibody-binding portion is configured to bind to an antibody constant region, and the mixture of beads is contacted with the second binding agent before or after generating the extended recording tag.

In some embodiments of the DST assay, in c), the binding agent comprises two identical antigens joined together, optionally by a linker, and the encoder sequence in the coding tag of the binding agent comprises identifying information regarding the identical antigen.

In some preferred embodiments of the DST assay, the transfer of identifying information during the encoding cycle occurs by a DNA polymerase having 5'->3' polymerization activity and devoid of 3'->5' exonuclease activity. Several of many examples of such polymerases include Klenow exo- (Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, 9° N Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs). In other embodiments of the DST assay, the transfer of information occurs by a DNA ligase.

In some preferred embodiments of the DST assay, the disclosed methods further comprise an optional capping step after the final encoding cycle, wherein the capping step comprises contacting the one or more extended recording tags, extended after the final encoding cycle, with a polynucleotide that comprise a universal priming site for sequencing and is configured to either hybridize with a portion of the extended recording tags, or ligate to the extended recording tags. Such capping step effectively reduces size of coding tags conjugated to antigens and simplifies the following NGS of the extended recording tags. Such capping step also allows to reduce a background signal during information transfer step by reducing non-specific DNA-DNA interactions. In other embodiments of the DST assay, there is no capping step after the final encoding cycle, and a universal priming site used for sequencing the extended recording tags during the analysis step is present in coding tags conjugated to the antigens used in the DST assay.

In some embodiments of the DST assay, in c) (the antigen-contacting step) the mixture of beads is contacted with two different antigens; each antigen is attached to a corresponding coding tag comprising identifying information regarding the attached antigen; and the levels of at least two antibodies that bind two different antigens in the plurality of subjects are assessed by the method. In some cases, these two different antigens are components of two different animal pathogens. In some embodiments, in c) the mixture of beads is contacted with a plurality of different antigens; each antigen is attached to a coding tag comprising identifying information regarding the attached antigen; and the levels of antibodies that bind antigens from the plurality of different antigens in the plurality of subjects are detected (assessed) by the method. In some embodiments, the plurality of different antigens comprises at least three different antigens. In some embodiments, these at least three different antigens are components of three different animal pathogens. In some embodiments, the plurality of different antigens comprises at least 4, 5, 6, 7, 8, 9, 10, 20 or more different antigens. In some embodiments of the DST assay, the antigen comprises a portion of a SARS-CoV-2 viral protein, and level of antibodies that bind to the SARS-CoV-2 virus is assessed by the DST assay.

Figure 8:
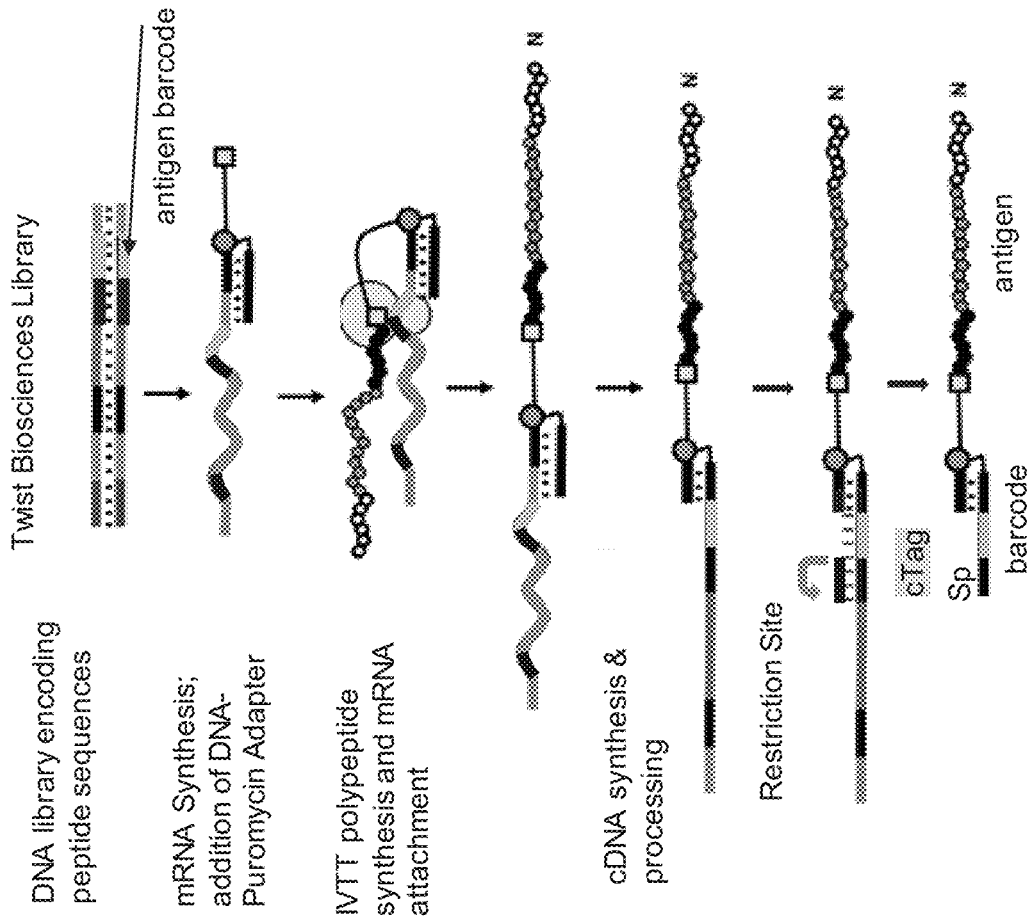
FIG. 8. Generating exemplary antigen-coding tag conjugates using cDNA display. A comprehensive set of peptide antigens to various pathogens and their subtypes can be generated using in situ DNA synthesis technology (Twist Biosciences) combined with standard cDNA display technology. For optimal encoding efficiency, the cDNA sequence can employ a clone-specific barcode such that the cDNA sequence is removed (via restriction digestion) prior to the DST assay and encoding.
Figure 10:
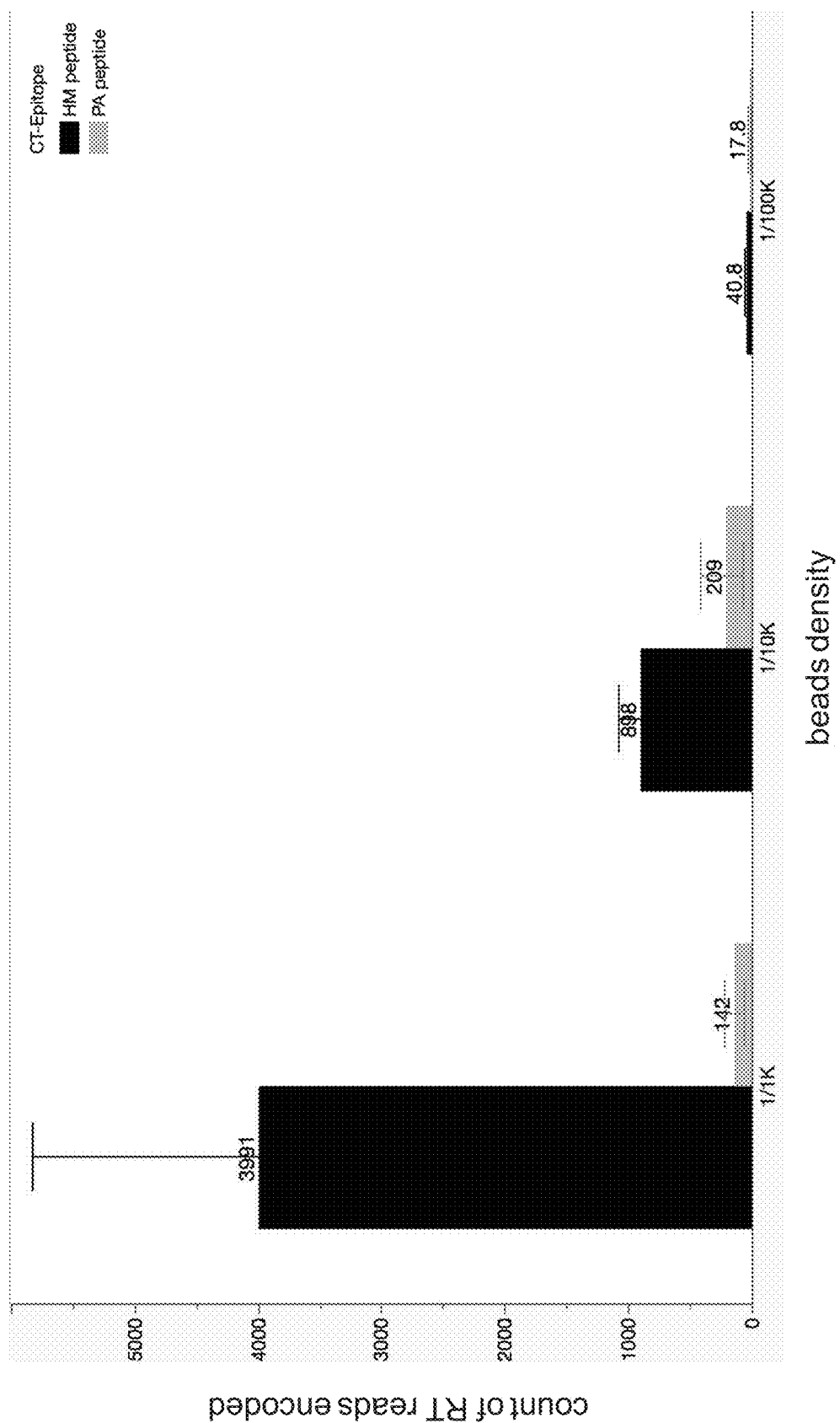
FIG. 10. Exemplary impact of recording tag density on encoding signal. Beads density is presented as the fraction of reactive sites conjugated with a recording tag relative to total number of the reactive sites. The target epitopes are HM peptide and PA peptide used at 2 nM. Fusion protein—AG-SC.
Figure 11:
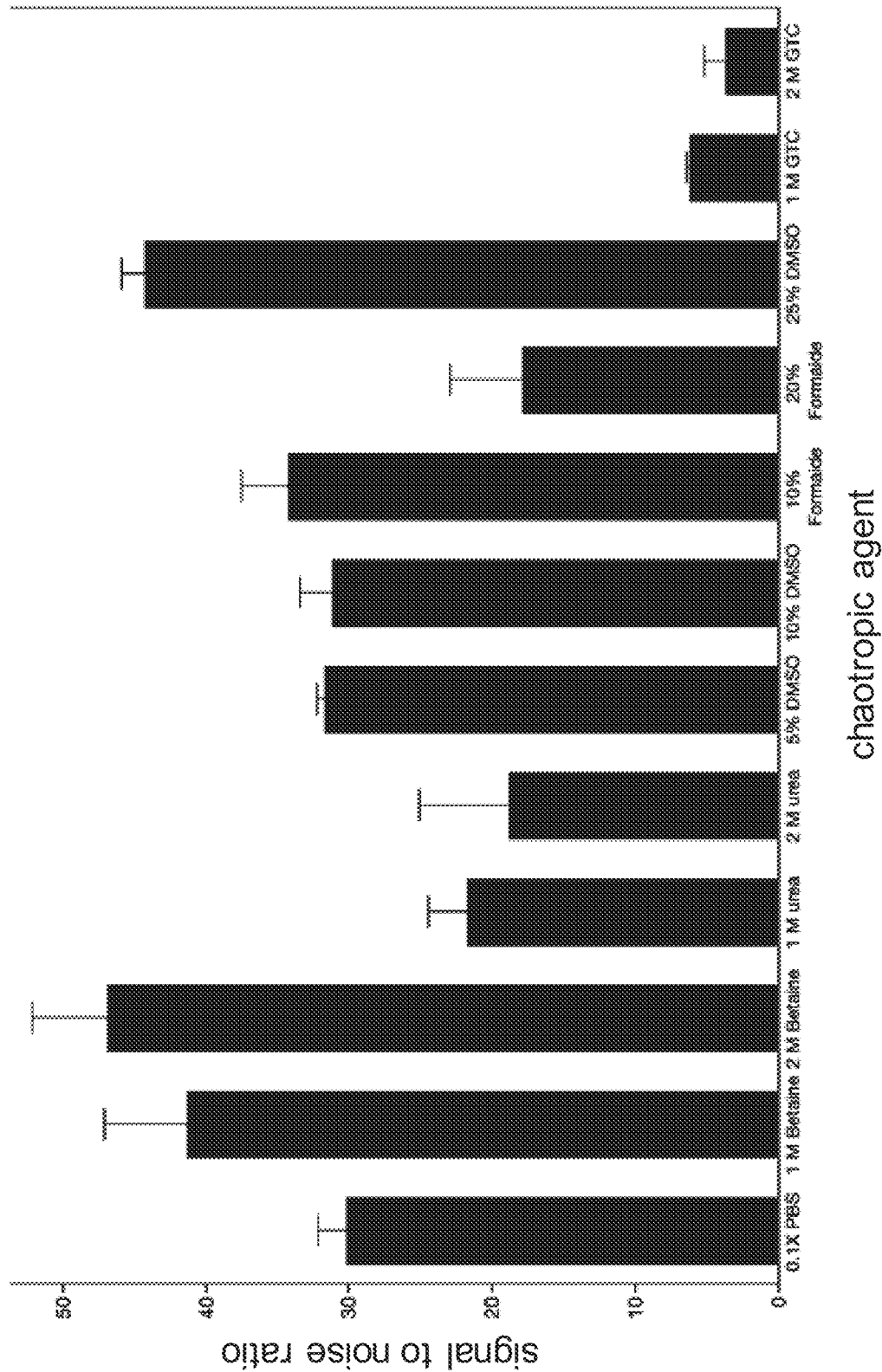
FIG. 11. Exemplary impact of wash buffer composition on encoding signal-to-noise ratio in serum background. Additions of different chaotropic agents were tested.
Figure 12:
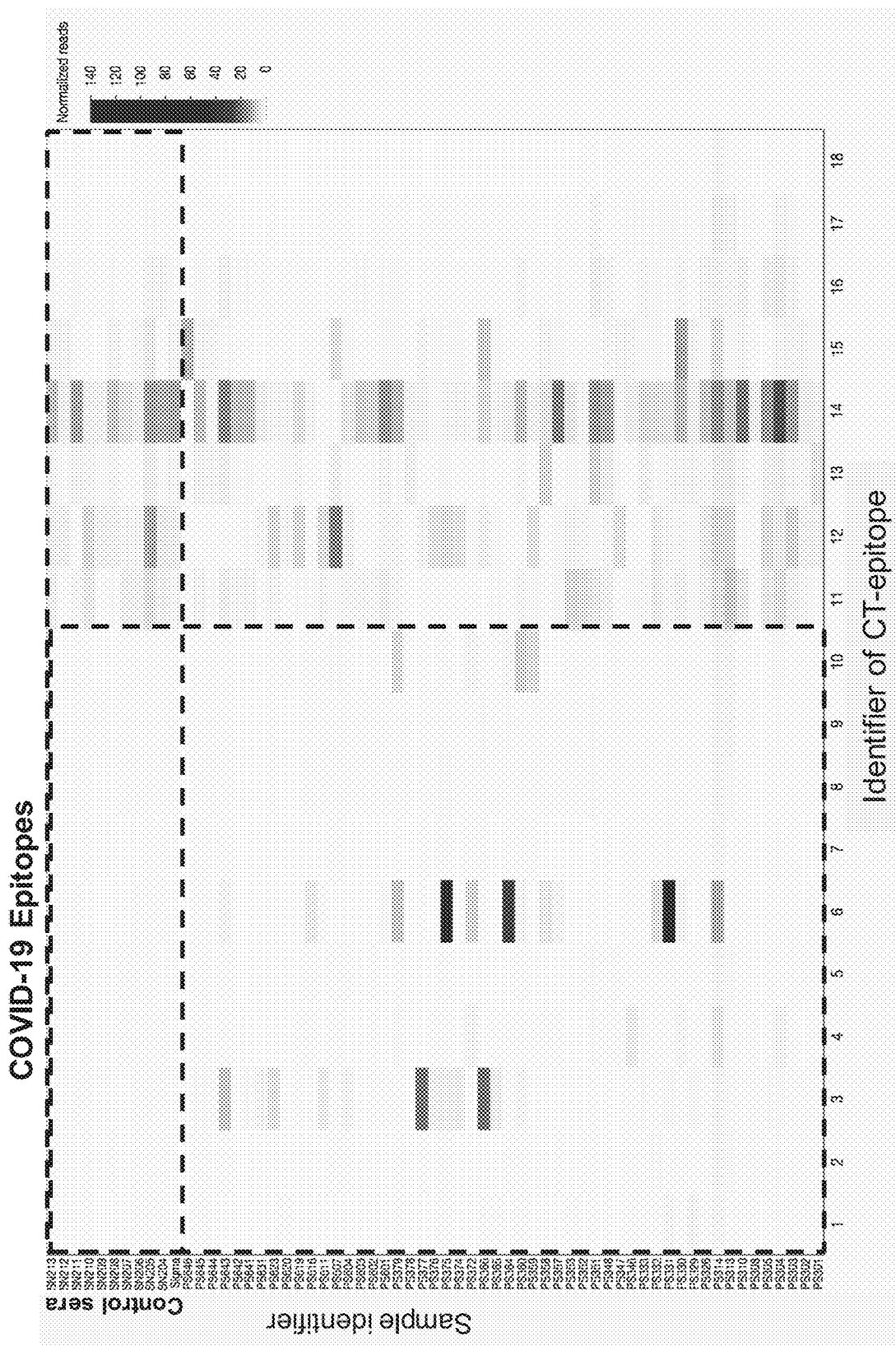
FIG. 12. Exemplary virus serotyping using the DST assay. Multiple control sera and confirmed COVID-19 positive sera were analyzed using a panel of peptide antigen-coding tag conjugates corresponding to linear viral epitopes from a number of viruses (see Table 1). Data are presented as a heat map based on the number of encoded interactions for a given linear viral epitope in each sample (defined as the number of reads). Normalized encoding signal across multiple epitopes and serum donors are shown. Control sera were collected prior to the COVID-19 pandemic. Control sera signals are highlighted with a horizontal dashed box. COVID-19 specific epitopes are also highlighted with a vertical dashed box.
Figure 13A:
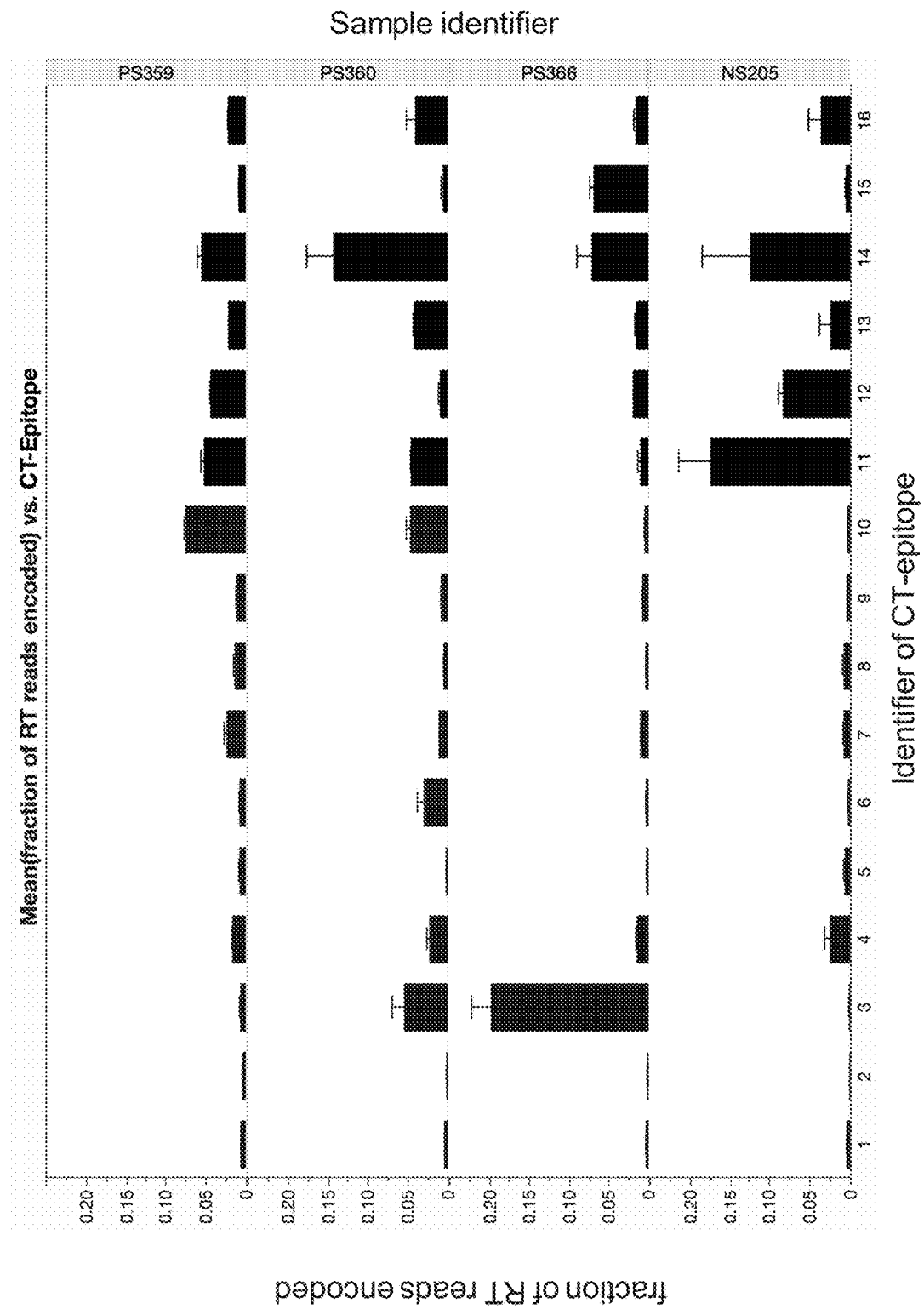
FIGS. 13A-13B. Exemplary multiplexed sample crosstalk. Sample multiplexing was evaluated by combination of specific serum samples on different recording tags. Description of peptide epitopes used in this experiment is provided in Table 1. The four panels in FIG. 13A demonstrate signal from individual samples; the four panels in FIG. 13B illustrate data resulting from the pooling of specific samples prior to the encoding assay. Several serum samples were analyzed both individually and in various combinations to determine the potential for cross-talk between sample-specific barcoded DST beads. All sera antibodies were first attached to specific, barcoded DST beads and washed to remove excess material. Encoding reactions were then performed using a viral antigen panel on both individual and combined samples.
Figure 13B:
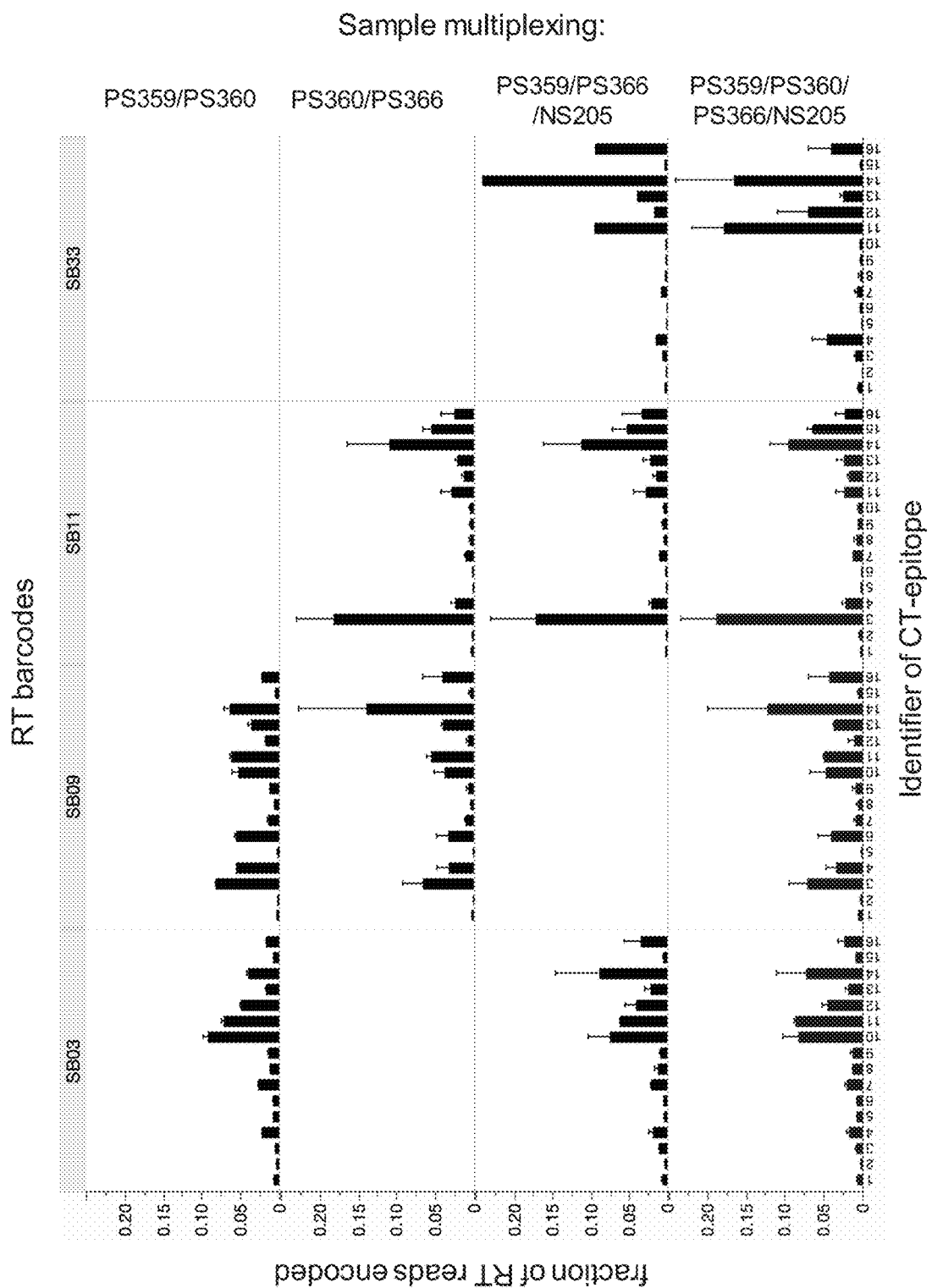

In some embodiments of the DST assay, each antigen of the plurality of different antigens attached to a coding tag comprising identifying information regarding the attached antigen is generated by mRNA or cDNA display. Exemplary way of generating antigen-coding tag conjugates by mRNA or cDNA display is shown in FIG. 8. The ability to explore a large number of antigens across a large population of patient samples enables selection a compact set of the most informative antigens in the serotyping assay. The optimized peptide sequences of interest will be determined by tiling peptides through the pathogen proteins of interest (POI) or using known/published epitopes. The set of peptide of interest can be generated by high-throughput peptide synthesis or alternatively using cDNA display technology for displaying and encoding peptides that can be used in the DST assay (FIG. 8). These capabilities enable us to easily make thousands of DNA-peptide chimeras targeted to any given pathogen or set of pathogens. In other embodiments of the DST assay, antigen-coding tag conjugates are generated by other methods, such as direct chemical conjugation between antigen and nucleic acid coding tag by click chemistry tools, or by SpyCatcher-SpyTag interaction. For example, recombinant antigen is prepared as a fusion with the SpyCatcher, nucleic acid coding tag is terminally coupled to the SpyTag, and then an irreversible binding between them is initiated. Some other potential ways of generating antigen-coding tag conjugates are disclosed in US 2020/0348308 A1 and in the Examples below.

In some embodiments of the DST assay, in c) (the antigen-contacting step) the mixture of beads is contacted with two identical antigens joined together, optionally by a linker, and the two identical antigens are attached to a coding tag comprising identifying information regarding one of the identical antigens. This tandem antigen format can increase sensitivity or specificity of the assay, since it effectively increases avidity between the cognate antibody and the antigen, and stability of the formed complex between them, which could be increase efficiency of the information transfer. A linker between two identical antigens can be any flexible linker that would not interfere with antigen conformation or ability to interact with the antibody. Preferably, such linker provides a spacing distance between two antigens that matches the distance between two antigen-recognizing regions ("arms") of the antibody molecule. In other embodiments of the DST assay, only single antigen attached to a corresponding coding tag is used in the assay.

In some embodiments of the DST assay, each of the plurality of samples is independently selected from the group consisting of blood, plasma, serum, urine, and saliva samples.

In some embodiments of the DST assay, detecting the antibody in the sample is performed at a limit of detection (LOD) below 100 pM, preferably between about 1 pM and about 100 pM, more preferably between about 1 pM and about 10 pM.

In some embodiments of the DST assay, detecting the antibody in the sample is performed at a signal-to-noise ratio (SNR) of at least or about 3. In some embodiments, the SNR of detecting multiple different antibodies in the plurality of samples is at least or about 10, at least or about 15, at least or about 20, at least or about 25, at least or about 30, at least or about 35, at least or about 40, at least or about 45, or at least or about 50.

In some embodiments of the DST assay, each bead of the mixture of beads is a porous bead. Porous beads are beads having pore structures or empty channels through which molecules can pass. In some embodiments, porous beads are microspheres. In some embodiments, porous beads are beads having pore structures or empty channels through which antibody molecules from samples and binding agents can pass. Using such porous beads is advantageous, since porous beads have significantly increased surface area, where antibodies may be attached and contacted with binding agents. Multiple examples of porous beads are known in the art, such as made of crosslinked polysaccharide polymers (e.g., sepharose), polymer microspheres and silica beads. Exemplary polymer non-agarose-based microspheres comprise TSKgel Ether-5PW beads (made from polymethacrylate material bonded with polyether groups and having ~100 nm pore size) and POROS beads (Thermo Scientific; incompressible beads with cross-linked polystyrene-divinylbenzene backbone having ~100-360 nm pore size). The average pore size for POROS is. Exemplary size ranges for porous beads comprise 20-50 um, 20-70 um, and 70-50 um. Exemplary pore size ranges comprise 20-70 nm, 30-70 nm, 40-70 nm, 70-100 nm and 100-360 nm.

In preferred embodiments, beads used in the DST assay do not interact unspecifically with proteins (such as antibodies) or other sample components.

In some embodiments of the DST assay, all or vast majority of beads in the mixture of beads are sufficiently uniform and have approximately the same dimensions or size (all beads in the pluralities of beads and in the mixture of beads are essentially homogenous). This would limit inconsistencies in the following transfer of identifying information, which may be created when population of beads is heterogeneous.

In some embodiments of the DST assay, the mixture of beads comprising immobilized antibodies is contacted with more than one antigen, wherein each antigen attached to a coding tag comprising identifying information regarding the antigen. In some embodiments, the first antigen and second antigen, and optionally any further order antigens, can be first pooled together and added to the mixture of beads comprising immobilized antibodies, or can be added simultaneously to the mixture of beads without prior pooling. In other embodiments, the first antigen and second antigen, and optionally any further order antigens, are each contacted with the mixture of beads comprising immobilized antibodies in separate binding cycles, added in sequential order. In certain embodiments, multiple antigens are used at the same time in parallel. This parallel approach saves time and reduces non-specific binding by non-cognate antigens to a site that is bound by a cognate antigen (because the antigens are in competition).

In some embodiments of the DST assay, the certain level or the presence of the antibody in a subject indicates that the subject has been exposed to a pathogen that comprises the antigen. In some embodiments, the certain level or the presence of the antibody in a subject indicates that the subject has currently a pathological condition, or had a pathological condition in the past.

In some embodiments, the pathogen includes a bacterium, a virus, a parasite, a protozoan, a protist, or a fungus. In some embodiments, the pathogen is a mammalian pathogen (affects a mammal) In preferred embodiments, the pathogen is a human pathogen. In some embodiments, the pathogen includes a member of one the genera *Yersinia, Klebsiella, Providencia, Erwinia, Enterobacter, Salmonella, Serratia, Aerobacter, Escherichia, Pseudomonas, Shigella, Vibrio, Aeromonas, Streptococcus, Staphylococcus, Micrococcus, Moraxella, Bacillus, Clostridium, Corynebacterium, Eberthella, Francisella, Haemophilus, Bacteroides, Listeria, Erysipelothrix, Acinetobacter, Brucella, Pasteurella, Flavobacterium, Fusobacterium, Streptobacillus, Calymmatobacterium, Legionella, Treponema, Borrelia, Leptospira, Actinomyces, Nocardia, Rickettsia, Micrococcus, Mycobacterium, Neisseria,* or *Campylobacter*. In some embodiments, the pathogen includes SARS-CoV-2 (Severe acute respiratory syndrome-related coronavirus 2), a Papilloma virus, a Parvovirus, an Adenovirus, a Herpesviruse, a Vaccine virus, an Arenavirus, a Coronavirus, a Rhinovirus, a Respiratory syncytial virus, an Influenza virus, a Picornavirus, a Paramyxovirus, a Reovirus, a Retrovirus, a Rhabdovirus, or human immunodeficiency virus (HIV). Alternatively, the pathogen may be, for example, a member of one of the genera *Taenia, Hymenolepis, Diphyllobothrium, Echinococcus, Fasciolopsis, Heterophyes, Metagonimus, Clonorchis, Fasciola, Paragonimus, Schistosoma, Enterobius, Trichuris, Ascaris, Ancylostoma, Necator, Wuchereria, Brugi, Loa, Onchocerca, Dracunculus, Naegleria, Acanthamoeba, Plasmodium, Trypanosoma, Leishmania, Toxoplasma, Entamoeba, Giardia, Isospora, Cryptosporidium, Enterocytozoa, Strongyloides,* or *Trichinella*. In some embodiments, the pathogen is a fungus that is the causative agent of a condition such as, for example, Ringworm, Histoplasmosis, Blastomycosis, Aspergillosis, Cryptococcosis, Sporotrichosis, Coccidiodomycosis, Paracoccidioidomycosis, Mucomycosis, Candidiasis, Dermatophytosis, Protothecosis, Pityriasis, Mycetoma, Paracoccidiodomycosis, Phaeohphomycosis, Pseudallescheriasis, Trichosporosis, or Pneumocystis. The recited lists serve only as representative groups and should not be interpreted as an exclusive list.

In some embodiments, allowing transfer of the identifying information regarding the antigen from the coding tag to the recording tag in d) comprises providing conditions to allow the transfer, such as adding an enzyme (such as DNA polymerase or DNA ligase) to the immobilized polypeptide, as well as an appropriate buffer for this enzyme (such as a buffer for DNA polymerase or DNA ligase). Standard buffers that provide functionality of DNA polymerase or DNA ligase are known in the art. In some embodiments, allowing transfer of the identifying information regarding the antigen from the coding tag to the recording tag in d) additionally comprises having a relatively high affinity interaction between the antigen and the cognate antibody to allow sufficient time for primer extension reaction or ligation reaction to occur while the antigen and the cognate antibody are in a sufficient proximity (avoiding premature separation or dissociation of the coding tag and the recording tag.

In preferred embodiments, to provide the DST assay specificity, transfer of the identifying information regarding the antigen from the coding tag of the antigen to a recording tag associated with an immobilized antibody occurs only following (or after) binding of the antigen to the immobilized antibody. Binding of the antigen to the immobilized antibody should not depend on the presence of the recording tag associated with the immobilized antibody.

In preferred embodiments, to provide the DST assay specificity, the coding tag of an antigen and the recording tag associated with an antibody are not configured to interact strongly with each other unless brought to proximity by specific interaction between the antigen and the cognate antibody that recognizes the antigen. Thus, binding interaction between the antigen-coding tag conjugate and the immobilized recording tag-antibody conjugate is mostly driven by binding interaction between the antigen and the antibody, and not by the coding tag and the recording tag. This can be achieved by optimizing portions of the coding tag and the recording tag configured to interact with each other. In some embodiments, the coding tag and the recording tag have single stranded DNA spacer regions that are complementary to each other and configured to interact via nucleic acid hybridization (see FIG. 2B). In these embodiments, such spacer regions are designed to be of a specific length. In preferred embodiments, lengths of the complementary spacer regions are 6 nucleotides (nt), 7 nt or 8 nt.

In preferred embodiments of the DST assay, the binding element can be associated with or attached to the recording tag before contacting each biological sample with a plurality of beads, or with a recording tag comprising a sample-specific barcode. In other embodiments of the DST assay, the binding element and recording tag can be independently attached to each bead of the plurality of beads, and not attached to each other before contacting. In yet other embodiments of the DST assay, the binding element and recording tag can independently contact antibodies.

In preferred embodiments of the DST assay, transfer of the identifying information regarding the antigen occurs from the coding tag to the recording tag associated with the cognate immobilized antibody, thereby generating an extended recording tag.

In some embodiments of the DST assay, in order to obtain a plurality of antibody-bound beads from each sample of a plurality of samples, each sample is contacted (separately from other samples) with a plurality of beads, wherein each bead of the plurality of beads contacted with the sample comprises: i) a recording tag comprising a sample-specific barcode, and ii) an associated binding element configured to bind to a plurality of different antibodies in the sample. The binding element may be associated with the recording tag directly or indirectly (e.g., via a linker or via the bead). For example, the binding element and the recording tag may be independently attached to the bead in proximity to each other to allow transfer of identifying information between the coding tag of the binding agent interacting with antibody attached to the binding element and the recording tag of the bead. In some embodiments, the binding element and the recording tag may be directly attached to each other using covalent bond(s) and/or non-covalent interaction(s).

In preferred embodiments, mixing the antibodies bound to the recording tag and to the binding element from different samples obtained the previous step together, and immobilizing the antibodies on a solid support comprises bringing the recording tag-antibody conjugate into proximity with a solid support by hybridizing the recording tag of the conjugate to a capture nucleic acid attached to the solid support; and covalently coupling the recording tag-antibody conjugate to the solid support. In some embodiments, the covalent coupling is achieved by a DNA ligase.

In some embodiments, the nucleic acid recording tag is associated directly or indirectly to the antibody via a non-nucleotide chemical moiety.

In some embodiments, the antibody is attached to the 3' end of the nucleic acid recording tag. In other embodiments, the antibody is attached to the 5' end of the nucleic acid recording tag. In yet other embodiments, the antibody is attached to an internal position of the nucleic acid recording tag.

In some embodiments, the recording tag is covalently attached to the antibody to generate the recording tag-antibody conjugate. In some embodiments, the recording tag and/or capture nucleic acid further comprises a universal priming site, wherein the universal priming site comprises a priming site for amplification, sequencing, or both.

In some embodiments, the capture nucleic acid (e.g., capture DNA) is used to immobilize antibodies or recording tags on a solid support. In some embodiments, the capture nucleic acid is derivatized or comprises a moiety (e.g., a reactive coupling moiety) to allow binding to a solid support. In some embodiments, the capture nucleic acid comprises a moiety (e.g., a reactive coupling moiety) to allow binding to the recording tag. In some other embodiments, the recording tag and/or antibody is derivatized or comprises a moiety (e.g., a reactive coupling moiety) to allow binding to a solid support. Methods of derivatizing a nucleic acid for binding to a solid support and reagents for accomplishing the same are known in the art. For this purpose, any reaction which is preferably rapid and substantially irreversible can be used to attach nucleic acids to the solid support. The capture nucleic acid may be bound to a solid support through covalent or non-covalent bonds. In a particular embodiment, the capture nucleic acid is covalently bound to biotin to form a biotinylated conjugate. The biotinylated conjugate is then bound to a solid surface, for example, by binding to a solid, insoluble support derivatized with avidin or streptavidin. In some embodiments, the capture DNA contains a hairpin (loop) region. The capture nucleic acid can be derivatized for binding to a solid support by incorporating modified nucleic acids in the loop region. In other embodiments, the capture moiety is derivatized in a region other than the loop region.

Exemplary bioorthogonal reactions that can be used for binding to a solid support or for generating nucleic acid-antibody conjugates include the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitron cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothioscyanate, an aldehyde, an epoxide, or the like. In some embodiments, iEDDA click chemistry is used for immobilizing polypeptides to a solid support or for generating nucleic acid-polypeptide conjugates since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction.

In some embodiments, a plurality of capture nucleic acids are coupled to the solid support. In some cases, the sequence region that is complementary to the recording tag on the capture nucleic acids is the same among the plurality of capture nucleic acids. In some cases, the recording tag attached to various polypeptides comprises the same complementary sequence to the capture nucleic acid.

In some embodiments of the DST assay, following binding of the antigen to the antibody, the transfer of identifying information occurs from the coding tag to the recording tag associated with the binding element bound to the antibody, thereby generating the extended recording tag, and wherein the encoder sequence or the complement thereof in the extended recording tag is analyzed in e). In some embodiments of the DST assay, the binding agent is a first binding agent, and the disclosed methods further comprise contacting the mixture of beads with a second binding agent comprising an antibody-binding portion, and (i) a second coding tag comprising identifying information regarding the antibody-binding portion, or (ii) a detectable label; and the method comprises transferring the identifying information in the second coding tag to the extended recording tag to generate a further extended recording tag, or detecting the detectable label. In some of these embodiments, the further extended recording tag(s) is/are analyzed in e). Analysis steps may comprise amplification of extended recording tags or complements thereof followed by NGS. The described second cycle with the second binding agent that binds the immobilized antibodies can be used to identify antibody isotype or subclass. For example, by choosing a specific second binding agent that binds specifically to a particular antibody isotype, such as IgA, IgD, IgE, IgG or IgM, the information about antibody isotype can be encoded to the extended recording tags and analyzed subsequently. In additions, a specific second binding agent can distinguish immobilized antibody subclasses, such as IgG1, IgG2, IgG3 and IgG4 for IgG isotype, and encode this information to the extended recording tags, since these antibody subclasses contain a different heavy chain.

In some embodiments of the DST assay, biological samples are processed before contacting the samples with a plurality of beads in a). Examples of sample processing include removing solid materials and proteins other than the antibodies by performing centrifugation or filtration. In some embodiments, antibodies from biological samples that bind to assay components can be removed before the DST assay by contacting with the assay beads that do not comprise binding element configured to bind antibodies (unspecifically bound antibodies can be depleted before the assay).

In some embodiments of the DST assay, a complex containing antibodies bound to the recording tag and to the binding element is obtained before immobilizing the antibodies to a solid support. In some embodiments, the binding element comprises the recording tag comprising a sample-specific barcode, so the binding element bind to the antibodies, thus forming the complex. An example of such binding element is a conjugate comprising a nucleic acid recording tag and an immunoglobulin-binding protein, such as Protein G. Methods of making such conjugates are known and disclosed elsewhere in this application; similar methods are used to prepare antigen-coding tag conjugates. In other embodiments, the binding element and the recording tag are reacted separately; for example, the binding element bind to the antibodies first, and then the recording tag is contacted with the binding element-antibody subcomplex, thus forming the complex. The recording tag may be attached to the binding element-antibody subcomplex via nucleic acid hybridization (for example, when the binding element comprises a short complementary nucleic acid probe), or using a chemical reaction, such as a click-chemistry reaction, between the recording tag and a moiety on the binding element.

In some embodiments of the DST assay, a complex containing antibodies bound to a sample-specific barcode and to the binding element is obtained before immobilizing the antibodies to a solid support comprising a recording tag. In these embodiments, the sample-specific barcode and the recording tag are at the beginning two separate molecules. The sample-specific barcode can be attached to the binding element before or after binding to the antibodies. Before the information transfer step (d), information of the sample-specific barcode should be transferred to the recording tag. Thus, after encoding of the antigen binding history by transferring of information from the antigen coding tag to one or more recording tags, the extended recording tags will contain information regarding sample identity.

In some embodiments, antibodies from the biological samples are contacted with a modifying agent to which a recording tag or a sample-specific barcode is attached. In some embodiments, the modifying agent reacts with amino acid residues of a particular type. In some embodiments, before contacting the antibodies with the binding element configured to bind antibodies, the antibodies or the binding element are contacted with a nucleic acid molecule comprising a reactive handle, wherein the reactive handle is configured to be attached to one or more amino acid residues of a particular type in the antibodies or the binding element. Chemical coupling between the nucleic acid molecule and amino acid residues is achieved through amino-acid-specific chemical modification methods known in the art; for example, lysine residues can be modified with NHS-ester chemistry and cysteine residues selectively interact with the maleimide group. Examples of amino-acid-specific chemical modification methods are disclosed in, for example, U.S. Pat. No. 10,697,974 B2 and in Zanon PRA, et al. "Profiling the Proteome-Wide Selectivity of Diverse Electrophiles". ChemRxiv; 2021. DOI: 10.26434/chemrxiv.14186561.v1.

In some embodiments, after transfer of information from the coding tag to one or more recording tags (thereby generating one or more extended recording tags), the one or more extended recording tags or a copy thereof are released and collected, optionally amplified, and then sequenced. In some embodiments, copies of the extended recording tags are released into solution by in situ synthesis of complementary strands of the extended recording tags. In some embodiments, the extended recording tags or copies thereof are released by heat-mediated dehybridization. In some embodiments, the released extended recording tags or copies thereof are amplified by PCR. In some embodiments, amplified extended recording tags or copies thereof are characterized by gel electrophoresis, which allows for the confirmation of the formation of extended recording tags with expected lengths, as well as quantitative characterizations of extended recording tag length distribution. In some embodiments, amplified extended recording tags or copies thereof are processed for next-generation sequencing (NGS) and linked to adapter strands to be compatible with common NGS platforms such as Illumina MiSeq. Then the amplified extended recording tags or copies thereof are sequenced at the single-molecule level by NGS. Sequencing reads are then analyzed to allow identification of unique barcode sequences and relationships to corresponding antigens.

In some embodiments of the DST assay, during analysis of one or more extended recording tags (step e)), the one or more extended recording tags, or copies thereof, or complements thereof, are released from the solid support. In some embodiments, the release is achieved by a polymerization reaction using a primer specific for one or more of the extended recording tags, generating a copy of the extended recording tag, which can be further processed and analyzed by sequencing. In other embodiments, the release is achieved by addition of a specific restriction enzyme that recognizes and cleaves a double stranded portion of one or more of the extended recording tags, thereby releasing a part of the one or more of the extended recording tags, which can be further processed and analyzed by sequencing. In other embodiments, a different approach for releasing the extended recording tags from the solid support can be employed.

In some embodiments, Unique Molecular Identifiers (UMIs) can be used in both sample and peptide barcodes to enable accurate and precise digital quantitation of the binding events.

In some embodiments, various DNA enrichment and normalization methods can attenuate highly-abundant signals enabling quantitation over several orders of dynamic range.

In some embodiments, use of peptide-specific barcodes combined with the massive multiplexing provided by the NGS analysis enables mapping of conserved antibody epitopes at a population level.

In some embodiments, the DST method further comprises the following steps after the transferring step d) and before the analyzing step e): (d1) contacting the solid support with a second binding agent comprising a binding portion capable of binding to the immobilized antibodies, and either (i) a second coding tag with identifying information regarding the second binding agent, or (ii) a first detectable label; and (e1) either (iii) transferring the information of the second coding tag to the one or more extended recording tags to generate one or more further extended recording tags, or (iv) detecting the first detectable label; wherein the one or more further extended recording tags or copy thereof are released from the mixture of beads and sequenced in e). These additional steps can provide further information regarding the immobilized antibodies, such as determine types of the antibodies by using type-specific second binding agents. For example, these additional steps can be used to determine whether antigen-specific antibodies detected in the biological sample are IgM antibodies or IgG antibodies. In this embodiment, second binding agents are used that specifically recognize Fc portions of IgM and IgG antibodies and are able to differentiate between them.

In some embodiments, the animal pathogen is a human pathogen, and the claimed method allows to perform population-wide serotyping of human population.

In some embodiments, the animal pathogen is a bird or a mammalian pathogen. In such embodiment, animal population can be screened to identify previous exposure to zoonotic infections, for example, to pathogens that originate in a bird or a mammal, but can be evolved and transmitted to humans.

The disclosed variants of the DST assay are well-suited to detect previous exposure to one or more pathogens in multiple subjects. In some embodiments, a single antigen specific for particular pathogen and conjugated with a coding tag can be used in the DST assay.

In other embodiments, more than one antigen specific for particular pathogen can be employed in the DST assay.

Relevant antigens can be identified from existing research publications, or using a predictive tools, such as an immune epitope database and analysis resource (e.g., iedb.org).

One can identify a practical number of antigens for a particular pathogen to be used in the DST assay to faithfully detect the previous exposure.

In some embodiments, in order to detect a previous exposure to the pathogen(s) of the subject (such as human individual) by the DST assays disclosed herein, it is necessary to choose (or design) one or more antigens suitable for the assays. In preferred embodiments, antigen(s) is/are chosen that is/are involved in functions important to or essential to virulence of the pathogen(s) of interest.

In some embodiments, an optimum (finite) number of specific antigens is chosen to faithfully detect subject's exposure to particular pathogen in one of the DST assays. The ability to accurately detect exposure to particular pathogen depends on the subject's: a) antibody titer (amount); b) antigen sequence; c) antibody potency; and d) antibody recognition sequence. Some of these parameters are unique to each subject; thus, a large number of subjects needs to be screened to establish determine the false-discovery rate based on these parameters, and depending on the application, one can set a threshold value for the false-discovery rate differently.

Strictly speaking or in some cases, the theoretical number of antigens required for a given pathogen is undeterminable a priori. In some embodiments, the number of antigens may be N−1, where N is the number of amino acid residues in the pathogen's protein(s) of interest, and each antigen represents a sliding window differing by one amino acid residue. This is the most conservative approach appropriate for an entirely new pathogen. If antigenic sections are long, having a very large overlap in the similar amino acid residues between antigens is unnecessary. A potential strategy would be to computationally fragment the pathogen's protein of interest into 2M pieces, where M is the number of fragments of X length in the pathogen's protein(s) of interest. The factor of 2 is used for the seams where fragments meet, creating an overlapped pattern.

Either aforementioned extensive overlapping strategy may be appropriate for initial investigation with a limited cohort. Once a large number of antigens are used to train a model in recognizing a novel pathogen, it may become straightforward to apply feature selection methods to remove uninformative antigens, while maintaining the desired level of accuracy on the receiver operating characteristic (ROC) curve.

An alternative (or additional) strategy for limiting the number of initial antigens required to train a pathogen detection model can be designed using bioinformatics and modeling similarities to other known pathogens, and what proteins and/or regions are typically recognized by antibodies. Similarly, regions with high sequence similarity to other pathogens, and therefore providing little to no resolving power can be bioinformatically removed. In some embodiments, when combined, several low-information antigens may however become informative.

Machine learning can be used to establish a model capable of predicting the previous exposure status of a subject. In some embodiments, this model would be trained with a number of known true-negative subject samples (e.g., for SARS-CoV-2, samples taken before the COVID-19 pandemic). A number of known true-positive patient samples may be used to train a classifier to predict whether the subject is positive or negative, and the error rate of said model can be determined both via cross-validation and via testing using held-out or newly acquired data. As there may be several valid phenotypes for a "positive" sample, the model may be trained to recognize variations from a standard background trained using only negative samples. In this case, the model is looking for variations (outliers) from the true-negative background. It is also possible to cluster the positive subjects by phenotypic signature. This may be useful when determining what variants of a pathogen the subject was exposed to, or how potent the antibodies may be at combating infection with a particular strain. If positive and negative samples are not available, an unsupervised clustering approach or outlier detection (if the infection rate is low) may be used.

In some embodiments of the DST assay, 1, 2, 3, 4 or 5 different antigens each attached to a corresponding coding tag comprising identifying information regarding the antigen is or are used as a mixture during the assay. In some embodiments of the DST assay, a threshold value for detection of the previous exposure of a subject to a pathogen is set before conducting the assay. In some embodiments, the threshold value for detection can be set as 80%, 90%, 95% or 99%, representing sensitivity of the assay.

Various aspects of the invention are further discussed below.

Immobilization of Antibodies from Biological Samples on a Solid Support

In some embodiments, the target antibody is joined to a support before performing the binding reaction. In some cases, it is desirable to use a support with a large carrying capacity to immobilize a large number of target antibodies. In some embodiments, it is preferred to immobilize the targets using a three-dimensional support (e.g., a porous matrix or a bead). In some embodiments, a plurality of targets are attached to a support prior to the binding reaction and contacting with an antigen.

Various reactions may be used to attach the recording tag and/or the antibody molecule to a solid support (e.g., beads). In preferred embodiments, bioorthogonal reactions are utilized that offer fast kinetics and permissible reaction conditions. Similar reactions may be used to attach antigen(s) to corresponding coding tag(s) comprising identifying information regarding the antigen. The recording tag and/or the antibody molecule may be attached directly or indirectly to the support. In some cases, the antibody molecule is attached to the support via a capture polynucleotide comprising the recording tag. Exemplary reactions include click chemistry reactions, such as the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothioscyanate, an aldehyde, an epoxide, or the like. In some embodiments, iEDDA click chemistry is used for immobilizing polypeptides to a support since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction. In one case, a polypeptide is labeled with a bifunctional click chemistry reagent, such as alkyne-NHS ester (acetylene-PEG-NHS ester) reagent or alkyne-benzophenone to generate an alkyne-labeled polypeptide. In some embodiments, an alkyne can also be a strained alkyne, such as cyclooctynes including Dibenzocyclooctyl (DBCO).

In certain embodiments where multiple targets are attached to the same support, the target molecules can be spaced appropriately to accommodate methods of performing the binding reaction and any downstream analysis steps to be used to assess the target. In some embodiments, spacing of the targets on the support is determined based on the consideration that information transfer from a coding tag of an antigen bound to one target molecule may reach a neighboring molecule.

In some embodiments, the surface of the support is passivated (blocked). A "passivated" surface refers to a surface that has been treated with outer layer of material. Methods of passivating surfaces include standard methods from the fluorescent single molecule analysis literature, including passivating surfaces with polymer like polyethylene glycol (PEG) (Pan et al., 2015, Phys. Biol. 12:045006), polysiloxane (e.g., Pluronic F-127), star polymers (e.g., star PEG) (Groll et al., 2010, Methods Enzymol. 472:1-18), hydrophobic dichlorodimethylsilane (DDS)+self-assembled Tween-20 (Hua et al., 2014, Nat. Methods 11:1233-1236), diamond-like carbon (DLC), DLC+PEG (Stavis et al., 2011, Proc. Natl. Acad. Sci. USA 108:983-988), and zwitterionic moiety (e.g., U.S. Patent Application Publication US 2006/0183863). In addition to covalent surface modifications, a number of passivating agents can be employed as well including surfactants like Tween-20, polysiloxane in solution (Pluronic series), poly vinyl alcohol (PVA), and proteins like BSA and casein. Alternatively, density of macromolecules (e.g., peptides or antibodies) can be titrated on the surface or within the volume of a solid substrate by spiking a competitor or "dummy" reactive molecule when immobilizing peptides or antibodies to the solid substrate.

To control spacing of the immobilized targets on the support, the density of functional coupling groups for attaching the target (e.g., TCO or carboxyl groups (COOH)) may be titrated on the substrate surface. In some embodiments, multiple target molecules (e.g., macromolecules) are spaced apart on the surface or within the volume (e.g., porous supports) of a support such that adjacent molecules are spaced apart at a distance of about 50 nm to about 500 nm, or about 50 nm to about 200 nm, or about 50 nm to about 100 nm. In some embodiments, multiple molecules are spaced apart on the surface of a support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, multiple antibody molecules are spaced apart on the surface of a support with an average distance of at least 50 nm. In some embodiments, molecules are spaced apart on the surface or within the volume of a support such that, empirically, the relative frequency of inter- to intramolecular events (e.g. transfer of information) is <1:10; <1:100; <1:1,000; or <1:10,000. In some embodiments, the plurality of target molecules (e.g., antibodies) is coupled on the support spaced apart at an average distance between two adjacent molecules which ranges from about 50 to 100 nm, or from about 50 to 500 nm.

In some embodiments, appropriate spacing of the target molecules (e.g., antibodies) on the support is accomplished by titrating the ratio of available attachment molecules on the substrate surface. In some examples, the substrate surface (e.g., bead surface) is functionalized with a carboxyl group (COOH) which is treated with an activating agent (e.g., activating agent is EDC and Sulfo-NHS). In some examples, the substrate surface (e.g., bead surface) comprises NHS moieties. In some embodiments, a mixture of mPEGn-$NH_2$ and $NH_2$-PEG$_n$-mTet is added to the activated beads (wherein n is any number, such as 1-100). The ratio between the mPEG$_3$-$NH_2$ (not available for coupling) and $NH_2$-PEG$_{24}$-mTet (available for coupling) is titrated to generate an appropriate density of functional moieties available to attach the antibodies on the substrate surface. In certain embodiments, the mean spacing between coupling moieties (e.g., $NH_2$-PEG$_4$-mTet) on the solid surface is at least 50 nm, at least 100 nm, at least 250 nm, or at least 500 nm. In some specific embodiments, the ratio of $NH_2$-PEG$_n$-mTet to mPEG$_3$-$NH_2$ is about or greater than 1:1000, about or greater than 1:10,000, about or greater than 1:100,000, or about or greater than 1:1,000,000. In some further embodiments, the recording tag attaches to the $NH_2$-PEG$_n$-mTet.

In certain embodiments, an antibody macromolecule can be immobilized to a support by an affinity capture reagent (and optionally covalently crosslinked), wherein the recording tag is associated with the affinity capture reagent directly, or alternatively, the antibody can be directly immobilized to the support with a recording tag. In one embodiment, the antibody macromolecule is attached to a bait nucleic acid which hybridizes to a capture nucleic acid and is ligated to a capture nucleic acid which comprises a reactive coupling moiety for attaching to the support. In some embodiments, the bait or capture nucleic acid may serve as a recording tag to which information regarding the polypeptide can be transferred. In some embodiments, the antibody macromolecule is attached to a bait nucleic acid to form a nucleic acid-antibody conjugate. In some embodiments, the immobilization methods comprise bringing the nucleic acid-antibody conjugate into proximity with a support by hybridizing the bait nucleic acid to a capture nucleic acid attached to the support, and covalently coupling the nucleic acid-macromolecule chimera to the solid support.

Antigen

An antigen can be any molecule (e.g., can comprise peptide, nucleic acid, carbohydrate, small molecule, and a combination thereof) capable of binding to an antibody. An antigen can be a naturally occurring, synthetically produced, or recombinantly expressed molecule. In some embodiments, the scaffold used to engineer an antigen can be from any species, e.g., human, non-human, transgenic.

In some embodiments, the antigen has a high affinity and high selectivity for the antibody. In particular, a high binding affinity with a low off-rate may be efficacious for information transfer between the coding tag and recording tag. In certain embodiments, an antigen has a Kd of about <500 nM, <200 nM, <100 nM, <50 nM, <10 nM, <5 nM, <1 nM, <0.5 nM, or <0.1 nM. In a particular embodiment, the antigen is added to the antibody at a concentration >1×, >5×, >10×, 100×, or >1000× its Kd to drive binding to completion. In a particular embodiment, the provided methods for performing a binding reaction is compatible with an antibody with medium to low affinity for the antigen.

In certain embodiments, the antigen further comprises one or more detectable labels such as fluorescent labels, in addition to the coding tag. In one embodiment, the detectable label is optically detectable. In some embodiments, the detectable label comprises a fluorescently moiety, a color-coded nanoparticle, a quantum dot or any combination thereof. In one embodiment the label comprises a polystyrene dye encompassing a core dye molecule such as a FluoSphere™, Nile Red, fluorescein, rhodamine, derivatized rhodamine dyes, such as TAMRA, phosphor, polymethadine dye, fluorescent phosphoramidite, TEXAS RED, green fluorescent protein, acridine, cyanine, cyanine 5 dye, cyanine 3 dye, 542'-aminoethyl)-aminonaphthalene-1-sulfonic acid (EDANS), BODIPY, 120 ALEXA or a derivative or modification of any of the foregoing. In one embodiment, the detectable label is resistant to photobleaching while producing lots of signal (such as photons) at a unique and easily detectable wavelength, with high signal-to-noise ratio.

In certain embodiments, an antibody is also contacted with a non-cognate antigen. As used herein, a non-cognate antigen is referring to an antigen that is selective for a different antibody than the particular antibody being considered. For example, a set of antibodies A, B and C specific for antigen A, antigen B and antigen C, respectively, is immobilized and contacted with antigen B. Antigen B is a non-cognate antigen for antibody A, but at the same time, antigen B is a cognate antigen for antibody B. Thus, if multiple antibodies are analyzed in a multiplexed reaction, an antigen for one antibody may be a non-cognate antigen for another, and vice versa.

In certain embodiments, the concentration of the antigens in a solution is controlled to reduce background and/or false positive results of the assay. In some embodiments, the concentration of an antigen can be at any suitable concentration, e.g., at about 0.0001 nM, about 0.001 nM, about 0.01 nM, about 0.1 nM, about 1 nM, about 5 nM, about 10 nM, about 50 nM, about 100 nM, about 500 nM, or about 1,000 nM. In some embodiments, the ratio between the soluble antigen molecules and the immobilized antibodies can be at any suitable range, e.g., at about 0.00001:1, about 0.0001:1, about 0.001:1, about 0.01:1, about 0.1:1, about 1:1, about 2:1, about 5:1, about 10:1, about 50:1, about 100:1, about $10^4$:1, about $10^5$:1, about $10^6$:1, or higher, or any ratio in between the above listed ratios. Higher ratios between the soluble antigen molecules and the immobilized antibodies can be used to drive the binding and/or the coding tag information transfer to completion.

Transfer of Information Between Recording Tags and Coding Tags

In some embodiments, the target macromolecule (e.g., antibody) may be associated with a nucleic acid molecule or a oligonucleotide (e.g., recording tag). In some aspects, a plurality of target antibodies in the sample is provided with recording tags. The recording tags may be associated or attached, directly or indirectly to the target macromolecules using any suitable means. In some embodiments, a macromolecule may be associated with one or more recording tags. In some aspects, the recording tag may be any suitable sequenceable moiety to which identifying information can be transferred (e.g., information from one or more coding tags). In some embodiments, at least one recording tag is associated or co-localized directly or indirectly with the target macromolecule (e.g., antibody). In another embodiment, multiple recording tags are attached to the antibody, such as to the lysine residues or peptide backbone. A recording tag may be single stranded, or partially or completely double stranded. A recording tag may have a blunt end or overhanging end. In other embodiments, a subset of antibodies within a sample are labeled with recording tags. In some embodiments, the recording tag may comprise a unique molecular identifier, a compartment tag, sample-specific barcode, a spacer sequence, a universal priming site, or any combination thereof. In some embodiments, the recording tag may comprise a blocking group, such as at the 3'-terminus of the recording tag. In some cases, the 3'-terminus of the recording tag is blocked to prevent extension of the recording tag by a polymerase.

In some embodiments, the recording tag can include a sample-identifying barcode. A sample-specific barcode is useful in the multiplexed analysis of a set of samples in a single reaction vessel or immobilized to a single solid substrate or collection of solid substrates. For example, antibodies from many different samples can be associated with recording tags with sample-specific barcodes, and then all the samples pooled together prior to immobilization to a support, and prior to performing the DST assay. Alternatively, antibodies from each sample can be first attached to a separate sold support (such as a bead) comprising a recording tag with sample-identifying (sample-specific) barcode, and then beads with immobilized antibodies obtained from multiple different samples can be pooled together and processed in the DST assay (e.g., the mixture of beads is contacted with an antigen attached to a coding tag followed by encoding of the identifying information to the corresponding recording tag).

In certain embodiments, a recording tag comprises an optional unique molecular identifier (UMI), which provides a unique identifier tag for each macromolecules (e.g., antibody) to which the UMI is associated with. A UMI can be about 3 to about 40 bases, about 3 to about 20 bases, or about 3 to about 10 bases, or about 3 to about 8 bases in length. A UMI can be used to de-convolute data from a plurality of extended recording tags to identify sequence reads related to individual antibodies. In other embodiments, multiple copies of a recording tag are associated with a single antibody, with each copy of the recording tag comprising the same UMI.

In certain embodiments, a recording tag comprises a universal priming site, e.g., a forward or 5' universal priming site. A universal priming site is a nucleic acid sequence that may be used for priming a library amplification reaction and/or for sequencing. A universal priming site may include, but is not limited to, a priming site for PCR amplification, flow cell adaptor sequences that anneal to complementary oligonucleotides on flow cell surfaces (e.g., Illumina next generation sequencing), a sequencing priming site, or a combination thereof. A universal priming site can be about 10 bases to about 60 bases. In some embodiments, a universal priming site comprises an Illumina P5 primer (5'-AATGATACGGCGACCACCGA-3'-SEQ ID NO:2) or an Illumina P7 primer (5'-CAAGCAGAAGACGGCAT-ACGAGAT-3'-SEQ ID NO:3).

The extended recording tag is any nucleic acid molecule or sequenceable polymer molecule (see, e.g., Niu et al., 2013, Nat. Chem. 5:282-292; Roy et al., 2015, Nat. Commun. 6:7237) that comprises identifying information for a macromolecule, e.g., an antibody. An extended recording tag associated with the antibody comprising identifying information from the coding tag may comprise information from an antigen's coding tag representing each binding cycle performed. In certain embodiments, an extended recording tag associated with the immobilized antibody may comprise information from multiple coding tags representing multiple, successive binding events.

Coding tag information associated with a specific antigen may be transferred to a recording tag using a variety of methods. In certain embodiments, information of a coding tag is transferred to a recording tag via primer extension (Chan et al. (2015) Curr Opin Chem Biol 26: 55-61). A spacer sequence on the 3'-terminus of a recording tag or an extended recording tag anneals with complementary spacer sequence on the 3' terminus of a coding tag and a polymerase (e.g., strand-displacing polymerase) extends the recording tag sequence, using the annealed coding tag as a template. In some embodiments, oligonucleotides complementary to coding tag encoder sequence and 5' spacer can be pre-annealed to the coding tags to prevent hybridization of the coding tag to internal encoder and spacer sequences present in an extended recording tag. The 3' terminal spacer, on the coding tag, remaining single stranded, preferably binds to the terminal 3' spacer on the recording tag. In other embodiments, a nascent recording tag can be coated with a single stranded binding protein to prevent annealing of the coding tag to internal sites.

In some embodiments, a DNA polymerase that is used for primer extension possesses strand-displacement activity and has limited or is devoid of 3'-5 exonuclease activity. Several of many examples of such polymerases include Klenow exo-(Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, 9° N Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs).

Mis-priming or self-priming events, such as when the terminal spacer sequence of the recording tag primes extension self-extension may be minimized by inclusion of single stranded binding proteins (T4 gene 32, *E. coli* SSB, etc.), DMSO (1-10%), formamide (1-10%), BSA(10-100 ug/ml), TMACl (1-5 mM), ammonium sulfate (10-50 mM), betaine (1-3 M), glycerol (5-40%), or ethylene glycol (5-40%), in the primer extension reaction. In some embodiments, polymerase extension buffers are comprised of 40-120 mM buffering agent such as Tris-Acetate, Tris-HCl or HEPES at a pH of 6-9.

In some embodiments, to minimize non-specific interaction of the coding tag labeled antigens in solution with the recording tags of immobilized antibodies, competitor (also referred to as blocking) oligonucleotides complementary to nucleic acids containing spacer sequences (e.g., on the recording tag) can be added to binding reactions to minimize non-specific interactions. In some embodiments, the blocking oligonucleotides contain a sequence that is complementary to the coding tag or a portion thereof attached to the antigen. In some embodiments, blocking oligonucleotides are relatively short. Excess competitor oligonucleotides are washed from the binding reaction prior to primer extension, which effectively dissociates the annealed competitor oligonucleotides from the nucleic acids on the recording tag, especially when exposed to slightly elevated temperatures (e.g., 30-50° C.). Blocking oligonucleotides may comprise a terminator nucleotide at its 3' end to prevent primer extension.

In some embodiments, the transfer of identifying information (e.g., from a coding tag to a recording tag) can be accomplished by ligation (e.g., an enzymatic or chemical ligation, a splint ligation, a sticky end ligation, a single-strand (ss) ligation such as a ssDNA ligation, or any combination thereof), a polymerase-mediated reaction (e.g., primer extension of single-stranded nucleic acid or double-stranded nucleic acid), or any combination thereof.

Examples of ligases include, but are not limited to CV DNA ligase, T4 DNA ligase, T7 DNA ligase, T3 DNA ligase, Taq DNA ligase, *E. coli* DNA ligase, 9° N DNA ligase, Electroligase® (See e.g., U.S. Patent Publication No. US20140378315). Alternatively, a ligation may be a chemical ligation reaction, such as chemical ligation using standard chemical ligation or "click chemistry" (Gunderson et al., Genome Res (1998) 8(11): 1142-1153; El-Sagheer et al., Proc Natl Acad Sci USA (2011) 108(28): 11338-11343; Sharma et al., Anal Chem (2012) 84(14): 6104-6109; Roloff et al., Methods Mol Biol (2014) 1050:131-141).

In another embodiment, transfer of PNAs can be accomplished with chemical ligation using published techniques. The structure of PNA is such that it has a 5' N-terminal amine group and an unreactive 3' C-terminal amide. Chemical ligation of PNA requires that the termini be modified to be chemically active. This is typically done by derivatizing the 5' N-terminus with a cysteinyl moiety and the 3' C-terminus with a thioester moiety. Such modified PNAs easily couple using standard native chemical ligation conditions (Roloff et al., (2013) Bioorgan. Med. Chem. 21:3458-3464).

In some embodiments, coding tag information can be transferred using topoisomerase. Topoisomerase can be used to ligate a topo-charged 3' phosphate on the recording tag (or extensions thereof or any nucleic acids attached) to the 5' end of the coding tag, or complement thereof (Shuman et al., 1994, J. Biol. Chem. 269:32678-32684).

In some examples, the final extended recording tag containing information from an antigen and, optionally, a second binding agent that was bound to the immobilized antibody, is optionally flanked by universal priming sites to facilitate downstream amplification and/or DNA sequencing. The forward universal priming site (e.g., Illumina's P5-S1 sequence) can be part of the original design of the recording tag and the reverse universal priming site (e.g., Illumina's P7-S2' sequence) can be added as a final step in the extension of the recording tag.

In some embodiments, the labeling of the antibody with a recording tag is performed using standard amine coupling chemistries. In a particular embodiment, the recording tag can comprise a reactive moiety (e.g., for conjugation to a solid surface, a multifunctional linker, or a macromolecule), a linker, a universal priming sequence, a barcode, an optional UMI, and a spacer (Sp) sequence for facilitating information transfer to/from a coding tag. In some embodiments, the recording tags may comprise a reactive moiety for a cognate reactive moiety present on the target antibody (e.g., click chemistry labeling, photoaffinity labeling). For example, recording tags may comprise an azide moiety for interacting with alkyne-derivatized antibodies.

The coding tag associated with the antigen is or comprises a polynucleotide with any suitable length, e.g., a nucleic acid molecule of about 3 bases to about 100 bases, that comprises identifying information for its associated antigen. A coding tag may be composed of DNA, RNA, polynucleotide analogs, or a combination thereof. Polynucleotide analogs include PNA, gPNA, BNA, GNA, TNA, LNA, morpholino polynucleotides, 2'-0-Methyl polynucleotides, alkyl ribosyl substituted polynucleotides, phosphorothioate polynucleotides, and 7-deaza purine analogs. A coding tag may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767). A coding tag may comprise a barcode sequence or a sequence with identifying information, which is optionally flanked by one spacer on one side or optionally flanked by a spacer on each side. A coding tag may also be comprised of an optional UMI and/or an optional binding cycle-specific barcode. A coding tag may refer to the coding tag that is directly attached to an antigen, or to a complementary sequence hybridized to the coding tag directly attached to an antigen (e.g., for double stranded coding tags). A coding tag may be a single stranded molecule, a double stranded molecule, or a partially double stranded. A coding tag may comprise blunt ends, overhanging ends, or one of each. In some embodiments, the coding tag may comprise a hairpin. In certain embodiments, the hairpin comprises mutually complementary nucleic acid regions are connected through a nucleic acid strand. In some embodiments, the nucleic acid hairpin can also further comprise 3' and/or 5' single-stranded region(s) extending from the double-stranded stem segment. In some examples, the hairpin comprises a single strand of nucleic acid.

A coding tag may include a terminator nucleotide incorporated at the 3' end of the 3' spacer sequence. After an antigen binds to an antibody and their corresponding coding tag and recording tags anneal via complementary spacer sequences, it is possible for primer extension to transfer information from the coding tag to the recording tag, or to transfer information from the recording tag to the coding tag. Addition of a terminator nucleotide on the 3' end of the coding tag prevents transfer of recording tag information to the coding tag. It is understood that for embodiments described herein involving generation of extended coding tags, it may be preferable to include a terminator nucleotide at the 3' end of the recording tag to prevent transfer of coding tag information to the recording tag.

In some embodiments, the coding tag sequence can be optimized for the particular sequencing analysis platform. In a particular embodiment, the sequencing platform is nanopore sequencing. In some embodiments, the sequencing platform has a per base error rate of >1%, >5%, >10%, >15%, >20%, >25%, or >30%. For example, if the extended nucleic acid is to be analyzed using a nanopore sequencing instrument, the barcode sequences (e.g., sequences comprising identifying information from the coding tag) can be designed to be optimally electrically distinguishable in transit through a nanopore.

A coding tag can be joined to an antigen directly or indirectly, by any means known in the art, including covalent and non-covalent interactions. In some embodiments, a coding tag may be joined to antigen enzymatically or chemically. In some embodiments, a coding tag may be joined to an antigen via ligation. In some cases, a coding tag may be joined to an antigen to an unnatural amino acid, such as via a covalent interaction with an unnatural amino acid. In some embodiments, an antigen is joined to a coding tag via SpyCatcher-SpyTag interaction. The SpyTag peptide forms an irreversible covalent bond to the SpyCatcher protein via a spontaneous isopeptide linkage, thereby offering a genetically encoded way to create peptide interactions that resist force and harsh conditions (Zakeri et al., 2012, Proc. Natl. Acad. Sci. 109:E690-697; Li et al., 2014, J. Mol. Biol. 426:309-317). A antigen may be expressed as a fusion protein comprising the SpyCatcher protein.

In some embodiments, immobilized antibody molecule is attached to a bead or to a recording tag by one of the methods disclosed in the following U.S. patents: U.S. Pat. Nos. 9,547,003, 10,247,727, 10,527,609, 10,526,379, US 2016272543. Similar approaches can be utilized to attach the coding tag to an antigen.

In other embodiments, an immobilized antibody molecule is attached to a bead, or an antigen is joined to a coding tag, via SnoopTag-SnoopCatcher peptide-protein interaction. The SnoopTag peptide forms an isopeptide bond with the SnoopCatcher protein (Veggiani et al., Proc. Natl. Acad. Sci. USA, 2016, 113:1202-1207). A antigen may be expressed as a fusion protein comprising the SnoopCatcher protein. In yet other embodiments, an immobilized antibody molecule is attached to a bead, or an antigen is joined to a coding tag, via the HaloTag® protein fusion tag and its chemical ligand. HaloTag is a modified haloalkane dehalogenase designed to covalently bind to synthetic ligands (HaloTag ligands) (Los et al., 2008, ACS Chem. Biol. 3:373-382). The synthetic ligands comprise a chloroalkane linker attached to a variety of useful molecules. A covalent bond forms between the HaloTag and the chloroalkane linker that is highly specific, occurs rapidly under physiological conditions, and is essentially irreversible.

In some embodiments, an antigen is joined to a coding tag using a cysteine bioconjugation method. In some embodiments, an antigen is joined to a coding tag using π-clamp-mediated cysteine bioconjugation (See e.g., Zhang et al., Nat Chem. (2016) 8(2):120-128). In some cases, an antigen is joined to a coding tag using 3-arylpropiolonitriles (APN)-mediated tagging (e.g. Koniev et al., Bioconjug Chem. 2014; 25(2):202-206).

In some embodiments, the extended recording tag generated from performing the provided methods comprises information transferred from one or more coding tags. In some embodiments, the extended recording tags further comprise identifying information from one or more coding tags. In some embodiments, the extended recording tags are amplified (or a portion thereof) prior to determining at least the sequence of the coding tag(s) in the extended recording tag. In some embodiments, the extended recording tags (or a portion thereof) are released prior to determining at least the sequence of the coding tag(s) in the extended recording tag.

The length of the final extended recording tag generated by the methods described herein is dependent upon multiple factors, including the length of the coding tag(s) (e.g., barcode and spacer), and optionally including any unique molecular identifier, spacer, universal priming site, barcode, or combinations thereof. After transfer of the final tag information to the extended recording tag (e.g., from any coding tags), the recording tag can be capped by addition of a universal reverse priming site via ligation, primer extension or other methods known in the art. In some embodiments, the universal forward priming site in the nucleic acid (e.g., on the recording tag) is compatible with the universal reverse priming site that is appended to the final extended nucleic acid. In some embodiments, a universal reverse priming site is an Illumina P7 primer (5'-CAAGCAGAAGACGGCATACGAGAT-3'-SEQ ID NO:3) or an Illumina P5 primer (5'-AATGATACGGCGACCACCGA-3'-SEQ ID NO:2). The sense or antisense P7 may be appended, depending on strand sense of the nucleic acid to which the identifying information from the coding tag is transferred to. An extended nucleic acid library can be cleaved or amplified directly from the support (e.g., beads) and used in traditional next generation sequencing assays and protocols.

In some embodiments, a primer extension reaction is performed on a library of single stranded extended recording tags to copy complementary strands thereof.

Extended nucleic acids recording tags can be processed and analysed using a variety of nucleic acid sequencing methods. In some embodiments, extended recording tags containing the information from one or more coding tags and any other nucleic acid components are processed and analysed. In some embodiments, the collection of extended recording tags can be concatenated. In some embodiments, the extended recording tag can be amplified prior to determining the sequence.

Examples of sequencing methods include, but are not limited to, chain termination sequencing (Sanger sequencing); next generation sequencing methods, such as sequencing by synthesis, sequencing by ligation, sequencing by hybridization, polony sequencing, ion semiconductor sequencing, and pyrosequencing; and third generation sequencing methods, such as single molecule real time sequencing, nanopore-based sequencing, duplex interrupted sequencing, and direct imaging of DNA using advanced microscopy. Suitable sequencing methods for use in the invention include, but are not limited to, sequencing by hybridization, sequencing by synthesis technology (e.g., HiSeg™ and Solexa™, Illumina), SMRT™ (Single Molecule Real Time) technology (Pacific Biosciences), true single molecule sequencing (e.g., HeliScope™, Helicos Biosciences), massively parallel next generation sequencing (e.g., SOLiD™, Applied Biosciences; Solexa and HiSeg™, Illumina), massively parallel semiconductor sequencing (e.g., Ion Torrent), pyrosequencing technology (e.g., GS FLX and GS Junior Systems, Roche/454), nanopore sequence (e.g., Oxford Nanopore Technologies).

A library of nucleic acid recording tags may be amplified in a variety of ways. A library of nucleic acids (e.g., recording tags comprising information from one or more coding tags) undergo exponential amplification, e.g., via PCR or emulsion PCR. Emulsion PCR is known to produce more uniform amplification (Hori, Fukano et al., Biochem Biophys Res Commun (2007) 352(2): 323-328). Alternatively, a library of recording tags may undergo linear amplification, e.g., via in vitro transcription of template DNA using T7 RNA polymerase. The library of recording tags can be amplified using primers compatible with the universal forward priming site and universal reverse priming site contained therein. An example of a library amplification in preparation for next generation sequencing is as follows: a 20 µl PCR reaction volume is set up using an extended nucleic acid library eluted from ~1 mg of beads (~10 ng), 200 µM dNTP, 1 µM of each forward and reverse amplification primers, 0.5 µl (1 U) of Phusion Hot Start enzyme (New England Biolabs) and subjected to the following cycling conditions: 98° C. for 30 sec followed by 20 cycles of 98° C. for 10 sec, 60° C. for 30 sec, 72° C. for 30 sec, followed by 72° C. for 7 min, then hold at 4° C.

The methods disclosed herein can be used for analysis, including detection, quantitation and/or sequencing, of a plurality of macromolecules simultaneously (multiplexing). Multiplexing as used herein refers to analysis of a plurality of macromolecules (e.g. antibodies) in the same assay. The plurality of macromolecules can be derived from the same sample or different samples. The plurality of macromolecules can be derived from the same subject or different subjects. A plurality of macromolecules includes 2 or more macromolecules, 10 or more macromolecules, 50 or more macromolecules, 100 or more macromolecules, 1,000 or more macromolecules, 5,000 or more macromolecules, 10,000 or more macromolecules.

The B cell immune-repertoire is highly diverse with up to $10^9$ different possible individual heavy chain/light chain clonotypes. B cells display, at a single cell level, a particular clonotype B cell receptor which, upon binding a "non-self" or foreign antigen, activates terminal differentiation into a plasma cell (PC) that generates soluble clonotypic antibodies released into the blood and lymphatic circulation. Information on B cell diversity and maturation has grown exponentially with the application of NGS sequencing to measuring B cell (BCR-Seq) and T cell receptor (TCR-Seq) repertoire diversity and MS-based analysis of the soluble antibody repertoire (e.g., Ig-Seq) in the blood. On average, human serum has about 10 mg/mL immunoglobulin (IgGs, IgMs) distributed across about 10,000 IgG clonotypes (Lavinder, J, et al., "Next-generation sequencing and protein mass spectrometry for the comprehensive analysis of human cellular and serum antibody repertoires." Curr Opin Chem Biol, (2015) 24: 112-120). This diversity is at least three orders lower than the underlying B cell diversity. The average concentration of any given clonotype antibody in the serum is about 1 µg/ml which translates to concentration of ~5 nM, slightly above the Kd of the average serum antibody (Lavinder, J, et al., Curr Opin Chem Biol, (2015) 24: 112-120). In another publication using LC-MS to identify and quantitate human antibody clonotypes, they measured the concentration of plasma antibodies at levels from 300 pM up to 2.5 mM, with a median level of about 6.25 nM (Bondt, et al. 2021. "Human Plasma IgG1 Repertoires Are Simple, Unique, and Dynamic." Cell Systems, September). This agrees well with the estimate from Lavinder et al.

In raising a humoral response to a particular pathogen, ~100 clonotypes are raised with bias towards a handful of clonotypes (Galson, J. D., et al., "Studying the antibody repertoire after vaccination: practical applications." Trends Immunol, (2014) 35(7): 319-331). As such, serotyping of antibodies raised to a particular pathogen is well suited to digital analysis, since the number of antibody clonotypes interacting with epitopes on the pathogen proteome is quite limited.

Exemplary Embodiments

Among the provided embodiments are:

1. A method for sample analysis, comprising: a) (i) separately contacting a plurality of different antibodies of each sample of a plurality of samples with a binding element configured to bind to the plurality of different antibodies in the sample, thereby obtaining binding element-antibody conjugates; and (ii) attaching either the binding element or the binding element-antibody conjugates to a bead, wherein the binding element is attached to the bead before or after contacting the plurality of different antibodies, wherein the binding element is associated with a recording tag comprising a sample-specific barcode before or after attachment to the bead, thereby obtaining a plurality of beads comprising attached binding element-antibody conjugates each associated with the recording tag from each sample; b) mixing the pluralities of beads comprising attached binding element-antibody conjugates from the plurality of samples, thereby obtaining a mixture of beads; c) contacting the mixture of beads with a binding agent comprising an antigen and a coding tag attached thereto, wherein the coding tag comprises an encoder sequence that comprises identifying information regarding the antigen; d) following binding of the antigen to an antibody attached to a bead of the mixture of beads, allowing transfer of identifying information between the coding tag and the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

2. The method of embodiment 1, wherein in a), beads comprising the attached binding element and the recording tag comprising a sample-specific barcode and associated with the binding element are contacted with the plurality of different antibodies of each sample.

3. A method for sample analysis, comprising: a) separately contacting each sample of a plurality of samples with a plurality of beads, wherein each bead of the plurality of beads contacted with the sample comprises: i) a recording tag comprising a sample-specific barcode, and ii) an associated binding element configured to bind to a plurality of different antibodies in the sample, thereby obtaining a plurality of antibody-bound beads from each sample; b) mixing the pluralities of antibody-bound beads from the plurality of samples, thereby obtaining a mixture of beads; c) contacting the mixture of beads with a binding agent comprising an antigen and a coding tag attached thereto, wherein the coding tag comprises an encoder sequence that comprises identifying information regarding the antigen; d) following binding of the antigen to an antibody attached to a bead of the mixture of beads, allowing transfer of identifying information between the coding tag and the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

4. The method of any one of embodiments 1-3, wherein the plurality of samples comprises at least 9 samples, at least 50 samples, at least 96 samples, at least 500 samples, or at least 1,000 samples.

5. The method of embodiment 4, wherein the plurality of samples comprise samples obtained from one or more subjects.

6. The method of embodiment 4, wherein each sample of the plurality of samples is obtained from a different subject.

7. The method of any one of embodiments 1-6, wherein the antigen comprises a component of an animal pathogen, a component of a toxin, an autoantigen associated with an autoimmune disorder, or a component of a tumor cell.

8. The method of any one of embodiments 1-7, wherein the antigen comprises a polypeptide comprising an amino acid sequence from 7 to 30 amino acid residues.

9. The method of any one of embodiments 1-8, wherein the binding element is configured to bind to an antibody constant region, optionally wherein the binding element comprises an immunoglobulin Fc-binding domain and is not configured to bind to an antibody variable region.

10. The method of any one of embodiments 1-9, further comprising covalently cross-linking the antibodies to the binding element in the plurality of antibody-bound beads in a).

11. The method of any one of embodiments 1-10, wherein in c), the mixture of beads is contacted with a plurality of binding agents each comprising a different antigen, wherein each different antigen is attached to a different coding tag comprising an encoder sequence that comprises identifying information regarding the antigen attached thereto.

12. The method of any one of embodiments 1-11, wherein the antigen comprises a peptide sequence from a SARS-CoV-2 virus, and the method detects an antibody that binds to the peptide sequence.

13. The method of embodiment 11, wherein the plurality of binding agents comprises peptide sequences from a SARS-CoV-2 spike (S) protein, a SARS-CoV-2 Envelope (E) protein, a SARS-CoV-2 Membrane (M) protein, and/or a SARS-CoV-2 Nucleocapsid (N) protein, such as any one of the sequences set forth in SEQ ID NO: 4-SEQ ID NO: 13.

14. The method of embodiment 11, wherein the plurality of binding agents comprises peptide sequences from a SARS-CoV-2 spike (S) protein, such as any one of the sequences set forth in SEQ ID NO: 4-SEQ ID NO: 8.

15. The method of embodiment 11, wherein the plurality of binding agents comprises portions from the same biological molecule.

16. The method of embodiment 11, wherein for each binding agent of the plurality of binding agents, the antigen is attached to the coding tag using mRNA or cDNA display.

17. The method of embodiment 11, wherein the plurality of binding agents comprises at least three different antigens.

18. The method of any one of embodiments 1-17, wherein presence/absence, level, and/or activity the antibody to the antigen in the sample is/are analyzed in e).

19. The method of any one of embodiments 1-18, wherein following binding of the antigen to the antibody, the transfer of identifying information occurs from the coding tag to the recording tag associated with the binding element bound to the antibody, thereby generating the extended recording tag, and wherein the encoder sequence or the complement thereof in the extended recording tag is analyzed in e).

20. The method of embodiment 19, further comprising capping the extended recording tag with a polynucleotide that comprises a universal priming site for sequencing, and the capping comprises hybridizing and/or ligating the polynucleotide to the extended recording tag.

21. The method of embodiment 19, wherein the binding agent is a first binding agent, the method further comprising contacting the mixture of beads with a second binding agent comprising an antibody-binding portion, and (i) a second coding tag comprising identifying information regarding the antibody-binding portion, or (ii) a detectable label; and the method comprises transferring the identifying information in the second coding tag to the extended recording tag to generate a further extended recording tag, or detecting the detectable label.

22. The method of embodiment 20 or embodiment 21, wherein the antibody-binding portion is configured to bind to an antibody variable region, and the mixture of beads is contacted with the second binding agent after contacting with the first binding agent and generating the extended recording tag.

23. The method of embodiment 22, wherein the antibody-binding portion is an antigen or an anti-idiotypic antibody.

24. The method of embodiment 21, wherein the antibody-binding portion is configured to bind to an antibody constant region, and the mixture of beads is contacted with the second binding agent before or after generating the extended recording tag.

25. The method of any one of embodiments 1-24, wherein in c), the binding agent comprises two identical antigens joined together, optionally by a linker, and the encoder sequence in the coding tag of the binding agent comprises identifying information regarding the identical antigen.

26. A method for sample analysis, comprising: a) separately contacting each sample of a plurality of samples with i) a nucleic acid tag comprising a sample-specific barcode, and ii) a binding element configured to bind to a plurality of different antibodies in the sample, thereby obtaining a plurality of nucleic acid-bound antibody-binding agent complexes from each sample; b) mixing the pluralities of nucleic acid-bound antibody-binding agent complexes from the plurality of samples and attaching them on a plurality of beads, wherein the plurality of beads optionally comprises a plurality of nucleic acid recording tags, thereby obtaining a mixture of beads comprising a plurality of attached antibodies each associated with a nucleic acid tag or recording tag; c) contacting the mixture of beads with a binding agent comprising an antigen and a coding tag attached thereto, wherein the coding tag comprises an encoder sequence that comprises identifying information regarding the antigen; d) following binding of the antigen to an antibody attached to a bead of the mixture of beads, allowing transfer of identifying information between the coding tag and the nucleic acid tag or the recording tag of the bead, thereby generating an extended coding tag or an extended recording tag, wherein the transfer occurs through a primer extension reaction and/or ligation; and e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

27. The method of embodiment 26, wherein the binding element comprises the nucleic acid tag comprising the sample-specific barcode.

28. The method of embodiment 26 or embodiment 27, wherein the plurality of samples comprises at least 9 samples, at least 50 samples, at least 96 samples, at least 500 samples, or at least 1,000 samples.

29. The method of embodiment 28, wherein the plurality of samples comprise samples obtained from one or more subjects.

30. The method of embodiment 28 or embodiment 29, wherein each sample of the plurality of samples is obtained from a different subject.

31. The method of any one of embodiments 26-30, wherein the antigen comprises a component of an animal pathogen, a component of a toxin, an autoantigen associated with an autoimmune disorder, or a component of a tumor cell.

32. The method of any one of embodiments 26-31, wherein the antigen comprises a polypeptide comprising an amino acid sequence from 7 to 30 amino acid residues.

33. The method of any one of embodiments 26-32, wherein the binding element is configured to bind to an antibody constant region, optionally wherein the binding element comprises an immunoglobulin Fc-binding domain and is not configured to bind to an antibody variable region.

34. The method of any one of embodiments 26-33, further comprising covalently cross-linking the plurality of attached antibodies to the binding element in the mixture of beads in b).

35. The method of any one of embodiments 26-34, wherein in c), the mixture of beads is contacted with a plurality of binding agents each comprising a different antigen, wherein each different antigen is attached to a different coding tag comprising an encoder sequence that comprises identifying information regarding the antigen attached thereto.

36. The method of any one of embodiments 26-35, wherein the antigen comprises a peptide sequence from a SARS-CoV-2 virus, and the method detects an antibody that binds to the peptide sequence.

37. The method of embodiment 35, wherein the plurality of binding agents comprises peptide sequences from a SARS-CoV-2 spike (S) protein, a SARS-CoV-2 Envelope (E) protein, a SARS-CoV-2 Membrane (M) protein, and/or a SARS-CoV-2 Nucleocapsid (N) protein, such as any one of the sequences set forth in SEQ ID NO: 4-SEQ ID NO: 13.

38. The method of embodiment 35, wherein the plurality of binding agents comprises peptide sequences from a SARS-CoV-2 spike (S) protein, such as any one of the sequences set forth in SEQ ID NO: 4-SEQ ID NO: 8.

39. The method of embodiment 35, wherein the plurality of binding agents comprises portions from the same biological molecule.

40. The method of embodiment 35, wherein for each binding agent of the plurality of binding agents, the antigen is attached to the coding tag using mRNA or cDNA display.

41. The method of embodiment 35, wherein the plurality of binding agents comprises at least three different antigens.

42. The method of any one of embodiments 26-41, wherein presence/absence, level, and/or activity the antibody to the antigen in the sample is/are analyzed in e).

43. The method of any one of embodiments 26-42, wherein the plurality of beads comprises the plurality of nucleic acid recording tags, and attaching the pluralities of nucleic acid-bound antibody-binding agent complexes to the plurality of beads in c) comprises nucleic acid hybridization.

44. The method of any one of embodiments 26-43, wherein following binding of the antigen to the antibody, the transfer of identifying information occurs from the coding tag to the recording tag associated with the binding element bound to the antibody, thereby generating the extended recording tag, and wherein the encoder sequence or the complement thereof in the extended recording tag is analyzed in e).

45. The method of embodiment 44, further comprising capping the extended recording tag with a polynucleotide that comprises a universal priming site for sequencing, and the capping comprises hybridizing and/or ligating the polynucleotide to the extended recording tag.

46. The method of embodiment 44, wherein the binding agent is a first binding agent, the method further comprising contacting the mixture of beads with a second binding agent comprising an antibody-binding portion, and (i) a second coding tag comprising identifying information regarding the antibody-binding portion, or (ii) a detectable label; and the method comprises transferring the identifying information in the second coding tag to the extended recording tag to generate a further extended recording tag, or detecting the detectable label.

47. The method of embodiment 44, wherein in c), the binding agent comprises two identical antigens joined together, optionally by a linker, and the encoder sequence in the coding tag of the binding agent comprises identifying information regarding the identical antigen.

48. The method of any one of embodiments 1-47, wherein each of the plurality of samples is independently selected from the group consisting of blood, plasma, serum, urine, and saliva.

49. The method of any one of embodiments 1-48, wherein detecting the antibody in the sample is performed at a limit of detection (LOD) between about 1 pM and about 10 pM.

50. The method of embodiment 49, wherein the LOD of detecting multiple different antibodies in the plurality of samples is no more than 100 µM.

51. The method of any one of embodiments 1-50, wherein detecting the antibody in the sample is performed at a signal-to-noise ratio (SNR) of at least or about 3.

52. The method of embodiment 51, wherein the SNR of detecting multiple different antibodies in the plurality of samples is at least or about 10, at least or about 15, at least or about 20, at least or about 25, at least or about 30, at least or about 35, at least or about 40, at least or about 45, or at least or about 50.

EXAMPLES

The following examples are offered to illustrate but not to limit the methods, compositions, and uses provided herein. Certain aspects of the present invention, including, but not limited to, embodiments for the Proteocode™ polypeptide sequencing assay, information transfer between coding tags and recording tags, methods for attachment of nucleotide-polypeptide conjugate to a support, methods of making nucleotide-polypeptide conjugate, methods of generating barcodes, methods of generating specific binders recognizing an N-terminal amino acid of a polypeptide, reagents and methods for modifying and/or removing an N-terminal amino acid from a polypeptide were disclosed in earlier published application US 2019/0145982 A1, US 2020/0348308 A1, US 2020/0348307 A1, US 2021/0208150 A1, US 2022/0049246 A1, U.S. Pat. No. 11,427,814, US 2022/0227889 A1, US 2022/0283175 A1, the contents of which are incorporated herein by reference in their entireties.

Figure 6:
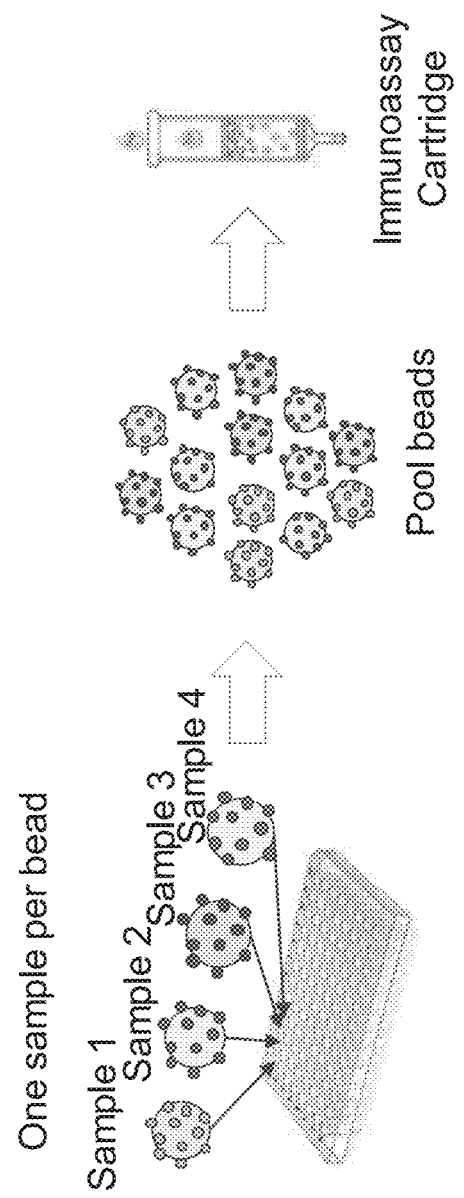
FIG. 6. Exemplary sample multiplexing during the DST assay. Samples containing antibodies are barcoded using barcoded beads. One sample per bead is used, and then beads comprising immobilized antibodies from different samples are pooled together into immunoassay cartridge, where interaction with antigen(s) occurs.

Example 1. Multiplexing Hundreds of Samples in a Single Tube for the DST Assay In this example, it is shown that using NGS readout in the disclosed variants of the DST assay, it is possible to employ massively parallel sample barcoding to combine hundreds of samples in a single tube DST assay. After bead-based sample indexing, the patient antibody samples can be pooled and assayed in a single tube (FIG. 6 and FIG. 7A). In this way, 384 samples are collapsed into a single immunoassay well. The final level of multiplexing occurs at the NGS library level in which each multiplexed DST well on a 384 well plate is barcoded with a well-specific barcode for a total sample throughput of 384 samples/well X 384 wells=~150 k samples per NGS lane or run, greatly facilitating comprehensive population-level humoral response profiling to infectious agents. In addition to sample multiplexing, the disclosed DST assays have the capability of multiplexing thousands of serotyping antigen assays per assay well. A single DST reaction could, for example, analyze 384 patient samples across ~10,000 antigens for a total number of nearly 4 million assays per well. Across a 384 well plate, almost 1.5 billion total assays can be conducted. A single robotic system can process several dozen plates per day enabling serotyping of up to 10 million patients per day on a single robotic instrument. The bottle neck to large-scale epidemiology studies will be in initial sample processing and consolidation into an assay compatible format, as opposed to the serology assay.

Example 2. Preparation of Antigen-Coding Tag Conjugates Using Protein-Oligonucleotide Conjugation Kit An antigen was provided comprising a polypeptide epitope. The conjugation of the polypeptide epitope with exemplary coding tag (/5AmMC6//iSP18/CACTCAGTTTCCGTCATATCGAATCACTCAGT/3SpC3/, SEQ ID NO: 35) was accomplished using Protein-Oligonucleotide Conjugation Kit (Solulink). Briefly, the 5' amine group of the coding tag was modified with S-4FB, and then desalted by 0.5 mL Zeba column. The antigen was modified with S-HyNic, and then desalted by 0.5 mL Zeba column Finally, the 4FB-modified coding tag and HyNic-modified antigen was mixed to prepare antigen-coding tag conjugate, followed by desalting using 0.5 mL Zeba column.

Example 3. Preparation of Antigen-Coding Tag Conjugates Using SpyTag/SpyCatcher Coupling An antigen was provided comprising a polypeptide epitope. The conjugation of the antigen with the coding tag (SEQ ID NO: 35), was accomplished using SpyTag/SpyCatcher protein coupling method. Briefly, the antigen fused to SpyCatcher was expressed in *E. coli* cells, purified by Ni-NTA column, and dialyzed in PBS. The Cys-containing peptide SpyTag (SEQ ID NO: 36) was attached to the 5' amine of amCT_bc4 via SM(PEG)24 (Thermo Fisher). Finally, the SpyTag-modified coding tag and SpyCatcher-fused antigen were mixed to prepare an antigen-coding tag conjugate.

Example 4. Preparation of Antigen-Coding Tag Conjugates Using mRNA Display

An antigen comprising a polypeptide epitope is provided as a DNA sequence encoding the epitope. Individual barcodes are installed to the 3' end of the DNA by performing a PCR reaction with a barcoded primer. If multiple antigens are to be processed in parallel, a DNA library encoding epitope sequences is provided, and individual barcodes are installed to the 3' end of each DNA encoding epitope sequences by performing individual PCR reactions with a barcoded primer. Barcoded DNAs are pooled together. Amplified DNA pools are transcribed using AmpliScribe T7 Flash (Lucigen). Transcription reactions are cleaned up using the RNeasy Mini Kit (Qiagen) and quantified by NanoDrop 3000 (Fisher Scientific). The DNA adaptor is attached to the 3' end of mRNAs using T4 DNA ligase (NEB). Ligated mRNA molecules are purified using 10% TBE-Urea denaturing gel. The mRNA-puromycin molecules are translated in vitro using the PURExpress kit (NEB). During in vitro translation, a stalled ribosome allows the puromycin residue to enter the ribosome A-site and attach to the C-terminus of the protein, creating a protein-mRNA fusion. The protein-mRNA fusions are captured via complementary oligonucleotides attached to silica beads. The mRNA portions are converted into cDNA using ProtoScript II Reverse Transcriptase (NEB). The protein-cDNA/RNA pools are treated with RNase H (NEB) and RNase cocktail (Thermo Fisher) to generate protein-cDNA, and then purified by a cut-out filter. The complementary sequence to the type II restriction site in cDNA is added to form a double strand, and incubated with the restriction enzyme to generate spacer sequence (Sp) at the 3' end of cDNA (FIG. 8).

Example 5. Preparation of DST Beads for Antibody Immobilization Using SpyC Fusion Protein This example shows an exemplary method of immobilization of antibody molecules from biological samples using a SpyTag-SpyCatcher bioconjugation system (U.S. Pat. No. 9,547,003 B2). A SpyTag peptide is attached to DST beads via a capture DNA (FIG. 4A). A sample-specific barcode and optional UMI is included in the DNA tag on the DST beads enabling sample barcoding by adding different barcoded beads to each sample; alternatively, sample barcoding can be accomplished post-immunoglobulin enrichment by adding an adapter barcode to each enrichment well.

A fusion protein consisting of SpyCatcher-Protein A/G (SEQ ID NO: 38) is expressed in *E. coli* cells and purified using standard Immobilized metal affinity chromatography (IMAC) procedures as described by (Dovala, et al. 2016. "Rapid Analysis of Protein Expression and Solubility with the SpyTag-SpyCatcher System." Protein Expression and Purification 117 (January): 44-51).

The SpyCatcher-Protein A/G fusion protein is incubated with the DST beads comprising the SpyTag peptide, covalently coupling the fusion protein to the DST beads (FIG. 4A). After coupling, a sample comprising antibodies is incubated with DST beads to capture IgG or IgM. Conditions for a test capture were as follows. Specific antibodies were spiked-in in the PBS-T buffer (1×PBS, 0.1% Tween 20, pH 7.4) in pM to nM range. Serum was diluted with 1:100 to 1:1000 dilution. Capture was performed for 1 h at room temperature without shaking or agitation in 100 μL volume per well or tube.

Produced in this example, the uniquely barcoded DST beads act as IgG/IgM/IgA capture beads. The beads bind serum antibodies from individual samples. After binding, the beads is washed in the PBS-T buffer, and then optionally IgG/IgM/IgA molecules captured on beads may be cross-linked via standard methods. In one example, the NHS cross-linker clisuccinimidyl suberate (DSS) was employed to couple bound immunoglobulins to the immobilized A/G fusion proteins. In another example, the bissulfosuccinimidyl suberate (BS3) cross-linker was employed to couple bound immunoglobulins to the immobilized A/G fusion proteins. Exemplary crosslinking conditions are as follows. 2 mM BS3 in PBS-T (200 μL) were added in each well and incubated at room temperature for 1 h. Then, 10 μL of 1 M Tris-HCl (pH=7.4) were added and incubated for 15 mM under the same conditions. Wells were washed with PBS-T 3 times. Then, 200 μL of 0.1 M glycine-HCl (pH=2.7) were added and incubated at 37° C. for 30 min. Wells were washed twice with the same solution, and then twice with the PBS-T buffer.

Normalization of immunoglobulins from each sample can be controlled by using a fixed amount of beads per sample under saturating serum immunoglobulin concentrations. The total number of immunoglobulins captured per sample can also be controlled by titrating surface density of capture sites on the bead. Beads from multiple samples are pooled and a single-well immunoassay performed on the pooled sample beads using a polynucleotide-tagged peptide antigen library to initiate the DST assay (FIG. 6).

Figure 5B:
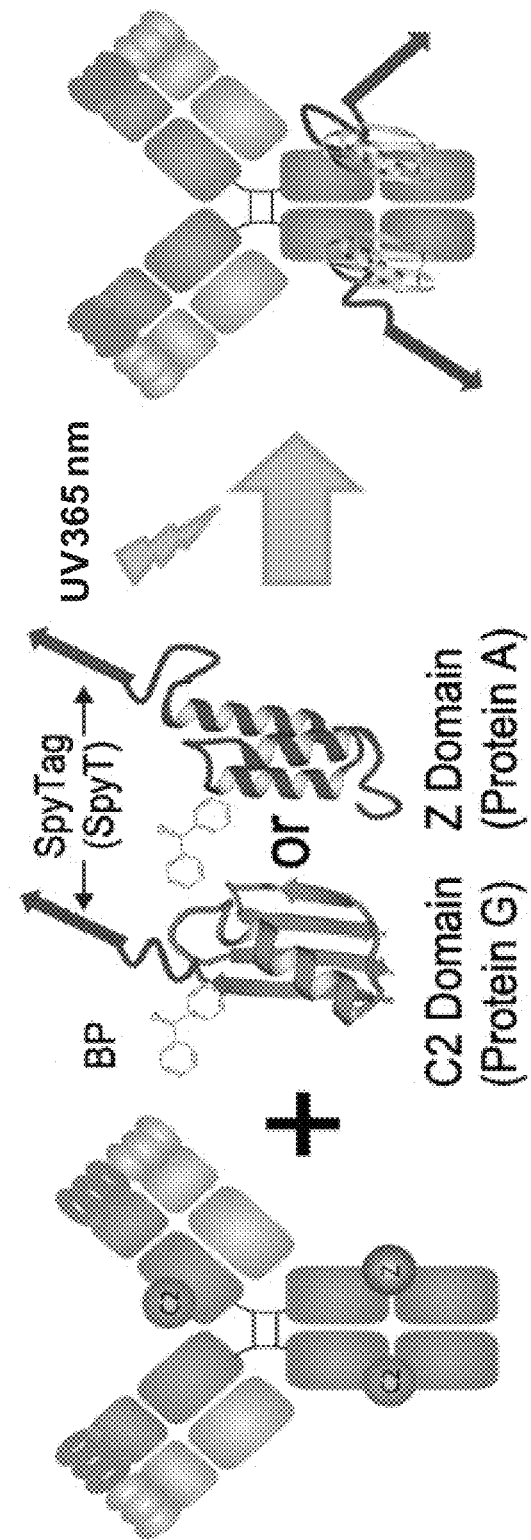

Example 6. Preparation of DST Beads for Antibody Immobilization Using SpyC-SnpC Fusion Protein, Followed by Crosslinking of Immobilized Antibodies to Prevent Exchange This example shows an exemplary method of antibody immobilization that can be used as an alternative to the method of Example 5. Photoaffinity-based crosslinking is used in this Example to prevent potential exchange of immobilized antibody molecules between barcoded DST beads. For this purpose, short polypeptide subdomains (~55-60 amino acids) of Protein A and Protein G, known as Z domain (SEQ ID NO: 44) and C2 domain (SEQ ID NO: 45), respectively, can be used that bind IgG (C2 or Z) or IgM (C2) with low nM affinity (Perols and Karlstrom, "Site-specific photoconjugation of antibodies using chemically synthesized IgG-binding domains" Bioconjug Chem (2014), 25(3): 481-488). Modified C2 or Z domain polypeptides also have the capability of covalent photoaffinity coupling to bound IgGs/IgM molecules using synthetic incorporation of benzophenone (BP) or 4-benzoylphenylalanine (BPA) moieties (Perols and Karlstrom, 2014; Kanje S, et al., "Next generation of labeling reagents for quantitative and multiplexing immunoassays by the use of LA-ICP-MS." Analyst (2016), 141(23): 6374-6380) (FIG. 5B).

A SpyTag peptide is attached to barcoded DST beads via a capture DNA as described in Example 5. A fusion protein comprising SpyCatcher-SnoopCatcher (SEQ ID NO: 37) with an N-terminal His-tag is expressed in *E. coli* cells and purified using standard Immobilized metal affinity chromatography (IMAC) procedures as described by Dovala et al. 2016; 117 (January): 44-51. The SpyCatcher-SnoopCatcher fusion protein is incubated with the barcoded DST beads comprising the SpyTag peptide and with the SnoopTag-Z protein conjugate, effectively covalently bridging Z protein to the barcoded DST beads (FIG. 6). Alternatively, the SnoopTag—C2 protein conjugate can be used to covalently bridge C2 protein to the barcoded DST beads. After bridging, a sample comprising antibodies is incubated with DST beads to capture IgG (when Z protein is immobilized) or IgM (when C2 protein is immobilized) molecules. The Z or C2 beads include a barcode on the recording tag to identify an IgG versus IgM response. An optional photoaffinity label such as benzophenone (BP) can be engineered into the Z or C2 subdomains as described by (Perols and Karlström, 2014. "Site-Specific Photoconjugation of Antibodies Using Chemically Synthesized IgG-Binding Domains." Bioconjugate Chemistry 25 (3): 481-88) to covalently immobilize the captured IgG or IgM molecules to the DST beads. Namely, after antibody capture on the Z or C2 beads, the BP-derivatized Z or C2 proteins are cross-linked to the capture antibodies by exposure to UV 365 nm light for 1-2 hours on ice in a 48-well plate using a standard Ultraviolet Cross-linker apparatus equipped with 5×8 UV-A tubes.

Example 7. An Exemplary DST Assay to Detect Antibodies in Serum Samples Having High Affinity Epitope Binding In this example, the barcoded DST beads prepared according to Example 5 are used comprising an immobilized recording tag. For optional normalization of the signal, internal standard (IntStd) beads are used that are similar to the DST beads, comprise the immobilized SpyTag peptide, but do not comprise SpyCatcher-Protein A/G fusion protein, and thus unable to bind antibodies from samples.

The barcoded DST beads were added to an Eppendorf tube and diluted with the PBS-T buffer (1×PBS, 0.1% Tween 20, pH 7.4) to about 2000 DST beads per 40 μL. When internal standard (IntStd) beads are used, they are added at 10:1 DST/IntStd beads ratio. 50 μL of PBS-T were dispensed into each well of a filter plate; then 40 μL of the vortexed beads slurry were dispensed into the appropriate wells.

Antibody serum samples were diluted 100-fold with the PBS-T buffer and 100 μL of each diluted sample were added to corresponding wells of the filter plate. The filter plate was incubated at 25° C. for 30 min. Then, wells in the filter plate were washed 2-3 times with 200 μL of PBS-T and drained. 100 μL of BOC solution (2 nM of coding tag-antigen conjugate, 1× PBS, 0.1% Tween 20, pH 7.4) was added to wells and incubated at 25° C. for 30 mM to allow binding between immobilized antibodies and cognate antigens. Then, wells in the filter plate were washed 2 times with 200 µL of BWH buffer (1×PBS-T, 500 mM NaCl) and drained. 150 µL of EMM solution (0.125 mM dNTPs mix, 0.125 unit/µL Klenow Exo-, 1× Klenow Exo-buffer) are added to wells and incubated at 25° C. for 5 mM to allow hybridization between proximal coding tags and recording tags, followed by nucleotide extension on the recording tags producing extended recording tags. During hybridization and extension reactions, information regarding antigen attached to the coding tag is transferred to the recording tag. Then, wells in the filter plate are washed with 200 µL of PBS-T, followed by washing with 200 µL of SHT solution (0.1 M NaOH, 0.1% Tween 20), followed by washing twice with 200 µL of PBS-T. 150 µL of Capping solution (0.125 mM dNTPs mix, 0.125 unit/uL Klenow Exo-, 0.4 uM capping oligo, 1× Klenow Exo-buffer) are added to wells and incubated at 25° C. for 10 mM to allow hybridization of the capping oligo with the recording tags, which provides the extended recording tags with the priming sequence used later during NGS preparation. Corresponding beads are retrieved from wells and added to PCR reactions amplifying the extended recording tags using a sequencing primer complementary to the priming sequence. Products of PCR reactions are subjected to NGS procedure, and sequence information from the extended recording tags is used to identify antigens that specifically bound to the immobilized antibodies in the samples.

Example 8. Limit of Detection (LOD) for the DST Assay Using Anti-HM Antibodies An antibody targeting the HM-epitope tag was diluted with either PBS-T buffer (left graph) or diluted human serum (1:500 dilution in PBS-T, right graph) to assess the antibody detection limit in different matrices. Resulting samples were exposed to DST beads having recording tags attached to immobilize antibodies, and were subsequently washed to remove excess and non-specifically bound material. For the DST assay, antibodies attached to the beads were incubated with 0.5 nM of coding tag-barcoded HM peptides; then, beads were washed with PBS-T twice to remove unbound material. Encoding reactions were performed to register the antibody-epitope binding interaction, indicated by transfer of coding tag information onto corresponding recording tags, generating extended recording tags. Then, beads were subjected to an additional DNA "capping" process to append PCR primer sequences to extended recording tags. Finally, the recording tags further extended after the capping step were amplified by PCR using the appended PCR primers, and the resulting PCR products were analyzed by next-generation sequencing (NGS) using an Illumina MiSeq; DNA sequences were processed to determine the identity and number of recording tags having specific DNA recording tag/coding tag combinations. Experiments were performed in triplicate. Detection limits of 1 pM and 10 pM (signal-to-noise=3) were observed in PBS-T and diluted human serum, respectively, as shown in FIG. 9.

Example 9. Selection of Peptide Antigens (Peptide Epitopes) for DST Serotyping Assays Influenza A exhibits 18 different hemagglutinin subtypes (H1-H18) and 11 different neuraminidase subtypes (N1-N11). The most common subtypes of influenza A are H1N1 and H3N2, and most flu vaccines in the United States protect against three to four different influenza subtypes including A-H1N1, A-H3N2 virus, and two influenza B viruses.

Influenza DNA-tagged peptide antigens are derived from pathogen, subtype, and strain-specific peptide sequences. After the DST assay, NGS readout will deconvolute (decode) antigen/antibody interactions for each individual donor. Most influenza serology assays use peptides or subdomains from subtypes of the influenza hemagglutinin (HA, 565 amino acids), and neuraminidase (NA, 469 amino acids) surface proteins. A set of linear peptide epitopes can be used that derived from HA sequences chosen from the two WHO recommended predominant influenza subtypes for inclusion in vaccines, H1N1 and H3N2, from strains from 2015-2019 years (World Health Organization Recommendations for Composition of Influenza Vaccines; Influenza Research Database). For 2019, the two recommend Influenza A virus subtypes and strains are: Influenza A H1N1-A/Brisbane/02/2018 (H1N1) pdm09-like virus and Influenza A H3N2-A/Kansas/14/2017 (H3N2)-like virus. The peptide sequences, with validated serology response, can be extracted from the Immune Epitope Database and Analysis Resource and Influenza Research Database. The Virus Pathogen Database (Virus Pathogen Resource, or VIPR) can also be used for evaluating antigenicity of epitopes. For the initial design of H1N1 and H3N2 subtype assays, ~10 total peptide per strain tiled across the HA protein were employed using the B cell epitope prediction algorithm, BepiPred-2. (Jespersen, Peters et al. 2017). Additional peptide epitopes from different pathogens were selected from the following proteins: spike glycoprotein (QHR63260); nucleocapsid phosphoprotein (QHQ82471); leader protein (YP_009725297); Nucleoprotein (Nucleocapsid protein) (NC) (Protein N) (P59595); nonstructural protein NS3 (QHR63261). Some of the exemplary viral-derived peptides that were used and may be used in the disclosed DST methods are set forth in Table 1 and in SEQ ID NOs: 4-34.

A set of the selected peptide epitopes that were used in the experiments as conjugates with coding tags (CT) as described in FIG. 12, FIG. 13A, FIG. 13B and FIG. 14-FIG. 18 is shown in the Table 1.

TABLE 1

Description of the selected peptide epitopes used as conjugates with coding tags (CT).

| CT-epitope | SEQ ID NO: | Peptide description | Peptide sequence |
|---|---|---|---|
| 1 | 4 | Cov2 Spike protein AA547 - 570 | TGTGVLTESNKKFLPFQQFGRDIAGGK |
| 2 | 5 | Cov2 Spike protein_AA782 - 805 | FAQVKQIYKTPPIKDFGGFNFSQIGGK |

TABLE 1-continued

Description of the selected peptide epitopes used as conjugates with coding tags (CT).

| CT-epitope | SEQ ID NO: | Peptide description | Peptide sequence |
|---|---|---|---|
| 3 | 6 | Cov2 Spike protein_AA807 - 830 | PDPSKPSKRSFIEDLLFNKVTLADGGK |
| 4 | 7 | Cov2 Spike protein_AA1138 - 1161 | YDPLQPELDSFKEELDKYFKNHTSGGK |
| 5 | 8 | Cov2 Spike protein_AA1247 - 1270 | SSSSGSSSKFDEDDSEPVLKGVKLGGK |
| 6 | 9 | Cov2 Nucleocapsid protein_AA154 - 183 | NAAIVLQLPQGTTLPKGFYAEGSRGGSQASGGK |
| 7 | 10 | Cov2 Nucleocapsid protein_AA215 - 244 | GDAALALLLLDRLNQLESKMSGKGQQQQGQGGK |
| 8 | 11 | Cov2 Nucleocapsid protein_AA238 - 260 | GQQQQGQTVTKKSAAEASKKPRQGGK |
| 9 | 12 | Cov2 Nucleocapsid protein_AA358 - 381 | DAYKTFPPTEPKKDKKKADETQAGGK |
| 10 | 13 | Cov2 Nucleocapsid protein_AA382 - 405 | LPQRQKKQQTVTLLPAADLDDFSKGGK |
| 11 | 14 | Human adenovirus C_nucleoprotein | PGPRPPTRRQRHDRQRGLVWEDDDGGK |
| 12 | 15 | Enterovirus B_genome polyprotein | SNSESIPALTAAETGHTSQVGGK |
| 13 | 16 | Eppstein-Barr_nucleoprotein | RRPPPGRRPFFHPVAGGK |
| 14 | 17 | Human herpesvirus 1_Envelope glycoprotein D | RRHTQKAPKRIRLPHIREDDQPSSHQPLFYGGK |
| 15 | 18 | Rhinovirus A public epitope | NPIENYVDEVLNEVLVVPNINSSHPGGK |
| 16 | 19 | HIV-1 public epitope | QDNSDIKVVPRRKAKIIRDYGKQMAGGK |
| 17 | 20 | HA peptide | YPYDVPDYASLGGK |
| 18 | 21 | Scrambled (random) HA peptide | YADVYPSYPDLGGK |

Example 10. Solution-Phase Antibody Tagging with Photocrosslinking DNA Tagged Immunoglobulin Affinity Agent Human serum antibodies are labeled with the oYo-Link® Oligo Custom conjugation kit (Alpha Thera, PA) by incubating 1 µl of serum (~5-10 ug/ul IgG) diluted in 14 µl PBS with 5 µl oYo-Link Custom Oligo (sample-specific barcode DNA tag appended to a modified Protein G subdomain with BPA photo-crosslinking agent) for 15 mM. The sample is then exposed, on ice, to long wave length UV365 nm irradiation (10 W at ~3 cm) for 90 mM using the LEPDX UV 365 nm lamp or similar device. After photo-crosslinking, excess oYo-Link Custom Oligo is removed using ultrafiltration through a 100 kDa MWCO device.

The derivatized antibodies within the antibody/serum mix are attached to ProteoCode™ beads using hybridization and ligation to the hairpin recording tags. Namely, the 20 µl of derivatized antibody/serum mix is mixed with 20 µl 12×SSPE and incubated for 30 min. at 37° C. to capture the derivatized antibodies via hybridization. The ProteoCode beads are washed once in 6×SSPE and twice in PBS buffer. After washing, the antibody DNA tag is ligated to the recording tag capture hairpins using standard T4 DNA ligase conditions.

Example 11. Solution-Phase Antibody Tagging with a DNA Tag Through an Hydrazone Reaction and Formation of a bis-arylhydrazone Bioconjugate Using a modified protocol from U.S. Pat. No. 8,846,875 B2, incorporated herein by reference, serum or plasma antibodies are affinity purified with protein A/G resin and labeled using a hydrazone bioconjugation reaction. After purification, the antibodies are eluted and resuspended in Modification Buffer (100 mM phosphate, 150 mM NaCl, pH 7.4) at 1 mg/ml for bioconjugation. The heterobifunctional linker, S-HyNic is used to incorporate 6-hydrazinonicotinamide (HyNic) groups using a succinimide ester (NHS ester) that readily reacts with amino groups on antibodies. After installation of HyNic groups on the antibodies, 4-formylbenzamide (41-B)-modified oligonucleotides (3 mol equivalent) are mixed with HyNic antibodies (1 mol equivalent), in the presence of aniline-based Conjugation Buffer (100 mM phosphate, 150 mM NaCl, 10 mM aniline, pH 6.0) and incubated for 2 hrs at room temp., to efficiently generate a bis-arylhydrazone covalent linkage between the antibody and oligonucleotide. After the reaction, excess oligo and aniline reagent is removed using a 100 kD MWCO filter.

Example 12. Synthesis of Library of Antigen-DNA Conjugates Via cDNA Display of a DNA Library As shown in FIG. 8, a large pool of peptide-DNA conjugates for use in the DST assay is generated by cDNA synthesis from a DNA library generated from array-based synthetic oligonucleotide synthesis (e.g., Twist Biosciences, Agilent, etc.). Using a protocol adapted from Ladner et al., the DNA library (pool of ssDNA templates) are PCR-amplified and the dsDNA products are used as templates for an in vitro transcription-translation (IVTT) reaction (Ladner, 2021). An Ampliscribe IVT kit is used to generate mRNA from the DNA library. The resulting mRNA is ligated to a hairpin oligonucleotide adaptor bearing a puromycin molecule tethered by a PEG spacer and, following buffer exchange, the reaction mix is used as a template in an in vitro translation reaction (PURExpress, NEB). Constructs bearing mRNA—comprising of (i) mRNA, (ii) mRNA+adaptor, (iii) mRNA+adaptor+peptide—are captured using magnetic beads coated with a biotinylated DNA oligo complementary to a 30 nt sequence in the mRNA constant region. A reverse transcription reaction, primed by the adaptor hairpin, is used to generate cDNA, after which RNase was applied to remove mRNA. The resultant product is buffer-exchanged, quantified, and used without further modifications or purification.

Example 13. Sample Multiplexing During Encoding Reactions

Several experiments were performed to demonstrate possibility to analyze multiple antibody samples in a single DST assay. In one example, nine serum samples were analyzed simultaneously in the automated instrument performing the DST assay as disclosed in Example 7. The 9 samples comprise 3 samples from 3 different subjects, wherein for each subject the blood samples were taken before COVID-19 vaccination, after the 1st vaccine shot and after the 2nd vaccine shot (see FIG. 18). The experiments in the automated instrument were performed as a quadruplet (4 different cartridges) to ensure the reproducibility. Description of peptide epitopes used in this experiment is provided in Table 1. FIG. 18 illustrates that there are specific epitopes are particularly suitable for detection of antibodies generated after the COVID-19 vaccination, such as CT-epitopes #1 and #4.

In another example, successful multiplexing of 96 samples in a single DST assay is shown in FIGS. 19A-19B. 96 unique oligonucleotides were synthesized representing 96 unique sample-specific barcodes. Each oligonucleotide was ligated to a DBCO-modified stub DNA (17 nt/5Phos/AGA/iAmMC6T/CGGAAGAGCGTCG; SEQ ID NO: 49), creating a second set of 96 unique oligonucleotides (shown in FIG. 19A, $1^{st}$ step). Next, each group of oligonucleotides was attached to a separate plurality of beads (NHS-Activated Sepharose High Performance, Cytiva, USA) containing attached capture hairpin DNAs, generating 96 unique oligonucleotide-labeled pluralities of beads. The capture hairpin DNAs were conjugated to the beads using trans-cyclooctene (TCO) and methyltetrazine (mTet)-based click chemistry and each comprise the following sequence:

SEQ ID NO: 50
CACTCAGTCCATTAACNNNNNNNNNNNCTAGTGTCGCGGACTACGCATTAC

TGAGAAGCTTGCTAGTCGACGTGGTCCTTTTGGACCACGTCGACTAG, .

Immobilization of DBCO-modified oligonucleotides on beads was performed as follows: each oligonucleotide was hybridized and ligated to a capture hairpin DNA immobilized on beads in 1× Quick Ligation Reaction Buffer (66 mM Tris-HCl, 10 mM $MgCl_2$, 1 mM Dithiothreitol, 1 mM ATP, 7.5% PEG 6000, pH 7.6 at 25° C., New England Biolabs, USA) and 2000 U of T4 DNA ligase (New England Biolabs, USA). Each DBCO-modified oligonucleotide-ligated beads set was washed once with PBS+0.1% Tween 20, three times with 0.1 M NaOH+0.1% Tween 20, and 3 three times with PBS+0.1% Tween 20 (shown in FIG. 19A, $2^{nd}$ and $3^{rd}$ steps). Next, a collection of peptides (96 different peptides each having 12 amino acid residues and Lys modified with azide at the C-terminus) was conjugated to the DBCO-modified oligonucleotide-ligated beads using DBCO-azide click chemistry (using the following conditions: 100 mM HEPES buffer, pH 8.0 at 60° C. for 12 hours), generating 96 unique pluralities of beads comprising attached oligonucleotide-peptide conjugates (shown in FIG. 19A, $4^{th}$ step). These pluralities of beads mimic pluralities of antibody-bound beads prepared in the DST assay from 96 different samples.

Next, 96 unique oligonucleotide-labeled pluralities of beads were pooled together (shown in FIG. 19A, $5^{th}$ step) and assayed simultaneously. To demonstrate that all 96 unique oligonucleotide barcodes can be identified after NGS, a capping step was performed by adding Illumina adaptor primers to the pooled beads, followed by performing PCR reaction using the adaptor primers. Each of 96 unique oligonucleotides (barcodes) were bioinformatically identified (FIG. 19B), showing that these oligonucleotides can be used as oligonucleotides comprising sample barcodes for labeling and identification of 96 different antibody samples. Antibodies from the samples can be immobilized on oligonucleotide-labeled pluralities of beads using methods disclosed in the examples above; the beads can be pooled together and processed in the exemplary DST assay as shown in Example 7, identifying immobilized antibody molecules. In other embodiments, higher numbers of unique oligonucleotides can be utilized in the same way, offering possibility to analyze 100, 200, 500, 1000, or more antibody samples in a single DST assay.

The present disclosure is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for sample analysis, comprising:
a) (i) separately contacting a plurality of different antibodies of each sample of a plurality of samples with a binding element configured to bind to the plurality of different antibodies in the sample, thereby obtaining binding element-antibody conjugates, wherein the binding element is configured to bind to an antibody constant region and is not configured to bind to an antibody variable region; and
(ii) attaching either the binding element or the binding element-antibody conjugates to a bead, wherein the binding element is attached to the bead before or after contacting the plurality of different antibodies,
wherein the binding element is associated with a recording tag comprising a sample-specific barcode before or after attachment to the bead, thereby obtaining a plurality of beads comprising attached binding element-antibody conjugates each associated with the recording tag from each sample;
b) mixing the pluralities of beads comprising attached binding element-antibody conjugates from the plurality of samples, thereby obtaining a mixture of beads;
c) contacting the mixture of beads with a binding agent comprising an antigen and a coding tag attached thereto, wherein the coding tag comprises an encoder sequence that comprises identifying information regarding the antigen;
d) following binding of the antigen to an antibody attached to a bead of the mixture of beads, allowing transfer of identifying information between the coding tag and the recording tag of the bead, thereby generating an extended coding tag or an extended recording tag, wherein the transfer occurs through a primer extension reaction and/or ligation; and
e) analyzing the encoder sequence or a complement thereof and the sample-specific barcode or a complement thereof in the extended coding tag or the extended recording tag, wherein the analyzing comprises nucleic acid sequencing, to identify the antigen and the sample that contains the antibody, thereby detecting the antibody in the sample.

2. The method of claim 1, wherein in a), beads comprising the attached binding element and the recording tag comprising a sample-specific barcode and associated with the binding element are contacted with the plurality of different antibodies of each sample.

3. The method of claim 1, wherein the plurality of samples comprises at least 9 samples, at least 50 samples, at least 96 samples, at least 500 samples, or at least 1,000 samples.

4. The method of claim 3, wherein each sample of the plurality of samples is obtained from a different subject.

5. The method of claim 1, wherein the antigen comprises a polypeptide comprising an amino acid sequence from 7 to 30 amino acid residues.

6. The method of claim 1, wherein the binding element comprises an immunoglobulin Fc-binding domain.

7. The method of claim 1, further comprising covalently cross-linking the antibodies to the binding element in the plurality of beads comprising attached binding element-antibody conjugates in a) or b).

8. The method of claim 1, wherein the antigen comprises a peptide sequence from a SARS-COV-2 virus, and the method detects an antibody that binds to the peptide sequence.

9. The method of claim 1, wherein in c), the mixture of beads is contacted with a plurality of binding agents each comprising a different antigen, wherein each different antigen is attached to a different coding tag comprising an encoder sequence that comprises identifying information regarding the antigen attached thereto.

10. The method of claim 9, wherein the plurality of binding agents comprises one or more amino acid sequences each having at least 95% sequence identity to an amino acid sequence selected from the group consisting of SEQ ID NO: 4-SEQ ID NO: 13.

11. The method of claim 9, wherein the plurality of binding agents comprises at least three different antigens.

12. The method of claim 1, wherein following binding of the antigen to the antibody, the transfer of identifying information occurs from the coding tag to the recording tag associated with the binding element bound to the antibody, thereby generating the extended recording tag, and wherein the encoder sequence or the complement thereof in the extended recording tag is analyzed in e).

13. The method of claim 12, wherein the binding agent is a first binding agent, the method further comprising:

(i) contacting the mixture of beads with a second binding agent comprising:
an antibody-binding portion, and
a second coding tag comprising identifying information regarding the antibody-binding portion; and
(ii) transferring the identifying information in the second coding tag to the extended recording tag to generate a further extended recording tag.

14. The method of claim 1, wherein in c), the binding agent comprises two identical antigens joined together, and the encoder sequence in the coding tag of the binding agent comprises identifying information regarding the antigen of the binding agent.

15. The method of claim 1, wherein a limit of detection (LOD) of detecting each of the different antibodies in the plurality of samples is no more than 100 pM.

16. A method for sample analysis, comprising:
a) separately contacting each sample of a plurality of samples with i) a nucleic acid tag comprising a sample-specific barcode, and ii) a binding element configured to bind to a plurality of different antibodies in the sample, thereby obtaining a plurality of complexes from each sample, wherein each complex for the sample comprises the nucleic acid tag and the binding element which is configured to bind to an antibody constant region and is not configured to bind to an antibody variable region;
b) mixing the pluralities of complexes from the plurality of samples and attaching them on a plurality of beads, thereby obtaining a mixture of beads comprising a plurality of attached antibodies each associated with a nucleic acid tag;
c) contacting the mixture of beads with a binding agent comprising an antigen and a coding tag attached thereto, wherein the coding tag comprises an encoder sequence that comprises identifying information regarding the antigen;
d) following binding of the antigen to an antibody attached to a bead of the mixture of beads, allowing transfer of identifying information between (i) the coding tag attached to the antigen and (ii) the nucleic acid tag associated with the antibody attached to the bead, thereby generating an extended coding tag or an extended nucleic acid tag, wherein the transfer occurs through a primer extension reaction and/or ligation; and
e) analyzing the encoder sequence or a complement thereof and the sample-specific barcode or a complement thereof in the extended coding tag or the extended nucleic acid tag, wherein the analyzing comprises nucleic acid sequencing, to identify the antigen and the sample that contains the antibody, thereby detecting the antibody in the sample.

17. The method of claim 16, wherein the binding element comprises the nucleic acid tag comprising the sample-specific barcode.

18. The method of claim 16, wherein the plurality of samples comprises at least 9 samples, at least 50 samples, at least 96 samples, at least 500 samples, or at least 1,000 samples.

19. The method of claim 16, wherein the binding element comprises an immunoglobulin Fc-binding domain.

20. The method of claim 16, wherein in c), the mixture of beads is contacted with a plurality of binding agents each comprising a different antigen, wherein each different antigen is attached to a different coding tag comprising an encoder sequence that comprises identifying information regarding the antigen attached thereto, and wherein the plurality of binding agents comprises at least three different antigens.

21. The method of claim 12, wherein the binding agent is a first binding agent, the method further comprising:
(i) contacting the mixture of beads with a second binding agent comprising an antibody-binding portion and a detectable label; and
(ii) detecting the detectable label.

22. The method of claim 14, wherein the two identical antigens are joined together by a linker.

* * * * *

SEQUENCE LISTING

```
Sequence total quantity: 50
SEQ ID NO: 1              moltype = AA   length = 7
FEATURE                   Location/Qualifiers
source                    1..7
                          mol_type = protein
                          organism = synthetic construct
REGION                    1..7
                          note = Peptide linker
SITE                      7
                          note = modified with azide
SEQUENCE: 1
GSGSGSK                                                                     7

SEQ ID NO: 2              moltype = DNA   length = 20
FEATURE                   Location/Qualifiers
source                    1..20
                          mol_type = other DNA
                          organism = synthetic construct
misc_feature              1..20
                          note = P5 primer
SEQUENCE: 2
aatgatacgg cgaccaccga                                                      20

SEQ ID NO: 3              moltype = DNA   length = 24
FEATURE                   Location/Qualifiers
source                    1..24
                          mol_type = other DNA
                          organism = synthetic construct
misc_feature              1..24
                          note = P7 primer
SEQUENCE: 3
caagcagaag acggcatacg agat                                                 24

SEQ ID NO: 4              moltype = AA   length = 27
FEATURE                   Location/Qualifiers
source                    1..27
                          mol_type = protein
                          organism = synthetic construct
REGION                    1..27
                          note = CT epitope 1
SEQUENCE: 4
TGTGVLTESN KKFLPFQQFG RDIAGGK                                              27

SEQ ID NO: 5              moltype = AA   length = 27
FEATURE                   Location/Qualifiers
source                    1..27
                          mol_type = protein
                          organism = synthetic construct
REGION                    1..27
                          note = CT epitope 2
SEQUENCE: 5
FAQVKQIYKT PPIKDFGGFN FSQIGGK                                              27

SEQ ID NO: 6              moltype = AA   length = 27
FEATURE                   Location/Qualifiers
source                    1..27
                          mol_type = protein
                          organism = synthetic construct
REGION                    1..27
                          note = CT epitope 3
SEQUENCE: 6
PDPSKPSKRS FIEDLLFNKV TLADGGK                                              27

SEQ ID NO: 7              moltype = AA   length = 27
FEATURE                   Location/Qualifiers
source                    1..27
                          mol_type = protein
                          organism = synthetic construct
REGION                    1..27
                          note = CT epitope 4
SEQUENCE: 7
YDPLQPELDS FKEELDKYFK NHTSGGK                                              27

SEQ ID NO: 8              moltype = AA   length = 27
FEATURE                   Location/Qualifiers
source                    1..27
                          mol_type = protein
                          organism = synthetic construct
```

```
REGION                  1..27
                        note = CT epitope 5
SEQUENCE: 8
SSSSGSSSKF DEDDSEPVLK GVKLGGK                                            27

SEQ ID NO: 9            moltype = AA  length = 33
FEATURE                 Location/Qualifiers
source                  1..33
                        mol_type = protein
                        organism = synthetic construct
REGION                  1..33
                        note = CT epitope 6
SEQUENCE: 9
NAAIVLQLPQ GTTLPKGFYA EGSRGGSQAS GGK                                     33

SEQ ID NO: 10           moltype = AA  length = 33
FEATURE                 Location/Qualifiers
source                  1..33
                        mol_type = protein
                        organism = synthetic construct
REGION                  1..33
                        note = CT epitope 7
SEQUENCE: 10
GDAALALLLL DRLNQLESKM SGKGQQQQGQ GGK                                     33

SEQ ID NO: 11           moltype = AA  length = 26
FEATURE                 Location/Qualifiers
source                  1..26
                        mol_type = protein
                        organism = synthetic construct
REGION                  1..26
                        note = CT epitope 8
SEQUENCE: 11
GQQQQGQTVT KKSAAEASKK PRQGGK                                             26

SEQ ID NO: 12           moltype = AA  length = 27
FEATURE                 Location/Qualifiers
source                  1..27
                        mol_type = protein
                        organism = synthetic construct
REGION                  1..27
                        note = CT epitope 9
SEQUENCE: 12
DAYKTFPPTE PKKDKKKKAD ETQAGGK                                            27

SEQ ID NO: 13           moltype = AA  length = 27
FEATURE                 Location/Qualifiers
source                  1..27
                        mol_type = protein
                        organism = synthetic construct
REGION                  1..27
                        note = CT epitope 10
SEQUENCE: 13
LPQRQKKQQT VTLLPAADLD DFSKGGK                                            27

SEQ ID NO: 14           moltype = AA  length = 27
FEATURE                 Location/Qualifiers
source                  1..27
                        mol_type = protein
                        organism = synthetic construct
REGION                  1..27
                        note = CT epitope 11
SEQUENCE: 14
PGPRPPTRRQ RHDRQRGLVW EDDDGGK                                            27

SEQ ID NO: 15           moltype = AA  length = 23
FEATURE                 Location/Qualifiers
source                  1..23
                        mol_type = protein
                        organism = synthetic construct
REGION                  1..23
                        note = CT epitope 12
SEQUENCE: 15
SNSESIPALT AAETGHTSQV GGK                                                23

SEQ ID NO: 16           moltype = AA  length = 18
FEATURE                 Location/Qualifiers
source                  1..18
                        mol_type = protein
```

-continued

```
                        organism = synthetic construct
REGION                  1..18
                        note = CT epitope 13
SEQUENCE: 16
RRPPPGRRPF FHPVAGGK                                                18

SEQ ID NO: 17           moltype = AA  length = 33
FEATURE                 Location/Qualifiers
source                  1..33
                        mol_type = protein
                        organism = synthetic construct
REGION                  1..33
                        note = CT epitope 14
SEQUENCE: 17
RRHTQKAPKR IRLPHIREDD QPSSHQPLFY GGK                               33

SEQ ID NO: 18           moltype = AA  length = 28
FEATURE                 Location/Qualifiers
source                  1..28
                        mol_type = protein
                        organism = synthetic construct
REGION                  1..28
                        note = CT epitope 15
SEQUENCE: 18
NPIENYVDEV LNEVLVVPNI NSSHPGGK                                     28

SEQ ID NO: 19           moltype = AA  length = 28
FEATURE                 Location/Qualifiers
source                  1..28
                        mol_type = protein
                        organism = synthetic construct
REGION                  1..28
                        note = CT epitope 16
SEQUENCE: 19
QDNSDIKVVP RRKAKIIRDY GKQMAGGK                                     28

SEQ ID NO: 20           moltype = AA  length = 14
FEATURE                 Location/Qualifiers
source                  1..14
                        mol_type = protein
                        organism = synthetic construct
REGION                  1..14
                        note = CT epitope 17
SEQUENCE: 20
YPYDVPDYAS LGGK                                                    14

SEQ ID NO: 21           moltype = AA  length = 14
FEATURE                 Location/Qualifiers
source                  1..14
                        mol_type = protein
                        organism = synthetic construct
REGION                  1..14
                        note = CT epitope 18
SEQUENCE: 21
YADVYPSYPD LGGK                                                    14

SEQ ID NO: 22           moltype = AA  length = 21
FEATURE                 Location/Qualifiers
source                  1..21
                        mol_type = protein
                        organism = synthetic construct
REGION                  1..21
                        note = H3N2 epitope
SEQUENCE: 22
LGHHAVPNGT LVKTITNDGG K                                            21

SEQ ID NO: 23           moltype = AA  length = 27
FEATURE                 Location/Qualifiers
source                  1..27
                        mol_type = protein
                        organism = synthetic construct
REGION                  1..27
                        note = H1N1 epitope
SEQUENCE: 23
FAWRSRNENE RPSLPPKQKR EVAGGGK                                      27

SEQ ID NO: 24           moltype = AA  length = 20
FEATURE                 Location/Qualifiers
source                  1..20
```

```
                            mol_type = protein
                            organism = synthetic construct
REGION                      1..20
                            note = H1N1 epitope
SE -continued

```
source                  1..18
                        mol_type = protein
                        organism = synthetic construct
REGION                  1..18
                        note = H1N1 epitope
SEQUENCE: 32
VSLGAISFWM SSNGSGGK                                         18

SEQ ID NO: 33           moltype = AA  length = 18
FEATURE                 Location/Qualifiers
source                  1..18
                        mol_type = protein
                        organism = synthetic construct
REGION                  1..18
                        note = H1N1 epitope
SEQUENCE: 33
AISFWMSSNG SLQSRGGK                                         18

SEQ ID NO: 34           moltype = AA  length = 17
FEATURE                 Location/Qualifiers
source                  1..17
                        mol_type = protein
                        organism = synthetic construct
REGION                  1..17
                        note = H1N1 epitope
SEQUENCE: 34
WMSSNGSLQS RISIGGK                                          17

SEQ ID NO: 35           moltype = DNA  length = 32
FEATURE                 Location/Qualifiers
source                  1..32
                        mol_type = other DNA
                        organism = synthetic construct
misc_feature            1..32
                        note = coding tag
misc_feature            32
                        note = modified with C3 (three carbon) spacer
misc_feature            1
                        note = modified with 5'-amino modifier C6 and 18 atoms
                         hexaethylene glycol chain (iSP18)
SEQUENCE: 35
cactcagttt ccgtcatatc gaatcactca gt                         32

SEQ ID NO: 36           moltype = AA  length = 20
FEATURE                 Location/Qualifiers
source                  1..20
                        mol_type = protein
                        organism = synthetic construct
REGION                  1..20
                        note = SpyTag
SEQUENCE: 36
CGSGSGSAHI VMVDAYKPTK                                       20

SEQ ID NO: 37           moltype = AA  length = 241
FEATURE                 Location/Qualifiers
source                  1..241
                        mol_type = protein
                        organism = synthetic construct
REGION                  1..241
                        note = SpyCatcher-SnoopCatcher
SEQUENCE: 37
VDTLSGLSSE QGQSGDMTIE EDSATHIKFS KRDEDGKELA GATMELRDSS GKTISTWISD  60
GQVKDFYLYP GKYTFVETAA PDGYEVATAI TFTVNEQGQV TVNGKATKGD AHIGGSGGGS  120
GGGSGGSKPL RGAVFSLQKQ HPDYPDIYGA IDQNGTYQNV RTGEDGKLTF KNLSDGKYRL  180
FENSEPAGYK PVQNKPIVAF QIVNGEVRDV TSIVPQDIPA TYEFTNGKHY ITNEPIPPKG  240
S                                                           241

SEQ ID NO: 38           moltype = AA  length = 556
FEATURE                 Location/Qualifiers
source                  1..556
                        mol_type = protein
                        organism = synthetic construct
REGION                  1..556
                        note = SpyCatcher-Protein A/G
SEQUENCE: 38
VDTLSGLSSE QGQSGDMTIE EDSATHIKFS KRDEDGKELA GATMELRDSS GKTISTWISD  60
GQVKDFYLYP GKYTFVETAA PDGYEVATAI TFTVNEQGQV TVNGKATKGD AHIGGSGGGS  120
GGGSGGSNAA QHDEAQQNAF YQVLNMPNLN ADQRNGFIQS LKDDPSQSAN VLGEAQKLND  180
SQAPKADAQQ NNFNKDQQSA FYEILNMPNL NEAQRNGFIQ SLKDDPSQST NVLGEAKKLN  240
```

```
ESQAPKADNN FNKEQQNAFY EILNMPNLNE EQRNGFIQSL KDDPSQSANL LSEAKKLNES   300
QAPKADNKFN KEQQNAFYEI LHLPNLNEEQ RNGFIQSLKD DPSQSANLLA EAKKLNDAQA   360
PKADNKFNKE QQNAFYEILH LPNLTEEQRN GFIQSLKDDP SVSKEILAEA KKLNDAQAPK   420
EEDSLEGSGS GTYKLILNGK TLKGETTTEA VDAATAEKVF KQYANDNGVD GEWTYDDATK   480
TFTVTEKPEV IDASELTPAV TTYKLVINGK TLKGETTTKA VDAETAEKAF KQYANDNGVD   540
GVWTYDDATK TFTVTE                                                 556

SEQ ID NO: 39           moltype = AA  length = 389
FEATURE                 Location/Qualifiers
source                  1..389
                        mol_type = protein
                        organism = Staphylococcus aureus
REGION                  1..389
                        note = Protein A
SEQUENCE: 39
MKKKNIYSIR KLGVGIASVT LGTLLISGGV TPAANAAQHD EAQQNAFYQV LNMPNLNADQ    60
RNGFIQSLKD DPSQSANLLS EAKKLNESQA PKADNKFNKE QQNAFYEILH LPNLNEEQRN   120
GFIQSLKDDP SQSANLLAEA KKLNDAQAPK ADNKFNKEQQ NAFYEILHLP NLTEEQRNGF   180
IQSLKDDPSV SKEILAEAKK LNDAQAPKEE DNNKPGKEDG NKPGKEDNNK PGKEDNKKPG   240
KEDNKKPGKE DNNKPGKEDG NKPGKEDNKK PGKEDNNKPG KEDGNKPGKE DGNGVHVVKP   300
GDTVNDIAKA NGTTADKIAA DNKLADKNMI KPGQELVVDK KQPANHADAN KAQALPETGE   360
ENPFIGTTVF GGLSLALGAA LLAGRRREL                                   389

SEQ ID NO: 40           moltype = AA  length = 448
FEATURE                 Location/Qualifiers
source                  1..448
                        mol_type = protein
                        organism = Streptococcus sp.
REGION                  1..448
                        note = Protein G
SEQUENCE: 40
MEKEKKVKYF LRKSAFGLAS VSAAFLVGST VFAVDSPIED TPIIRNGGEL TNLLGNSETT    60
LALRNEESAT ADLTAAAVAD TVAAAAAENA GAAAWEAAAA ADALAKAKAD ALKEFNKYGV   120
SDYYKNLINN AKTVEGIKDL QAQVVESAKK ARISEATDGL SDFLKSQTPA EDTVKSIELA   180
EAKVLANREL DKYGVSDYHK NLINNAKTVE GVKELIDEIL AALPKTDTYK LILNGKTLKG   240
ETTTEAVDAA TAEKVFKQYA NDNGVDGEWT YDDATKTFTV TEKPEVIDAS ELTPAVTTYK   300
LVINGKTLKG ETTTKAVDAE TAEKAFKQYA NDNGVDGVWT YDDATKTFTV TEMVTEVPGD   360
APTEPEKPEA SIPLVPLTPA TPIAKDDAKK DDTKKEDAKK PEAKKDDAKK AETLPTTGEG   420
SNPFFTAAAL AVMAGAGALA VASKRKED                                    448

SEQ ID NO: 41           moltype = AA  length = 992
FEATURE                 Location/Qualifiers
source                  1..992
                        mol_type = protein
                        organism = Finegoldia magna
REGION                  1..992
                        note = Protein L
SEQUENCE: 41
MKINKKLLMA ALAGAIVVGG GANAYAAEED NTDNNLSMDE ISDAYFDYHG DVSDSVDPVE    60
EEIDEALAKA LAEAKETAKK HIDSLNHLSE TAKKLAKNDI DSATTINAIN DIVARADVME   120
RKTAEKEEAE KLAAAKETAK KHIDELKHLA DKTKELAKRD IDSATTINAI NDIVARADVM   180
ERKTAEKEEA EKLAAAKETA KKHIDELKHL ADKTKELAKR DIDSATTIDA INDIVARADV   240
MERKLSEKET PEPEEEVTIK ANLIFADGST QNAEFKGTFA KAVSDAYAYA DALKKDNGEY   300
TVDVADKGLT LNIKFAGKKE KPEEPKEEVT IKVNLIFADG KTQTAEFKGT FEEATAKAYA   360
YADLLAKENG EYTADLEDGG NTINIKFAGK ETPETPEEPK EEVTIKVNLI FADGKIQTAE   420
FKGTFEEATA KAYAYANLLA KENGEYTADL EDGGNTINIK FAGKETPETP EEPKEEVTIK   480
VNLIFADGKT QTAEFKGTFE EATAEAYRYA DLLAKVNGEY TADLEDGGYT INIKFAGKEQ   540
PGENPGITID EWLLKNAKEE AIKELKEAGI TSDLYFSLIN KAKTVEGVEA LKNEILKAHA   600
GEETPELKDG YATYEEAEAA AKEALKNDDV NNAYEIVQGA DGRYYYVLKI EVADEEEPGE   660
DTPEVQEGYA TYEEAEAAAK EALKEDKVNN AYEVVQGADG RYYYVLKIED KEDEQPGEEP   720
GENPGITIDE WLLKNAKEDA IKELKEAGIS SDIYFDAINK AKTVEGVEAL KNEILKAHAE   780
KPGENPGITI DEWLLKNAKE AAIKELKEAG ITAEYLFNLI NKAKTVEGVE SLKNEILKAH   840
AEKPGENPGI TIDEWLLKNA KEDAIKELKE AGITSDIYFD AINKAKTIEG VEALKNEILK   900
AHKKDEEPGK KPGEDKKPED KKPGEDKKPE DKKPGKTDK DSPNKKKKAK   960
LPKAGSEAEI LTLAAAALST AAGAYVSLKK RK                                992

SEQ ID NO: 42           moltype = AA  length = 12
FEATURE                 Location/Qualifiers
source                  1..12
                        mol_type = protein
                        organism = synthetic construct
REGION                  1..12
                        note = SnoopTag
SEQUENCE: 42
KLGDIEFIKV NK                                                      12

SEQ ID NO: 43           moltype = AA  length = 116
FEATURE                 Location/Qualifiers
source                  1..116
```

```
                        mol_type = protein
                        organism = synthetic construct
REGION                  1..116
                        note = SpyCatcher
SEQUENCE: 43
AMVDTLSGLS SEQGQSGDMT IEEDSATHIK FSKRDEDGKE LAGATMELRD SSGKTISTWI  60
SDGQVKDFYL YPGKYTFVET AAPDGYEVAT AITFTVNEQG QVTVNGKATK GDAHID     116

SEQ ID NO: 44           moltype = AA  length = 58
FEATURE                 Location/Qualifiers
source                  1..58
                        mol_type = protein
                        organism = synthetic construct
REGION                  1..58
                        note = Z domain of Protein A
SEQUENCE: 44
VDNKFNKEQQ NAFYEILHLP NLTEEQRNAF IQSLKDDPSV SKEILAEAKK LNDAQAPK    58

SEQ ID NO: 45           moltype = AA  length = 56
FEATURE                 Location/Qualifiers
source                  1..56
                        mol_type = protein
                        organism = synthetic construct
REGION                  1..56
                        note = C2 domain of Protein G
SEQUENCE: 45
TTYKLVINGK TLKGETTTKA VDAETAEKAF KQYANDNGVD GVWTYDDATK TFTVTE      56

SEQ ID NO: 46           moltype = AA  length = 520
FEATURE                 Location/Qualifiers
source                  1..520
                        mol_type = protein
                        organism = Mycoplasma genitalium
REGION                  1..520
                        note = mature protein M
SEQUENCE: 46
TNLVNQSGYA LVASGRSGNL GFKLFSTQSP SAEVKLKSLS LNDGSYQSEI DLSGGANFRE  60
KFRNFANELS EAITNSPKGL DRPVPKTEIS GLIKTGDNFI TPSFKAGYYD HVASDGSLLS  120
YYQSTEYFNN RVLMPILQTT NGTLMANNRG YDDVFRQVPS FSGWSNTKAT TVSTSNNLTY  180
DKWTYFAAKG SPLYDSYPNH FFEDVKTLAI DAKDISALKT TIDSEKPTYL IIRGLSGNGS  240
QLNELQLPES VKKVSLYGDY TGVNVAKQIF ANVVELEFYS TSKANSFGFN PLVLGSKTNV  300
IYDLFASKPF THIDLTQVTL QNSDNSAIDA NKLKQAVGDI YNYRRFERQF QGYFAGGYID  360
KYLVKNVNTN KDSDDDLVYR SLKELNLHLE EAYREGDNTY YRVNENYYPG ASIYENERAS  420
RDSEFQNEIL KRAEQNGVTF DENIKRITAS GKYSVQFQKL ENDTDSSLER MTKAVEGLVT  480
VIGEEKFETV DITGVSSDTN EVKSLAKELK TNALGVKLKL                       520

SEQ ID NO: 47           moltype = AA  length = 547
FEATURE                 Location/Qualifiers
source                  1..547
                        mol_type = protein
                        organism = Mycoplasma pneumoniae
REGION                  1..547
                        note = mature protein M
SEQUENCE: 47
AVLIVNEVLR LQSGETLIAS GRSGNLSFQL YSKVNQNAKS KLNSISLTDG GYRSEIDLGD  60
GSNFREDFRN FANNLSEAIT DAPKDLLRPV PKVEVSGLIK TSSTFITPNF KAGYYDQVAA  120
DGKTLKYYQS TEYFNNRVVM PILQTTNGTL TANNRAYDDI FVDQGVPKFP GWFHDVDKAY  180
YAGSNGQSEY LFKEWNYYVA NGSPLYNVYP NHHFKQIKTI AFDAPRIKQG NTDGINLNLK  240
QRNPDVVIIN GLTGDGSTLK DLELPESVKK VSIYGDYHSI NVAKQIFKNV LELEFYSTNQ  300
DNNFGFNPLV LGDHTNIIYD LFASKPFNYI DLTSLELKDN QDNIDASKLK RAVSDIYIRR  360
RFERQMQGYW AGGYIDRYLV KNTNEKNVNK DNDTVYAALK DINLHLEETY THGGNTMYRV  420
NENYYPGASA YEAERATRDS EFQKEIVQRA ELIGVVFEYG VKNLRPGLKY TVKFESPQEQ  480
VALKSTDKFQ PVIGSVTDMS KSVTDLIGVL RDNAEILNIT NVSKDETVVA ELKEKLDREN  540
VFQEIRT                                                           547

SEQ ID NO: 48           moltype = AA  length = 14
FEATURE                 Location/Qualifiers
source                  1..14
                        mol_type = protein
                        organism = synthetic construct
REGION                  1..14
                        note = FcBP-2 immunoglobulin-binding domain
SEQUENCE: 48
PDCAWHLGEL VWCT                                                   14

SEQ ID NO: 49           moltype = DNA  length = 13
FEATURE                 Location/Qualifiers
source                  1..13
                        mol_type = other DNA
```

-continued

```
                        organism = synthetic construct
misc_feature            1..13
                        note = stub DNA
misc_feature            1
                        note = conjugated to another oligonucleotide through
                          internal amino modifier C6 dT
SEQUENCE: 49
cggaagagcg tcg                                                           13

SEQ ID NO: 50           moltype = DNA  length = 97
FEATURE                 Location/Qualifiers
source                  1..97
                        mol_type = other DNA
                        organism = synthetic construct
misc_feature            1..97
                        note = capture DNA
misc_difference         17..26
                        note = n is a, c, g, or t
SEQUENCE: 50
cactcagtcc attaacnnnn nnnnnnctag tgtcgcggac tacgcattac tgagaagctt    60
gctagtcgac gtggtccttt tggaccacgt cgactag                             97
```